US006869930B1

(12) United States Patent
Havelund et al.

(10) Patent No.: US 6,869,930 B1
(45) Date of Patent: *Mar. 22, 2005

(54) ACYLATED INSULIN

(75) Inventors: Svend Havelund, Bagsvaerd (DK); John Halstrom, Hundested (DK); Ib Jonassen, Valby (DK); Asser Sloth Andersen, Frederiksberg (DK); Jan Markussen, Herlev (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/398,365

(22) Filed: Sep. 17, 1999

Related U.S. Application Data

(60) Division of application No. 08/975,365, filed on Nov. 20, 1997, now Pat. No. 6,011,007, which is a continuation-in-part of application No. 08/400,256, filed on Mar. 8, 1995, now Pat. No. 5,750,497, which is a continuation-in-part of application No. 08/190,829, filed on Feb. 2, 1994, now abandoned.

(30) Foreign Application Priority Data

Sep. 17, 1993 (DK) .............................................. 1044/93

(51) Int. Cl.$^7$ ......................... C07K 14/62; A61K 38/28
(52) U.S. Cl. ............................ 514/3; 514/866; 530/304
(58) Field of Search ................................ 530/303, 304; 514/3, 4

(56) References Cited

U.S. PATENT DOCUMENTS

| 3,528,960 A | | 9/1970 | Haas et al. | |
|---|---|---|---|---|
| 3,823,125 A | | 7/1974 | Grant et al. ............. | 260/112.7 |
| 3,868,356 A | | 2/1975 | Smyth ..................... | 260/112.7 |
| 3,868,357 A | | 2/1975 | Smyth et al. ............. | 260/112.7 |
| 3,869,437 A | | 3/1975 | Shall et al. | |
| 3,907,763 A | | 9/1975 | Brandenburg et al. ... | 260/112.7 |
| 3,950,517 A | * | 4/1976 | Lindsay et al. | |
| 4,645,740 A | | 2/1987 | Breddam et al. ............. | 435/71 |
| 5,008,241 A | * | 4/1991 | Markussen et al. | |
| 5,164,366 A | | 11/1992 | Balschmidt et al. | |
| 5,208,217 A | | 5/1993 | Panayotis | |
| 5,646,242 A | | 7/1997 | Baker et al. | |
| 5,693,609 A | | 12/1997 | Baker et al. | |
| 5,905,140 A | | 5/1999 | Hansen | |
| 5,922,675 A | | 7/1999 | Baker et al. | |
| 2001/0041786 A1 | | 11/2001 | Brader et al. | |

FOREIGN PATENT DOCUMENTS

| DE | 22 09 835 | 4/1976 |
|---|---|---|
| EP | 0 127 535 A2 | 5/1984 |
| EP | 0 280 534 B1 | 2/1988 |
| EP | 0 511 600 A2 | 11/1992 |
| EP | 1 27 107 A1 | 7/2002 |
| GB | 1343113 | 1/1974 |
| GB | 1 492 997 | 11/1977 |
| JP | 57-67548 | 4/1982 |
| JP | 1-254699 | * 10/1989 |
| WO | WO 91/12817 | 9/1991 |
| WO | WO 92/01476 | 2/1992 |
| WO | 95/07931 | 3/1995 |

OTHER PUBLICATIONS

Gammeltoft, Phys. Rev. 64. 1321–1378, 1984.*
Lindsay and Shall: The Acetylation of Insulin Biochem: (1991) 121, pp. 737–745.
Brange and Langkjaer: Chemical Stability of Insulin Acta Pharm. Nord.4(3) 149–158 (1992).
MIMS Annual 1991, Section 6d "Insulin Preparations" (IMB Publishing).
MIMS Annual 1993, Section 6d "Insulin Preparations" (IMS Publishing).
Prescription Products Guide 1992, pp. 942–944, 957–958 and 1307–1308.
J. Schlicktkrull, "Insulin Crystals" (Ejnar Munksgaard) 1958, pp. 21–33.
A Marble et al., Joslin's Diabetes Mellitus, 12th Edition, 1985, pp. 380–382.
Schade: Intensive Insulin Therapy, Exerpta Medica 1983, pp. 7 and 304.
W.D. Foye: Principles of Medicinal Chemistry 1974, pp. 563–565.
Doerge: Wilson and Gisvold's textbook of organic medicinal and pharmaceutical chemistry 1982, pp. 774–776.
Montague: Diabets and the Endocrine Pandreas—A Biochemical Approach, 1983, pp. 36 and 37.
Samuel et al., (1978) Clin. Exp. Immunol. 33:252–260.
Lapidot et al., Journal of Lipid Research, vol. 8, pp. 142–145, (1967).
Asada et al., Pharmaceutuical Research, vol. 11, No. 8, pp. 1115–1120 (1994).
Besselink et al., Applied Biochemistry and Biotechnology, vol. 43, pp. 227–246, (1993).
Boyd et al., Int. J. Peptide Protein Res. 4, pp. 109–115, (1972).

(List continued on next page.)

Primary Examiner—Jeffrey Siew
(74) Attorney, Agent, or Firm—Reza Green, Esq.; Richard W. Bork, Esq.; Marc A. Began, Esq.

(57) ABSTRACT

The present invention relates to protracted human insulin derivatives in which the A21 and the B3 amino acid residues are, independently, any amino acid residue which can be coded for by the genetic code except Lys, Arg and Cys; Phe$^{B1}$ may be deleted; the B30 amino acid residue is (a) a non-codable, lipophilic amino acid having from 10 to 24 carbon atoms, in which case an acyl group of a carboxylic acid with up to 5 carbon atoms is bound to the ε-amino group of Lys$^{B29}$; or (b) the B30 amino acid residue is deleted or is any amino acid residue which can be coded for by the genetic code except Lys, Arg and Cys, in any of which cases the ε-amino group of Lys$^{B29}$ has a lipophilic substituent; and any Zn$^{2+}$ complexes thereof with the proviso that when B30 is Thr or Ala and A21 and B3 are both Asn, and Phe$^{B1}$ is present, then the insulin derivative is always present as a Zn$^{2+}$ complex.

60 Claims, 3 Drawing Sheets

OTHER PUBLICATIONS

Boyd et al., Int. J. Peptide Protein Res. 4, pp. 109–114, (1972).
Bradbury et al., Eur. J. Biochem, vol. 76, pp. 573–582, (1977).
Brandenburg et al., Hoppe Seyler's Z. Physiol. Chem., vol. 353, pp. 599–616, (1972).
Cannan et al., Ann. N.Y. Acad. Sci., vol. 41, pp. 241–266, (1941).
Chan et al., Biochem. J., vol. 193, pp. 419–425, (1981).
Copper et al., Proc. Austr. Biochem Soc., vol. 3, p. 36, (1970).
Eugene Frederic. Journal of Polymer Science, vol. 12, pp. 287–300, (1954).
Friesen et al., Semisynthetic Peptides and Proteins, Offord & Dibello, pp. 161–179, (1977).
Muranishi et al., Journal of Controlled Release, vol. 19, pp. 179–188 (1992).
Brange J., Galenics of Insulin, pp. 18–100 (1987).
Blundell T. et al., The Structure In the Crystal and Its Reflection In Chemistry and Biology, vol. 26, pp. 279–402 (1972).
Markussen et al., Proc. Eng., vol. 2, pp. 157–166 (1988).
Brunfelt, ACTA Endocrinol. vol. 61, pp. 561–576 (1969).
Markussen, J. et al., Diabetologia 39: 281–288 (1996).
Krutzhals et al., J. Pharm. Sci. 85(3): 304–308 (1996).
Markussen et al., Protein Engineering 1(3):205–213 (1987).
Hashimoto et al., Pharmaceutical Research 6(2): 171–176 (1989).
Friesen, Insulin Chemistry, Structure and Function of Insulin and Related Hormones, Proceedings of the Second International Insulin Symposium Aachen, Germany, Sep. 4–7, 1979; Brandenburg and Wollmer, pp. 125–133.
Geiger et al., Hoppe Seyler's Z. Physiol. Chem. vol. 352, pp. 1487–1490, (1971).
Saul Lande, J. Org Chem., vol. 36, pp. 1267–1270, (1971).
Lande et al., Endocrinology, vol. 90, pp. 597–604, (1972).
Leclerc et al., Can, J. Chem. vol 46, pp. 1047–1051, (1968).
Lindsay et al., Eur. J. Biochem, vol. 15, pp. 547–554, (1970).
Lindsay et al., Biochem J. vol. 121, pp. 737–745, (1972).
Massey et al., Eur. J. Biochem, vol. 31, pp. 470–473, (1972).
May et al., J. Biol. Chem., vol. 253, pp. 686–690.
Saunders et al., FEBS Letters, vol. 26, pp. 286–288, (1972).
Saunders Thesis, pp. 63–67, (1974).
Saunders et al., Biochem J., vol. 165, pp. 479–486, (1977).
Schuttler, Hoppe Seyler's Z. Physiol. Chem., vol. 360, pp. 1721–1725, (1979).
Sheffer et al., Can. J. Biochem, vol. 57, pp. 489–496, (1979).
Tanford, J. Am. Chem. Soc., vol 72, pp. 441–451, (1950).
Tanford, Adv. Protein Chem., vol. 17, pp. 142–144, (1962).

* cited by examiner

SEQUENCE LISTING (1) GENERAL INFORMATION:

(iii) NUMBER OF SEQUENCES: 49

(2) INFORMATION FOR SEQ ID NO: 1:

(i) SEQUENCE CHARACTERISTICS:
      (A) LENGTH: 21 amino acids
      (B) TYPE: amino acid
      (D) TOPOLOGY: linear (ii) MOLECULE TYPE: protein (xi) SEQUENCE DESCRIPTION: SEQ ID NO: 1:

Gly Ile Val Glu Gln Cys Cys Thr Ser Ile Cys Ser Leu Tyr Gln Leu
1               5                   10                  15

Glu Asn Tyr Cys Xaa
                20

(2) INFORMATION FOR SEQ ID NO: 2:

(i) SEQUENCE CHARACTERISTICS:
      (A) LENGTH: 30 amino acids
      (B) TYPE: amino acid
      (D) TOPOLOGY: linear (ii) MOLECULE TYPE: protein (xi) SEQUENCE DESCRIPTION: SEQ ID NO: 2:

Xaa Val Xaa Gln His Leu Cys Gly Ser His Leu Val Glu Ala Leu Tyr
1               5                   10                  15

Leu Val Cys Gly Glu Arg Gly Phe Phe Tyr Thr Pro Lys Xaa
                20                  25                  30

(2) INFORMATION FOR SEQ ID NO: 3:

(i) SEQUENCE CHARACTERISTICS:
      (A) LENGTH: 110 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 3:

TGGCTAAGAG ATTCGTTGAC CAACACTTGT GCGGTTCTCA CTTGGTTGAA GCTTTGTACT          60

```
TGGTTTGTGG TGAAAGAGGT TTCTTCTACA CTCCAAAGTC TGACGACGCT        110
```

(2) INFORMATION FOR SEQ ID NO: 4:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

```
CTGCGGGCTG CGTCTAAGCA CAGTAGTTTT CCAATTGGTA CAAAGAACAG ATAGAAGTAC  60
AACATTGTTC AACGATACCC TTAGCGTCGT CAGACTTTGG                       100
```

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

```
GTCGCCATGG CTAAGAGATT CGTTG                                       25
```

(2) INFORMATION FOR SEQ ID NO: 6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

```
CTGCTCTAGA GCCTGCGGGC TGCGTCT                                     27
```

(2) INFORMATION FOR SEQ ID NO: 7:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

```
TGGCTAAGAG ATTCGTTACT CAACACTTGT GCGGTTCTCA CTTGGTTGAA GCTTTGTACT  60
TGGTTTGTGG TGAAAGAGGT TTCTTCTACA CTCCAAAGTC TGACGACGCT            110
```

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

```
GTCGCCATGG CTAAGAGATT CGTTA                                         25

(2) INFORMATION FOR SEQ ID NO: 9:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

CTGCGGGCTG CGTCTAACCA CAGTAGTTTT CCAATTGGTA CAAAGAACAG ATAGAAGTAC   60

AACATTGTTC AACGATACCC TTAGCGTCGT CAGACTTTGG                         100

(2) INFORMATION FOR SEQ ID NO: 10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

ACGTACGTTC TAGAGCCTGC GGGCTGC                                       27

(2) INFORMATION FOR SEQ ID NO: 11:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

CACTTGGTTG AAGCTTTGTA CTTGGTTTGT GGTGAAAGAG GTTTCTTCTA CACTCCAAAG   60

ACTAGAGGTA TCGTTGAA                                                 78

(2) INFORMATION FOR SEQ ID NO: 12:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

GCTAACGTCG CCATGGCTAA GAGAGAAGAA GCTGAAGCTG AAGCTAGATT CGTTAACCAA   60

CAC                                                                 63

(2) INFORMATION FOR SEQ ID NO: 13:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA
```

-continued (xi) SEQUENCE DESCRIPTION: SEQ ID NO: 13:

GCTAACGTCG CCATGGCTAA GAGAGAAGAA GCTGAAGCGA AGCTGAAAGA TTCGTTAACC    60

AACAC    65

(2) INFORMATION FOR SEQ ID NO: 14:

(i) SEQUENCE CHARACTERISTICS:
      (A) LENGTH: 415 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 80..391

(xi) SEQUENCE DESCRIPTION: SEQ ID NO: 14:

```
ATCGAATTCC ATTCAAGAAT AGTTCAAACA GAAGATTAC AAACTATCAA TTTCATACAC           60

AATATAAACG ACCAAAAGA ATG AAG GCT GTT TTC TTG GTT TTG TCC TTG ATC          112
                     Met Lys Ala Val Phe Leu Val Leu Ser Leu Ile
                      1               5                      10

GGA TTC TGC TGG GCC CAA CCA GTC ACT GGC GAT GAA TCA TCT GTT GAG          160
Gly Phe Cys Trp Ala Gln Pro Val Thr Gly Asp Glu Ser Ser Val Glu
             15                  20                  25

ATT CCG GAA GAG TCT CTG ATC ATC GCT GAA AAC ACC ACT TTG GCT AAC          208
Ile Pro Glu Glu Ser Leu Ile Ile Ala Glu Asn Thr Thr Leu Ala Asn
         30                  35                  40

GTC GCC ATG GCT AAG AGA TTC GTT AAC CAA CAC TTG TGC GGT TCT CAC          256
Val Ala Met Ala Lys Arg Phe Val Asn Gln His Leu Cys Gly Ser His
     45                  50                  55

TTG GTT GAA GCT TTG TAC TTG GTT TGT GGT GAA AGA GGT TTC TTC TAC          304
Leu Val Glu Ala Leu Tyr Leu Val Cys Gly Glu Arg Gly Phe Phe Tyr
 60                  65                  70                  75

ACT CCA AAG TCT GAC GAC GCT AAG GGT ATC GTT GAA CAA TGT TGT ACT          352
Thr Pro Lys Ser Asp Asp Ala Lys Gly Ile Val Glu Gln Cys Cys Thr
                 80                  85                  90

TCT ATC TGT TCT TTG TAC CAA TTG GAA AAC TAC TGT AAC TAGACGCAGC          401
Ser Ile Cys Ser Leu Tyr Gln Leu Glu Asn Tyr Cys Asn
             95                 100

CCGCAGGCTC TAGA                                                          415
```

(2) INFORMATION FOR SEQ ID NO: 15:

(i) SEQUENCE CHARACTERISTICS:
      (A) LENGTH: 104 amino acids
      (B) TYPE: amino acid
      (D) TOPOLOGY: linear (ii) MOLECULE TYPE: protein (xi) SEQUENCE DESCRIPTION: SEQ ID NO: 15:

```
Met Lys Ala Val Phe Leu Val Leu Ser Leu Ile Gly Phe Cys Trp Ala
 1               5                  10                  15

Gln Pro Val Thr Gly Asp Glu Ser Ser Val Glu Ile Pro Glu Glu Ser
             20                  25                  30

Leu Ile Ile Ala Glu Asn Thr Thr Leu Ala Asn Val Ala Met Ala Lys
         35                  40                  45

Arg Phe Val Asn Gln His Leu Cys Gly Ser His Leu Val Glu Ala Leu
     50                  55                  60
```

```
       Tyr Leu Val Cys Gly Glu Arg Gly Phe Phe Tyr Thr Pro Lys Ser Asp
       65                  70                  75                  80

Asp Ala Lys Gly Ile Val Glu Gln Cys Cys Thr Ser Ile Cys Ser Leu
                       85                  90                  95

Tyr Gln Leu Glu Asn Tyr Cys Asn
                   100

(2) INFORMATION FOR SEQ ID NO: 16:

(i) SEQUENCE CHARACTERISTICS:
          (A) LENGTH: 415 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 16:

TAGCTTAAGG TAAGTTCTTA TCAAGTTTGT TCTTCTAATG TTTGATAGTT AAAGTATGTG      60

TTATATTTGC TGGTTTTCTT ACTTCCGACA AAAGAACCAA AACAGGAACT AGCCTAAGAC     120

GACCCGGGTT GGTCAGTGAC CGCTACTTAG TAGACAACTC TAAGGCCTTC TCAGAGACTA     180

GTAGCGACTT TTGTGGTGAA ACCGATTGCA GCGGTACCGA TTCTCTAAGC AATTGGTTGT     240

GAACACGCCA AGAGTGAACC AACTTCGAAA CATGAACCAA ACACCACTTT CTCCAAAGAA     300

GATGTGAGGT TTCAGACTGC TGCGATTCCC ATAGCAACTT GTTACAACAT GAAGATAGAC     360

AAGAAACATG GTTAACCTTT TGATGACATT GATCTGCGTC GGGCGTCCGA GATCT          415

(2) INFORMATION FOR SEQ ID NO: 17:

(i) SEQUENCE CHARACTERISTICS:
          (A) LENGTH: 523 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: CDS
          (B) LOCATION: 80..499

(xi) SEQUENCE DESCRIPTION: SEQ ID NO: 17:

ATCGAATTCC ATTCAAGAAT AGTTCAAACA AGAAGATTAC AAACTATCAA TTTCATACAC      60

AATATAAACG ATTAAAAGA ATG AGA TTT CCT TCA ATT TTT ACT GCA GTT TTA      112
                      Met Arg Phe Pro Ser Ile Phe Thr Ala Val Leu
                        1               5                   10

TTC GCA GCA TCC TCC GCA TTA GCT GCT CCA GTC AAC ACT ACA ACA GAA       160
Phe Ala Ala Ser Ser Ala Leu Ala Ala Pro Val Asn Thr Thr Thr Glu
            15                  20                  25

GAT GAA ACG GCA CAA ATT CCG GCT GAA GCT GTC ATC GGT TAC TCA GAT       208
Asp Glu Thr Ala Gln Ile Pro Ala Glu Ala Val Ile Gly Tyr Ser Asp
        30                  35                  40

TTA GAA GGG GAT TTC GAT GTT GCT GTT TTG CCA TTT TCC AAC AGC ACA       256
Leu Glu Gly Asp Phe Asp Val Ala Val Leu Pro Phe Ser Asn Ser Thr
    45                  50                  55

AAT AAC GGG TTA TTG TTT ATA AAT ACT ACT ATT GCC AGC ATT GCT GCT       304
Asn Asn Gly Leu Leu Phe Ile Asn Thr Thr Ile Ala Ser Ile Ala Ala
60                  65                  70                  75

AAA GAA GAA GGG GTA TCT TTG GAT AAG AGA GAA GTT AAC CAA CAC TTG       352
Lys Glu Glu Gly Val Ser Leu Asp Lys Arg Glu Val Asn Gln His Leu
                80                  85                  90
```

```
TGC GGT TCT CAC TTG GTT GAA GCT TTG TAC TTG GTT TGT GGT GAA AGA      400
Cys Gly Ser His Leu Val Glu Ala Leu Tyr Leu Val Cys Gly Glu Arg
            95                 100                 105

GGT TTC TTC TAC ACT GAA AAG TCT GAC GAC GCT AAG GGT ATC GTT GAA      448
Gly Phe Phe Tyr Thr Glu Lys Ser Asp Asp Ala Lys Gly Ile Val Glu
        110                 115                 120

CAA TGT TGT ACT TCT ATC TGT TCT TTG TAC CAA TTG GAA AAC TAC TGT      496
Gln Cys Cys Thr Ser Ile Cys Ser Leu Tyr Gln Leu Glu Asn Tyr Cys
    125                 130                 135

AAC TAGACGCAGC CCGCAGGCTC TAGA                                        523
Asn
140

(2) INFORMATION FOR SEQ ID NO: 18:

(i) SEQUENCE CHARACTERISTICS:
        (A) LENGTH: 140 amino acids
        (B) TYPE: amino acid
        (D) TOPOLOGY: linear (ii) MOLECULE TYPE: protein (xi) SEQUENCE DESCRIPTION: SEQ ID NO: 18:

Met Arg Phe Pro Ser Ile Phe Thr Ala Val Leu Phe Ala Ala Ser Ser
  1               5                  10                  15

Ala Leu Ala Ala Pro Val Asn Thr Thr Thr Glu Asp Glu Thr Ala Gln
               20                  25                  30

Ile Pro Ala Glu Ala Val Ile Gly Tyr Ser Asp Leu Glu Gly Asp Phe
           35                  40                  45

Asp Val Ala Val Leu Pro Phe Ser Asn Ser Thr Asn Asn Gly Leu Leu
       50                  55                  60

Phe Ile Asn Thr Thr Ile Ala Ser Ile Ala Ala Lys Glu Glu Gly Val
 65                  70                  75                  80

Ser Leu Asp Lys Arg Glu Val Asn Gln His Leu Cys Gly Ser His Leu
                85                  90                  95

Val Glu Ala Leu Tyr Leu Val Cys Gly Glu Arg Gly Phe Phe Tyr Thr
               100                 105                 110

Glu Lys Ser Asp Asp Ala Lys Gly Ile Val Glu Gln Cys Cys Thr Ser
           115                 120                 125

Ile Cys Ser Leu Tyr Gln Leu Glu Asn Tyr Cys Asn
       130                 135                 140

(2) INFORMATION FOR SEQ ID NO: 19:

(i) SEQUENCE CHARACTERISTICS:
        (A) LENGTH: 523 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

TAGCTTAAGG TAAGTTCTTA TCAAGTTTGT TCTTCTAATG TTTGATAGTT AAAGTATGTG     60

TTATATTTGC TAATTTTCTT ACTCTAAAGG AAGTTAAAAA TGACGTCAAA ATAAGCGTCG    120

TAGGAGGCGT AATCGACGAG GTCAGTTGTG ATGTTGTCTT CTACTTTGCC GTGTTTAAGG    180

CCGACTTCGA CAGTAGCCAA TGAGTCTAAA TCTTCCCCTA AAGCTACAAC GACAAAACGG    240

TAAAAGGTTG TCGTGTTTAT TGCCCAATAA CAAATATTTA TGATGATAAC GGTCGTAACG    300

ACGATTTCTT CTTCCCCATA GAAACCTATT CTCTCTTCAA TTGGTTGTGA ACACGCCAAG    360
```

```
AGTGAACCAA CTTCGAAACA TGAACCAAAC ACCACTTTCT CCAAAGAAGA TGTGACTTTT      420

CAGACTGCTG CGATTCCCAT AGCAACTTGT TACAACATGA AGATAGACAA GAAACATGGT      480

TAACCTTTTG ATGACATTGA TCTGCGTCGG GCGTCCGAGA TCT                       523
```

(2) INFORMATION FOR SEQ ID NO: 20:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 80..391

(xi) SEQUENCE DESCRIPTION: SEQ ID NO: 20:

```
ATCGAATTCC ATTCAAGAAT AGTTCAAACA GAAGATTAC AAACTATCAA TTTCATACAC        60

AATATAAACG ACCAAAAGA ATG AAG GCT GTT TTC TTG GTT TTG TCC TTG ATC       112
                     Met Lys Ala Val Phe Leu Val Leu Ser Leu Ile
                      1               5                      10

GGA TTC TGC TGG GCC CAA CCA GTC ACT GGC GAT GAA TCA TCT GTT GAG        160
Gly Phe Cys Trp Ala Gln Pro Val Thr Gly Asp Glu Ser Ser Val Glu
             15                  20                  25

ATT CCG GAA GAG TCT CTG ATC ATC GCT GAA AAC ACC ACT TTG GCT AAC        208
Ile Pro Glu Glu Ser Leu Ile Ile Ala Glu Asn Thr Thr Leu Ala Asn
         30                  35                  40

GTC GCC ATG GCT AAG AGA TTC GTT GAC CAA CAC TTG TGC GGT TCT CAC        256
Val Ala Met Ala Lys Arg Phe Val Asp Gln His Leu Cys Gly Ser His
     45                  50                  55

TTG GTT GAA GCT TTG TAC TTG GTT TGT GGT GAA AGA GGT TTC TTC TAC        304
Leu Val Glu Ala Leu Tyr Leu Val Cys Gly Glu Arg Gly Phe Phe Tyr
 60                  65                  70                  75

ACT CCA AAG TCT GAC GAC GCT AAG GGT ATC GTT GAA CAA TGT TGT ACT        352
Thr Pro Lys Ser Asp Asp Ala Lys Gly Ile Val Glu Gln Cys Cys Thr
                 80                  85                  90

TCT ATC TGT TCT TTG TAC CAA TTG GAA AAC TAC TGT GCT TAGACGCAGC         401
Ser Ile Cys Ser Leu Tyr Gln Leu Glu Asn Tyr Cys Ala
             95                 100

CCGCAGGCTC TAGA                                                        415
```

(2) INFORMATION FOR SEQ ID NO: 21:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO: 21:

```
Met Lys Ala Val Phe Leu Val Leu Ser Leu Ile Gly Phe Cys Trp Ala
 1               5                  10                  15

Gln Pro Val Thr Gly Asp Glu Ser Ser Val Glu Ile Pro Glu Glu Ser
                 20                  25                  30

Leu Ile Ile Ala Glu Asn Thr Thr Leu Ala Asn Val Ala Met Ala Lys
             35                  40                  45

Arg Phe Val Asp Gln His Leu Cys Gly Ser His Leu Val Glu Ala Leu
         50                  55                  60
```

```
Tyr Leu Val Cys Gly Glu Arg Gly Phe Phe Tyr Thr Pro Lys Ser Asp
 65                  70                  75                  80

Asp Ala Lys Gly Ile Val Glu Gln Cys Cys Thr Ser Ile Cys Ser Leu
                 85                  90                  95

Tyr Gln Leu Glu Asn Tyr Cys Ala
            100
```

(2) INFORMATION FOR SEQ ID NO: 22:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

```
TAGCTTAAGG TAAGTTCTTA TCAAGTTTGT TCTTCTAATG TTTGATAGTT AAAGTATGTG    60

TTATATTTGC TGGTTTTCTT ACTTCCGACA AAAGAACCAA AACAGGAACT AGCCTAAGAC   120

GACCCGGGTT GGTCAGTGAC CGCTACTTAG TAGACAACTC TAAGGCCTTC TCAGAGACTA   180

GTAGCGACTT TTGTGGTGAA ACCGATTGCA GCGGTACCGA TTCTCTAAGC AACTGGTTGT   240

GAACACGCCA AGAGTGAACC AACTTCGAAA CATGAACCAA ACACCACTTT CTCCAAAGAA   300

GATGTGAGGT TTCAGACTGC TGCGATTCCC ATAGCAACTT GTTACAACAT GAAGATAGAC   360

AAGAAACATG GTTAACCTTT TGATGACACG AATCTGCGTC GGGCGTCCGA GATCT        415
```

(2) INFORMATION FOR SEQ ID NO: 23:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 80..391

(xi) SEQUENCE DESCRIPTION: SEQ ID NO: 23:

```
ATCGAATTCC ATTCAAGAAT AGTTCAAACA AGAAGATTAC AAACTATCAA TTTCATACAC    60

AATATAAACG ACCAAAAGA ATG AAG GCT GTT TTC TTG GTT TTG TCC TTG ATC    112
                     Met Lys Ala Val Phe Leu Val Leu Ser Leu Ile
                       1               5                      10

GGA TTC TGC TGG GCC CAA CCA GTC ACT GGC GAT GAA TCA TCT GTT GAG    160
Gly Phe Cys Trp Ala Gln Pro Val Thr Gly Asp Glu Ser Ser Val Glu
            15                  20                  25

ATT CCG GAA GAG TCT CTG ATC ATC GCT GAA AAC ACC ACT TTG GCT AAC    208
Ile Pro Glu Glu Ser Leu Ile Ile Ala Glu Asn Thr Thr Leu Ala Asn
        30                  35                  40

GTC GCC ATG GCT AAG AGA TTC GTT ACT CAA CAC TTG TGC GGT TCT CAC    256
Val Ala Met Ala Lys Arg Phe Val Thr Gln His Leu Cys Gly Ser His
 45                  50                  55

TTG GTT GAA GCT TTG TAC TTG GTT TGT GGT GAA AGA GGT TTC TTC TAC    304
Leu Val Glu Ala Leu Tyr Leu Val Cys Gly Glu Arg Gly Phe Phe Tyr
 60                  65                  70                  75

ACT CCA AAG TCT GAC GAC GCT AAG GGT ATC GTT GAA CAA TGT TGT ACT    352
Thr Pro Lys Ser Asp Asp Ala Lys Gly Ile Val Glu Gln Cys Cys Thr
                 80                  85                  90
```

```
TCT ATC TGT TCT TTG TAC CAA TTG GAA AAC TAC TGT GCT TAGACGCAGC      401
Ser Ile Cys Ser Leu Tyr Gln Leu Glu Asn Tyr Cys Ala
            95                  100

CCGCAGGCTC TAGA                                                    415
```

(2) INFORMATION FOR SEQ ID NO: 24:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO: 24:

```
Met Lys Ala Val Phe Leu Val Leu Ser Leu Ile Gly Phe Cys Trp Ala
 1               5                  10                  15

Gln Pro Val Thr Gly Asp Glu Ser Ser Val Glu Ile Pro Glu Glu Ser
                20                  25                  30

Leu Ile Ile Ala Glu Asn Thr Thr Leu Ala Asn Val Ala Met Ala Lys
            35                  40                  45

Arg Phe Val Thr Gln His Leu Cys Gly Ser His Leu Val Glu Ala Leu
     50                  55                  60

Tyr Leu Val Cys Gly Glu Arg Gly Phe Phe Tyr Thr Pro Lys Ser Asp
 65                  70                  75                  80

Asp Ala Lys Gly Ile Val Glu Gln Cys Cys Thr Ser Ile Cys Ser Leu
                85                  90                  95

Tyr Gln Leu Glu Asn Tyr Cys Ala
            100
```

(2) INFORMATION FOR SEQ ID NO: 25:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

```
TAGCTTAAGG TAAGTTCTTA TCAAGTTTGT TCTTCTAATG TTTGATAGTT AAAGTATGTG      60

TTATATTTGC TGGTTTTCTT ACTTCCGACA AAAGAACCAA AACAGGAACT AGCCTAAGAC     120

GACCCGGGTT GGTCAGTGAC CGCTACTTAG TAGACAACTC TAAGGCCTTC TCAGAGACTA     180

GTAGCGACTT TTGTGGTGAA ACCGATTGCA GCGGTACCGA TTCTCTAAGC AATGAGTTGT     240

GAACACGCCA AGAGTGAACC AACTTCGAAA CATGAACCAA ACACCACTTT CTCCAAAGAA     300

GATGTGAGGT TTCAGACTGC TGCGATTCCC ATAGCAACTT GTTACAACAT GAAGATAGAC     360

AAGAAACATG GTTAACCTTT TGATGACACG AATCTGCGTC GGGCGTCCGA GATCT         415
```

(2) INFORMATION FOR SEQ ID NO: 26:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS (B) LOCATION: 80..391

(xi) SEQUENCE DESCRIPTION: SEQ ID NO: 26:

```
ATCGAATTCC ATTCAAGAAT AGTTCAAACA AGAAGATTAC AAACTATCAA TTTCATACAC            60

AATATAAACG ACCAAAAGA ATG AAG GCT GTT TTC TTG GTT TTG TCC TTG ATC           112
                     Met Lys Ala Val Phe Leu Val Leu Ser Leu Ile
                       1               5                  10

GGA TTC TGC TGG GCC CAA CCA GTC ACT GGC GAT GAA TCA TCT GTT GAG            160
Gly Phe Cys Trp Ala Gln Pro Val Thr Gly Asp Glu Ser Ser Val Glu
             15                  20                  25

ATT CCG GAA GAG TCT CTG ATC ATC GCT GAA AAC ACC ACT TTG GCT AAC            208
Ile Pro Glu Glu Ser Leu Ile Ile Ala Glu Asn Thr Thr Leu Ala Asn
         30                  35                  40

GTC GCC ATG GCT AAG AGA TTC GTT GAC CAA CAC TTG TGC GGT TCT CAC            256
Val Ala Met Ala Lys Arg Phe Val Asp Gln His Leu Cys Gly Ser His
 45                  50                  55

TTG GTT GAA GCT TTG TAC TTG GTT TGT GGT GAA AGA GGT TTC TTC TAC            304
Leu Val Glu Ala Leu Tyr Leu Val Cys Gly Glu Arg Gly Phe Phe Tyr
 60                  65                  70                  75

ACT CCA AAG TCT GAC GAC GCT AAG GGT ATC GTT GAA CAA TGT TGT ACT            352
Thr Pro Lys Ser Asp Asp Ala Lys Gly Ile Val Glu Gln Cys Cys Thr
                 80                  85                  90

TCT ATC TGT TCT TTG TAC CAA TTG GAA AAC TAC TGT GGT TAGACGCAGC             401
Ser Ile Cys Ser Leu Tyr Gln Leu Glu Asn Tyr Cys Gly
             95                 100

CCGCAGGCTC TAGA                                                            415
```

(2) INFORMATION FOR SEQ ID NO: 27:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO: 27:

```
Met Lys Ala Val Phe Leu Val Leu Ser Leu Ile Gly Phe Cys Trp Ala
  1               5                  10                  15

Gln Pro Val Thr Gly Asp Glu Ser Ser Val Glu Ile Pro Glu Glu Ser
             20                  25                  30

Leu Ile Ile Ala Glu Asn Thr Thr Leu Ala Asn Val Ala Met Ala Lys
         35                  40                  45

Arg Phe Val Asp Gln His Leu Cys Gly Ser His Leu Val Glu Ala Leu
     50                  55                  60

Tyr Leu Val Cys Gly Glu Arg Gly Phe Phe Tyr Thr Pro Lys Ser Asp
 65                  70                  75                  80

Asp Ala Lys Gly Ile Val Glu Gln Cys Cys Thr Ser Ile Cys Ser Leu
                 85                  90                  95

Tyr Gln Leu Glu Asn Tyr Cys Gly
            100
```

(2) INFORMATION FOR SEQ ID NO: 28:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 28:

```
TAGCTTAAGG TAAGTTCTTA TCAAGTTTGT TCTTCTAATG TTTGATAGTT AAAGTATGTG      60

TTATATTTGC TGGTTTTCTT ACTTCCGACA AAAGAACCAA AACAGGAACT AGCCTAAGAC     120

GACCCGGGTT GGTCAGTGAC CGCTACTTAG TAGACAACTC TAAGGCCTTC TCAGAGACTA     180

GTAGCGACTT TTGTGGTGAA ACCGATTGCA GCGGTACCGA TTCTCTAAGC AACTGGTTGT     240

GAACACGCCA AGAGTGAACC AACTTCGAAA CATGAACCAA ACACCACTTT CTCCAAAGAA     300

GATGTGAGGT TTCAGACTGC TGCGATTCCC ATAGCAACTT GTTACAACAT GAAGATAGAC     360

AAGAAACATG GTTAACCTTT TGATGACACC AATCTGCGTC GGGCGTCCGA GATCT          415
```

(2) INFORMATION FOR SEQ ID NO: 29:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 80..391

(xi) SEQUENCE DESCRIPTION: SEQ ID NO: 29:

```
ATCGAATTCC ATTCAAGAAT AGTTCAAACA AGAAGATTAC AAACTATCAA TTTCATACAC      60

AATATAAACG ACCAAAAGA ATG AAG GCT GTT TTC TTG GTT TTG TCC TTG ATC     112
                     Met Lys Ala Val Phe Leu Val Leu Ser Leu Ile
                       1               5                      10

GGA TTC TGC TGG GCC CAA CCA GTC ACT GGC GAT GAA TCA TCT GTT GAG      160
Gly Phe Cys Trp Ala Gln Pro Val Thr Gly Asp Glu Ser Ser Val Glu
             15                  20                  25

ATT CCG GAA GAG TCT CTG ATC ATC GCT GAA AAC ACC ACT TTG GCT AAC      208
Ile Pro Glu Glu Ser Leu Ile Ile Ala Glu Asn Thr Thr Leu Ala Asn
         30                  35                  40

GTC GCC ATG GCT AAG AGA TTC GTT ACT CAA CAC TTG TGC GGT TCT CAC      256
Val Ala Met Ala Lys Arg Phe Val Thr Gln His Leu Cys Gly Ser His
     45                  50                  55

TTG GTT GAA GCT TTG TAC TTG GTT TGT GGT GAA AGA GGT TTC TTC TAC      304
Leu Val Glu Ala Leu Tyr Leu Val Cys Gly Glu Arg Gly Phe Phe Tyr
 60                  65                  70                  75

ACT CCA AAG TCT GAC GAC GCT AAG GGT ATC GTT GAA CAA TGT TGT ACT      352
Thr Pro Lys Ser Asp Asp Ala Lys Gly Ile Val Glu Gln Cys Cys Thr
                 80                  85                  90

TCT ATC TGT TCT TTG TAC CAA TTG GAA AAC TAC TGT GGT TAGACGCAGC       401
Ser Ile Cys Ser Leu Tyr Gln Leu Glu Asn Tyr Cys Gly
                 95                 100

CCGCAGGCTC TAGA                                                      415
```

(2) INFORMATION FOR SEQ ID NO: 30:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO: 30:

Met Lys Ala Val Phe Leu Val Leu Ser Leu Ile Gly Phe Cys Trp Ala

```
          1               5              10              15
      Gln Pro Val Thr Gly Asp Glu Ser Ser Val Glu Ile Pro Glu Ser
                      20                  25                  30

Leu Ile Ile Ala Glu Asn Thr Thr Leu Ala Asn Val Ala Met Ala Lys
                   35                  40                  45

Arg Phe Val Thr Gln His Leu Cys Gly Ser His Leu Val Glu Ala Leu
                50                  55                  60

Tyr Leu Val Cys Gly Glu Arg Gly Phe Phe Tyr Thr Pro Lys Ser Asp
       65                  70                  75                  80

Asp Ala Lys Gly Ile Val Glu Gln Cys Cys Thr Ser Ile Cys Ser Leu
                      85                  90                  95

Tyr Gln Leu Glu Asn Tyr Cys Gly
                  100
```

(2) INFORMATION FOR SEQ ID NO: 31:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 31:

```
TAGCTTAAGG TAAGTTCTTA TCAAGTTTGT TCTTCTAATG TTTGATAGTT AAAGTATGTG     60

TTATATTTGC TGGTTTTCTT ACTTCCGACA AAAGAACCAA AACAGGAACT AGCCTAAGAC    120

GACCCGGGTT GGTCAGTGAC CGCTACTTAG TAGACAACTC TAAGGCCTTC TCAGAGACTA    180

GTAGCGACTT TTGTGGTGAA ACCGATTGCA GCGGTACCGA TTCTCTAAGC AATGAGTTGT    240

GAACACGCCA AGAGTGAACC AACTTCGAAA CATGAACCAA ACACCACTTT CTCCAAAGAA    300

GATGTGAGGT TTCAGACTGC TGCGATTCCC ATAGCAACTT GTTACAACAT GAAGATAGAC    360

AAGAAACATG GTTAACCTTT TGATGACACC AATCTGCGTC GGGCGTCCGA GATCT        415
```

(2) INFORMATION FOR SEQ ID NO: 32:

(i) SEQUENCE CHARACTERISTICS:
        (A) LENGTH: 523 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 80..499

(xi) SEQUENCE DESCRIPTION: SEQ ID NO: 32:

```
ATCGAATTCC ATTCAAGAAT AGTTCAAACA AGAAGATTAC AAACTATCAA TTTCATACAC     60

AATATAAACG ATTAAAAGA ATG AGA TTT CCT TCA ATT TTT ACT GCA GTT TTA    112
                     Met Arg Phe Pro Ser Ile Phe Thr Ala Val Leu
                       1               5                  10

TTC GCA GCA TCC TCC GCA TTA GCT GCT CCA GTC AAC ACT ACA ACA GAA    160
Phe Ala Ala Ser Ser Ala Leu Ala Ala Pro Val Asn Thr Thr Thr Glu
                15                  20                  25

GAT GAA ACG GCA CAA ATT CCG GCT GAA GCT GTC ATC GGT TAC TCA GAT    208
Asp Glu Thr Ala Gln Ile Pro Ala Glu Ala Val Ile Gly Tyr Ser Asp
         30                  35                  40

TTA GAA GGG GAT TTC GAT GTT GCT GTT TTG CCA TTT TCC AAC AGC ACA    256
```

```
Leu Glu Gly Asp Phe Asp Val Ala Val Leu Pro Phe Ser Asn Ser Thr
    45              50                  55

AAT AAC GGG TTA TTG TTT ATA AAT ACT ACT ATT GCC AGC ATT GCT GCT     304
Asn Asn Gly Leu Leu Phe Ile Asn Thr Thr Ile Ala Ser Ile Ala Ala
60              65                  70                  75

AAA GAA GAA GGG GTA TCT TTG GAT AAG AGA TTC GTT AAC CAA CAC TTG     352
Lys Glu Glu Gly Val Ser Leu Asp Lys Arg Phe Val Asn Gln His Leu
                80                  85                  90

TGC GGT TCT CAC TTG GTT GAA GCT TTG TAC TTG GTT TGT GGT GAA AGA     400
Cys Gly Ser His Leu Val Glu Ala Leu Tyr Leu Val Cys Gly Glu Arg
            95                  100                 105

GGT TTC TTC TAC ACT CCA AAG TCT GAC GAC GCT AAG GGT ATC GTT GAA     448
Gly Phe Phe Tyr Thr Pro Lys Ser Asp Asp Ala Lys Gly Ile Val Glu
        110                 115                 120

CAA TGT TGT ACT TCT ATC TGT TCT TTG TAC CAA TTG GAA AAC TAC TGT     496
Gln Cys Cys Thr Ser Ile Cys Ser Leu Tyr Gln Leu Glu Asn Tyr Cys
    125                 130                 135

AAC TAGACGCAGC CCGCAGGCTC TAGA                                      523
Asn
140

(2) INFORMATION FOR SEQ ID NO: 33:

(i) SEQUENCE CHARACTERISTICS:
        (A) LENGTH: 140 amino acids
        (B) TYPE: amino acid
        (D) TOPOLOGY: linear (ii) MOLECULE TYPE: protein (xi) SEQUENCE DESCRIPTION: SEQ ID NO: 33:

Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
 50                  55                  60

Phe Ile Asn Thr Thr Ile Ala Ser Ile Ala Ala Lys Glu Glu Gly Val
65                  70                  75                  80

Ser Leu Asp Lys Arg Phe Val Asn Gln His Leu Cys Gly Ser His Leu
                85                  90                  95

Val Glu Ala Leu Tyr Leu Val Cys Gly Glu Arg Gly Phe Phe Tyr Thr
            100                 105                 110

Pro Lys Ser Asp Asp Ala Lys Gly Ile Val Glu Gln Cys Cys Thr Ser
        115                 120                 125

Ile Cys Ser Leu Tyr Gln Leu Glu Asn Tyr Cys Asn
    130                 135                 140

(2) INFORMATION FOR SEQ ID NO: 34:

(i) SEQUENCE CHARACTERISTICS:
        (A) LENGTH: 523 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 34:
```

```
TAGCTTAAGG TAAGTTCTTA TCAAGTTTGT TCTTCTAATG TTTGATAGTT AAAGTATGTG      60

TTATATTTGC TAATTTTCTT ACTCTAAAGG AAGTTAAAAA TGACGTCAAA ATAAGCGTCG     120

TAGGAGGCGT AATCGACGAG GTCAGTTGTG ATGTTGTCTT CTACTTTGCC GTGTTTAAGG    180

CCGACTTCGA CAGTAGCCAA TGAGTCTAAA TCTTCCCCTA AAGCTACAAC GACAAAACGG    240

TAAAAGGTTG TCGTGTTTAT TGCCCAATAA CAAATATTTA TGATGATAAC GGTCGTAACG    300

ACGATTTCTT CTTCCCCATA GAAACCTATT CTCTAAGCAA TTGGTTGTGA ACACGCCAAG    360

AGTGAACCAA CTTCGAAACA TGAACCAAAC ACCACTTTCT CCAAAGAAGA TGTGAGGTTT    420

CAGACTGCTG CGATTCCCAT AGCAACTTGT TACAACATGA AGATAGACAA GAAACATGGT    480

TAACCTTTTG ATGACATTGA TCTGCGTCGG GCGTCCGAGA TCT                      523
```

(2) INFORMATION FOR SEQ ID NO: 35:

(i) SEQUENCE CHARACTERISTICS:
        (A) LENGTH: 409 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 80..385

(xi) SEQUENCE DESCRIPTION: SEQ ID NO: 35:

```
ATCGAATTCC ATTCAAGAAT AGTTCAAACA AGAAGATTAC AAACTATCAA TTTCATACAC      60

AATATAAACG ACCAAAAGA ATG AAG GCT GTT TTC TTG GTT TTG TCC TTG ATC     112
                     Met Lys Ala Val Phe Leu Val Leu Ser Leu Ile
                       1               5                      10

GGA TTC TGC TGG GCC CAA CCA GTC ACT GGC GAT GAA TCA TCT GTT GAG       160
Gly Phe Cys Trp Ala Gln Pro Val Thr Gly Asp Glu Ser Ser Val Glu
             15                  20                  25

ATT CCG GAA GAG TCT CTG ATC ATC GCT GAA AAC ACC ACT TTG GCT AAC       208
Ile Pro Glu Glu Ser Leu Ile Ile Ala Glu Asn Thr Thr Leu Ala Asn
         30                  35                  40

GTC GCC ATG GCT AAG AGA TTC GTT AAC CAA CAC TTG TGC GGT TCT CAC       256
Val Ala Met Ala Lys Arg Phe Val Asn Gln His Leu Cys Gly Ser His
     45                  50                  55

TTG GTT GAA GCT TTG TAC TTG GTT TGT GGT GAA AGA GGT TTC TTC TAC       304
Leu Val Glu Ala Leu Tyr Leu Val Cys Gly Glu Arg Gly Phe Phe Tyr
 60                  65                  70                  75

ACT CCT AAG GAA AAG AGA GGT ATC GTT GAA CAA TGT TGT ACT TCT ATC       352
Thr Pro Lys Glu Lys Arg Gly Ile Val Glu Gln Cys Cys Thr Ser Ile
                 80                  85                  90

TGT TCT TTG TAC CAA TTG GAA AAC TAC TGT GGT TAGACGCAGC CCGCAGGCTC     405
Cys Ser Leu Tyr Gln Leu Glu Asn Tyr Cys Gly
             95                 100

TAGA                                                                  409
```

(2) INFORMATION FOR SEQ ID NO: 36:

(i) SEQUENCE CHARACTERISTICS:
        (A) LENGTH: 102 amino acids
        (B) TYPE: amino acid
        (D) TOPOLOGY: linear (ii) MOLECULE TYPE: protein (xi) SEQUENCE DESCRIPTION: SEQ ID NO: 36:

```
Met Lys Ala Val Phe Leu Val Leu Ser Leu Ile Gly Phe Cys Trp Ala
 1               5                  10                  15

Gln Pro Val Thr Gly Asp Glu Ser Ser Val Glu Ile Pro Glu Ser
            20                  25                  30

Leu Ile Ile Ala Glu Asn Thr Thr Leu Ala Asn Val Ala Met Ala Lys
            35                  40                  45

Arg Phe Val Asn Gln His Leu Cys Gly Ser His Leu Val Glu Ala Leu
 50                  55                  60

Tyr Leu Val Cys Gly Glu Arg Gly Phe Phe Tyr Thr Pro Lys Glu Lys
 65                  70                  75                  80

Arg Gly Ile Val Glu Gln Cys Cys Thr Ser Ile Cys Ser Leu Tyr Gln
                85                  90                  95

Leu Glu Asn Tyr Cys Gly
            100
```

(2) INFORMATION FOR SEQ ID NO: 37:

(i) SEQUENCE CHARACTERISTICS:
        (A) LENGTH: 409 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 37:

```
TAGCTTAAGG TAAGTTCTTA TCAAGTTTGT TCTTCTAATG TTTGATAGTT AAAGTATGTG    60

TTATATTTGC TGGTTTTCTT ACTTCCGACA AAAGAACCAA AACAGGAACT AGCCTAAGAC   120

GACCCGGGTT GGTCAGTGAC CGCTACTTAG TAGACAACTC TAAGGCCTTC TCAGAGACTA   180

GTAGCGACTT TTGTGGTGAA ACCGATTGCA GCGGTACCGA TTCTCTAAGC AATTGGTTGT   240

GAACACGCCA AGAGTGAACC AACTTCGAAA CATGAACCAA ACACCACTTT CTCCAAAGAA   300

GATGTGAGGA TTCCTTTTCT CTCCATAGCA ACTTGTTACA ACATGAAGAT AGACAAGAAA   360

CATGGTTAAC CTTTTGATGA CACCAATCTG CGTCGGGCGT CCGAGATCT              409
```

(2) INFORMATION FOR SEQ ID NO: 38:

(i) SEQUENCE CHARACTERISTICS:
        (A) LENGTH: 511 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 77..487

(xi) SEQUENCE DESCRIPTION: SEQ ID NO: 38:

```
GAATTCCATT CAAGAATAGT TCAAACAAGA AGATTACAAA CTATCAATTT CATACACAAT    60

ATAAACGATT AAAAGA ATG AGA TTT CCT TCA ATT TTT ACT GCA GTT TTA       109
                  Met Arg Phe Pro Ser Ile Phe Thr Ala Val Leu
                   1               5                  10

TTC GCA GCA TCC TCC GCA TTA GCT GCT CCA GTC AAC ACT ACA ACA GAA    157
Phe Ala Ala Ser Ser Ala Leu Ala Ala Pro Val Asn Thr Thr Thr Glu
                15                  20                  25

GAT GAA ACG GCA CAA ATT CCG GCT GAA GCT GTC ATC GGT TAC TCA GAT    205
Asp Glu Thr Ala Gln Ile Pro Ala Glu Ala Val Ile Gly Tyr Ser Asp
         30                  35                  40
```

```
TTA GAA GGG GAT TTC GAT GTT GCT GTT TTG CCA TTT TCC AAC AGC ACA        253
Leu Glu Gly Asp Phe Asp Val Ala Val Leu Pro Phe Ser Asn Ser Thr
    45                  50                  55

AAT AAC GGG TTA TTG TTT ATA AAT ACT ACT ATT GCC AGC ATT GCT GCT        301
Asn Asn Gly Leu Leu Phe Ile Asn Thr Thr Ile Ala Ser Ile Ala Ala
60                  65                  70                  75

AAA GAA GAA GGG GTA TCC ATG GCT AAG AGA TTC GTT AAC CAA CAC TTG        349
Lys Glu Glu Gly Val Ser Met Ala Lys Arg Phe Val Asn Gln His Leu
                    80                  85                  90

TGC GGT TCC CAC TTG GTT GAA GCT TTG TAC TTG GTT TGT GGT GAA AGA        397
Cys Gly Ser His Leu Val Glu Ala Leu Tyr Leu Val Cys Gly Glu Arg
                95                  100                 105

GGT TTC TTC TAC ACT CCA AAG ACT AGA GGT ATC GTT GAA CAA TGT TGT        445
Gly Phe Phe Tyr Thr Pro Lys Thr Arg Gly Ile Val Glu Gln Cys Cys
            110                 115                 120

ACT TCT ATC TGT TCT TTG TAC CAA TTG GAA AAC TAC TGC AAC                487
Thr Ser Ile Cys Ser Leu Tyr Gln Leu Glu Asn Tyr Cys Asn
        125                 130                 135

TAGACGCAGC CCGCAGGCTC TAGA                                             511
```

(2) INFORMATION FOR SEQ ID NO: 39:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO: 39:

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Met Ala Lys Arg Phe Val Asn Gln His Leu Cys Gly Ser His Leu
                85                  90                  95

Val Glu Ala Leu Tyr Leu Val Cys Gly Glu Arg Gly Phe Phe Tyr Thr
            100                 105                 110

Pro Lys Thr Arg Gly Ile Val Glu Gln Cys Cys Thr Ser Ile Cys Ser
        115                 120                 125

Leu Tyr Gln Leu Glu Asn Tyr Cys Asn
130                 135
```

(2) INFORMATION FOR SEQ ID NO: 40:

(i) SEQUENCE CHARACTERISTICS:
        (A) LENGTH: 511 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 40:

```
CTTAAGGTAA GTTCTTATCA AGTTTGTTCT TCTAATGTTT GATAGTTAAA GTATGTGTTA    60
```

```
TATTTGCTAA TTTTCTTACT CTAAAGGAAG TTAAAAATGA CGTCAAAATA AGCGTCGTAG        120

GAGGCGTAAT CGACGAGGTC AGTTGTGATG TTGTCTTCTA CTTTGCCGTG TTTAAGGCCG        180

ACTTCGACAG TAGCCAATGA GTCTAAATCT TCCCCTAAAG CTACAACGAC AAAACGGTAA        240

AAGGTTGTCG TGTTTATTGC CCAATAACAA ATATTTATGA TGATAACGGT CGTAACGACG        300

ATTTCTTCTT CCCCATAGGT ACCGATTCTC TAAGCAATTG GTTGTGAACA CGCCAAGGGT        360

GAACCAACTT CGAAACATGA ACCAAACACC ACTTTCTCCA AGAAGATGT GAGGTTTCTG         420

ATCTCCATAG CAACTTGTTA CAACATGAAG ATAGACAAGA AACATGGTTA ACCTTTTGAT        480

GACGTTGATC TGCGTCGGGC GTCCGAGATC T                                      511

(2) INFORMATION FOR SEQ ID NO: 41:

(i) SEQUENCE CHARACTERISTICS:
        (A) LENGTH: 523 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 80..499

(xi) SEQUENCE DESCRIPTION: SEQ ID NO: 41:

ATCGAATTCC ATTCAAGAAT AGTTCAAACA AGAAGATTAC AAACTATCAA TTTCATACAC         60

AATATAAACG ATTAAAAGA ATG AGA TTT CCT TCA ATT TTT ACT GCA GTT TTA        112
                     Met Arg Phe Pro Ser Ile Phe Thr Ala Val Leu
                       1               5                      10

TTC GCA GCA TCC TCC GCA TTA GCT GCT CCA GTC AAC ACT ACA ACA GAA         160
Phe Ala Ala Ser Ser Ala Leu Ala Ala Pro Val Asn Thr Thr Thr Glu
                15                  20                  25

GAT GAA ACG GCA CAA ATT CCG GCT GAA GCT GTC ATC GGT TAC TCA GAT         208
Asp Glu Thr Ala Gln Ile Pro Ala Glu Ala Val Ile Gly Tyr Ser Asp
             30                  35                  40

TTA GAA GGG GAT TTC GAT GTT GCT GTT TTG CCA TTT TCC AAC AGC ACA         256
Leu Glu Gly Asp Phe Asp Val Ala Val Leu Pro Phe Ser Asn Ser Thr
         45                  50                  55

AAT AAC GGG TTA TTG TTT ATA AAT ACT ACT ATT GCC AGC ATT GCT GCT         304
Asn Asn Gly Leu Leu Phe Ile Asn Thr Thr Ile Ala Ser Ile Ala Ala
 60                  65                  70                  75

AAA GAA GAA GGG GTA TCC ATG GCT AAG AGA TTC GTT AAC CAA CAC TTG         352
Lys Glu Glu Gly Val Ser Met Ala Lys Arg Phe Val Asn Gln His Leu
                 80                  85                  90

TGC GGT TCC CAC TTG GTT GAA GCT TTG TAC TTG GTT TGC GGT GAA AGA         400
Cys Gly Ser His Leu Val Glu Ala Leu Tyr Leu Val Cys Gly Glu Arg
             95                 100                 105

GGT TTC TTC TAC ACT CCT AAG TCT GAC GAT GCT AAG GGT ATT GTC GAG         448
Gly Phe Phe Tyr Thr Pro Lys Ser Asp Asp Ala Lys Gly Ile Val Glu
         110                 115                 120

CAA TGC TGT ACC TCC ATC TGC TCC TTG TAC CAA TTG GAA AAC TAC TGC         496
Gln Cys Cys Thr Ser Ile Cys Ser Leu Tyr Gln Leu Glu Asn Tyr Cys
     125                 130                 135

AAC TAGACGCAGC CCGCAGGCTC TAGA                                          523
Asn
140

(2) INFORMATION FOR SEQ ID NO: 42:
```

(i) SEQUENCE CHARACTERISTICS:
       (A) LENGTH: 140 amino acids
       (B) TYPE: amino acid
       (D) TOPOLOGY: linear (ii) MOLECULE TYPE: protein (xi) SEQUENCE DESCRIPTION: SEQ ID NO: 42:

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Met Ala Lys Arg Phe Val Asn Gln His Leu Cys Gly Ser His Leu
                85                  90                  95

Val Glu Ala Leu Tyr Leu Val Cys Gly Glu Arg Gly Phe Phe Tyr Thr
            100                 105                 110

Pro Lys Ser Asp Asp Ala Lys Gly Ile Val Glu Gln Cys Cys Thr Ser
        115                 120                 125

Ile Cys Ser Leu Tyr Gln Leu Glu Asn Tyr Cys Asn
    130                 135                 140

(2) INFORMATION FOR SEQ ID NO: 43:

(i) SEQUENCE CHARACTERISTICS:
       (A) LENGTH: 523 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 43:

TAGCTTAAGG TAAGTTCTTA TCAAGTTTGT TCTTCTAATG TTTGATAGTT AAAGTATGTG      60

TTATATTTGC TAATTTTCTT ACTCTAAAGG AAGTTAAAAA TGACGTCAAA ATAAGCGTCG     120

TAGGAGGCGT AATCGACGAG GTCAGTTGTG ATGTTGTCTT CTACTTTGCC GTGTTTAAGG    180

CCGACTTCGA CAGTAGCCAA TGAGTCTAAA TCTTCCCCTA AAGCTACAAC GACAAAACGG    240

TAAAAGGTTG TCGTGTTTAT TGCCCAATAA CAAATATTTA TGATGATAAC GGTCGTAACG    300

ACGATTTCTT CTTCCCCATA GGTACCGATT CTCTAAGCAA TTGGTTGTGA ACACGCCAAG    360

GGTGAACCAA CTTCGAAACA TGAACCAAAC GCCACTTTCT CCAAAGAAGA TGTGAGGATT    420

CAGACTGCTA CGATTCCCAT AACAGCTCGT TACGACATGG AGGTAGACGA GGAACATGGT    480

TAACCTTTTG ATGACGTTGA TCTGCGTCGG GCGTCCGAGA TCT                      523

(2) INFORMATION FOR SEQ ID NO: 44:

(i) SEQUENCE CHARACTERISTICS:
       (A) LENGTH: 535 base pairs
       (B) TYPE: nucleic acid
       (C) STRANDEDNESS: single
       (D) TOPOLOGY: linear (ii) MOLECULE TYPE: cDNA (ix) FEATURE:

(A) NAME/KEY: CDS
(B) LOCATION: 77..511

(xi) SEQUENCE DESCRIPTION: SEQ ID NO: 44:

```
GAATTCCATT CAAGAATAGT TCAAACAAGA AGATTACAAA CTATCAATTT CATACACAAT      60

ATAAACGATT AAAAGA ATG AGA TTT CCT TCA ATT TTT ACT GCA GTT TTA         109
               Met Arg Phe Pro Ser Ile Phe Thr Ala Val Leu
                 1               5                  10

TTC GCA GCA TCC TCC GCA TTA GCT GCT CCA GTC AAC ACT ACA ACA GAA      157
Phe Ala Ala Ser Ser Ala Leu Ala Ala Pro Val Asn Thr Thr Thr Glu
             15                  20                  25

GAT GAA ACG GCA CAA ATT CCG GCT GAA GCT GTC ATC GGT TAC TCA GAT      205
Asp Glu Thr Ala Gln Ile Pro Ala Glu Ala Val Ile Gly Tyr Ser Asp
         30                  35                  40

TTA GAA GGG GAT TTC GAT GTT GCT GTT TTG CCA TTT TCC AAC AGC ACA      253
Leu Glu Gly Asp Phe Asp Val Ala Val Leu Pro Phe Ser Asn Ser Thr
             45                  50                  55

AAT AAC GGG TTA TTG TTT ATA AAT ACT ACT ATT GCC AGC ATT GCT GCT      301
Asn Asn Gly Leu Leu Phe Ile Asn Thr Thr Ile Ala Ser Ile Ala Ala
 60                  65                  70                  75

AAA GAA GAA GGG GTA TCC ATG GCT AAG AGA GAA GAA GCT GAA GCT GAA      349
Lys Glu Glu Gly Val Ser Met Ala Lys Arg Glu Glu Ala Glu Ala Glu
             80                  85                  90

GCT AGA TTC GTT AAC CAA CAC TTG TGC GGT TCC CAC TTG GTT GAA GCT      397
Ala Arg Phe Val Asn Gln His Leu Cys Gly Ser His Leu Val Glu Ala
             95                 100                 105

TTG TAC TTG GTT TGT GGT GAA AGA GGT TTC TTC TAC ACT CCA AAG ACT      445
Leu Tyr Leu Val Cys Gly Glu Arg Gly Phe Phe Tyr Thr Pro Lys Thr
        110                 115                 120

AGA GGT ATC GTT GAA CAA TGT TGT ACT TCT ATC TGT TCT TTG TAC CAA      493
Arg Gly Ile Val Glu Gln Cys Cys Thr Ser Ile Cys Ser Leu Tyr Gln
125                 130                 135

TTG GAA AAC TAC TGC AAC TAGACGCAGC CCGCAGGCTC TAGA                   535
Leu Glu Asn Tyr Cys Asn
140                 145
```

(2) INFORMATION FOR SEQ ID NO: 45:

(i) SEQUENCE CHARACTERISTICS:
        (A) LENGTH: 145 amino acids
        (B) TYPE: amino acid
        (D) TOPOLOGY: linear (ii) MOLECULE TYPE: protein (xi) SEQUENCE DESCRIPTION: SEQ ID NO: 45:

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Met Ala Lys Arg Glu Glu Ala Glu Ala Glu Ala Arg Phe Val Asn
             85                  90                  95

Gln His Leu Cys Gly Ser His Leu Val Glu Ala Leu Tyr Leu Val Cys
            100                 105                 110
```

```
Gly Glu Arg Gly Phe Phe Tyr Thr Pro Lys Thr Arg Gly Ile Val Glu
            115                 120                 125

Gln Cys Cys Thr Ser Ile Cys Ser Leu Tyr Gln Leu Glu Asn Tyr Cys
    130                 135                 140

Asn
145

(2) INFORMATION FOR SEQ ID NO: 46:

(i) SEQUENCE CHARACTERISTICS:
        (A) LENGTH: 535 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 46:

CTTAAGGTAA GTTCTTATCA AGTTTGTTCT TCTAATGTTT GATAGTTAAA GTATGTGTTA    60

TATTTGCTAA TTTTCTTACT CTAAAGGAAG TTAAAAATGA CGTCAAAATA AGCGTCGTAG   120

GAGGCGTAAT CGACGAGGTC AGTTGTGATG TTGTCTTCTA CTTTGCCGTG TTTAAGGCCG   180

ACTTCGACAG TAGCCAATGA GTCTAAATCT TCCCCTAAAG CTACAACGAC AAAACGGTAA   240

AAGGTTGTCG TGTTTATTGC CCAATAACAA ATATTTATGA TGATAACGGT CGTAACGACG   300

ATTTCTTCTT CCCCATAGGT ACCGATTCTC TCTTCTTCGA CTTCGACTTC GATCTAAGCA   360

ATTGGTTGTG AACACGCCAA GGGTGAACCA ACTTCGAAAC ATGAACCAAA CACCACTTTC   420

TCCAAAGAAG ATGTGAGGTT TCTGATCTCC ATAGCAACTT GTTACAACAT GAAGATAGAC   480

AAGAAACATG GTTAACCTTT TGATGACGTT GATCTGCGTC GGGCGTCCGA GATCT        535

(2) INFORMATION FOR SEQ ID NO: 47:

(i) SEQUENCE CHARACTERISTICS:
        (A) LENGTH: 538 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 77..514

(xi) SEQUENCE DESCRIPTION: SEQ ID NO: 47:

GAATTCCATT CAAGAATAGT TCAAACAAGA AGATTACAAA CTATCAATTT CATACACAAT    60

ATAAACGATT AAAAGA ATG AGA TTT CCT TCA ATT TTT ACT GCA GTT TTA       109
               Met Arg Phe Pro Ser Ile Phe Thr Ala Val Leu
               1               5                  10

TTC GCA GCA TCC TCC GCA TTA GCT GCT CCA GTC AAC ACT ACA ACA GAA    157
Phe Ala Ala Ser Ser Ala Leu Ala Ala Pro Val Asn Thr Thr Thr Glu
                15                  20                  25

GAT GAA ACG GCA CAA ATT CCG GCT GAA GCT GTC ATC GGT TAC TCA GAT    205
Asp Glu Thr Ala Gln Ile Pro Ala Glu Ala Val Ile Gly Tyr Ser Asp
            30                  35                  40

TTA GAA GGG GAT TTC GAT GTT GCT GTT TTG CCA TTT TCC AAC AGC ACA    253
Leu Glu Gly Asp Phe Asp Val Ala Val Leu Pro Phe Ser Asn Ser Thr
        45                  50                  55

AAT AAC GGG TTA TTG TTT ATA AAT ACT ACT ATT GCC AGC ATT GCT GCT    301
Asn Asn Gly Leu Leu Phe Ile Asn Thr Thr Ile Ala Ser Ile Ala Ala
60                  65                  70                  75
```

```
AAA GAA GAA GGG GTA TCC ATG GCT AAG AGA GAA GAA GCT GAA GCT GAA      349
Lys Glu Glu Gly Val Ser Met Ala Lys Arg Glu Glu Ala Glu Ala Glu
                80                  85                  90

GCT GAA AGA TTC GTT AAC CAA CAC TTG TGC GGT TCC CAC TTG GTT GAA      397
Ala Glu Arg Phe Val Asn Gln His Leu Cys Gly Ser His Leu Val Glu
                    95                 100                 105

GCT TTG TAC TTG GTT TGT GGT GAA AGA GGT TTC TTC TAC ACT CCA AAG      445
Ala Leu Tyr Leu Val Cys Gly Glu Arg Gly Phe Phe Tyr Thr Pro Lys
                110                 115                 120

ACT AGA GGT ATC GTT GAA CAA TGT TGT ACT TCT ATC TGT TCT TTG TAC      493
Thr Arg Gly Ile Val Glu Gln Cys Cys Thr Ser Ile Cys Ser Leu Tyr
        125                 130                 135

CAA TTG GAA AAC TAC TGC AAC TAGACGCAGC CCGCAGGCTC TAGA               538
Gln Leu Glu Asn Tyr Cys Asn
140                 145

(2) INFORMATION FOR SEQ ID NO: 48:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 48:

Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Met Ala Lys Arg Glu Glu Ala Glu Ala Glu Ala Glu Arg Phe Val
                85                  90                  95

Asn Gln His Leu Cys Gly Ser His Leu Val Glu Ala Leu Tyr Leu Val
                100                 105                 110

Cys Gly Glu Arg Gly Phe Phe Tyr Thr Pro Lys Thr Arg Gly Ile Val
            115                 120                 125

Glu Gln Cys Cys Thr Ser Ile Cys Ser Leu Tyr Gln Leu Glu Asn Tyr
        130                 135                 140

Cys Asn
145

(2) INFORMATION FOR SEQ ID NO: 49:

(i) SEQUENCE CHARACTERISTICS:
        (A) LENGTH: 538 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 49:

CTTAAGGTAA GTTCTTATCA AGTTTGTTCT TCTAATGTTT GATAGTTAAA GTATGTGTTA      60

TATTTGCTAA TTTTCTTACT CTAAAGGAAG TTAAAAATGA CGTCAAAATA AGCGTCGTAG     120
```

-continued

```
GAGGCGTAAT CGACGAGGTC AGTTGTGATG TTGTCTTCTA CTTTGCCGTG TTTAAGGCCG    180

ACTTCGACAG TAGCCAATGA GTCTAAATCT TCCCCTAAAG CTACAACGAC AAAACGGTAA    240

AAGGTTGTCG TGTTTATTGC CCAATAACAA ATATTTATGA TGATAACGGT CGTAACGACG    300

ATTTCTTCTT CCCCATAGGT ACCGATTCTC TCTTCTTCGA CTTCGACTTC GACTTTCTAA    360

GCAATTGGTT GTGAACACGC CAAGGGTGAA CCAACTTCGA AACATGAACC AAACACCACT    420

TTCTCCAAAG AAGATGTGAG GTTTCTGATC TCCATAGCAA CTTGTTACAA CATGAAGATA    480

GACAAGAAAC ATGGTTAACC TTTTGATGAC GTTGATCTGC GTCGGCGTC CGAGATCT      538
```

ACYLATED INSULIN

CROSS-REFERENCE TO RELATED APPLICATIONS

This application is a divisional of application Ser. No. 08/975,365 filed Nov. 20, 1997 now U.S. Pat. No. 6,011,007, which is a continuation-in-part of application Ser. No. 08/400,256 filed Mar. 8, 1995, now U.S. Pat. No. 5,750,497, which is a continuation-in-part of application Ser. No. 08/190,829 filed Feb. 2, 1994, now abandoned, and serial no. PCT DK94 00347 filed Sep. 16, 1994, now abandoned, which claims priority under 35 USC 119 of Danish application no. 194493 filed Sep. 17, 1993, the contents of which are fully incorporated herein by reference.

FIELD OF THE INVENTION

The present invention relates to novel human insulin derivatives which are soluble and have a protracted profile of action, to a method of providing such derivatives, to pharmaceutical compositions containing them, and to the use of such insulin derivatives in the treatment of diabetes.

BACKGROUND OF THE INVENTION

Many diabetic patients are treated with multiple daily insulin injections in a regimen comprising one or two daily injections of a protracted insulin to cover the basal requirement supplemented by bolus injections of a rapid acting insulin to cover the requirement related to meals.

Protracted insulin compositions are well known in the art. Thus, one main type of protracted insulin compositions comprises injectable aqueous suspensions of insulin crystals or amorphous insulin. In these compositions, the insulin compounds utilized typically are protamine insulin, zinc insulin or protamine zinc insulin.

Certain drawbacks are associated with the use of insulin suspensions. Thus, in order to secure an accurate dosing, the insulin particles must be suspended homogeneously by gentle shaking before a defined volume of the suspension is withdrawn from a vial or expelled from a cartridge. Also, for the storage of insulin suspensions, the temperature must be kept within more narrow limits than for insulin solutions in order to avoid lump formation or coagulation.

While it was earlier believed that protamines were non-immunogenic, it has now turned out that protamines can be immunogenic in man and that their use for medical purposes may lead to formation of antibodies (Samuel et al., Studies on the immunogenecity of protamines in humans and experimental animals by means of a micro-complement fixation test, Clin. Exp. Immunol. 33, pp. 252–260 (1978)).

Also, evidence has been found that the protamine-insulin complex is itself immunogenic (Kurtz et al., Circulating IgG antibody to protamine in patients treated with protamine-insulins. Diabetologica 25, pp. 322–324 (1983)). Therefore, with some patients the use of protracted insulin compositions containing protamines must be avoided.

Another type of protracted insulin compositions are solutions having a pH value below physiological pH from which the insulin will precipitate because of the rise in the pH value when the solution is injected. A drawback with these solutions is that the particle size distribution of the precipitate formed in the tissue on injection, and thus the timing of the medication, depends on the blood flow at the injection site and other parameters in a somewhat unpredictable manner. A further drawback is that the solid particles of the insulin may act as a local irritant causing inflammation of the tissue at the site of injection.

WO 91/12817 (Novo Nordisk A/S) discloses protracted, soluble insulin compositions comprising insulin complexes of cobalt(III). The protraction of these complexes is only intermediate and the bioavailability is reduced.

Human insulin has three primary amino groups: the N-terminal group of the A-chain and of the B-chain and the $\epsilon$-amino group of $Lys^{B29}$. Several insulin derivatives which are substituted in one or more of these groups are known in the prior art. Thus, U.S. Pat. No. 3,528,960 (Eli Lilly) relates to N-carboxyaroyl insulins in which one, two or three primary amino groups of the insulin molecule has a carboxyaroyl group. No specifically $N^{\epsilon B29}$-substituted insulins are disclosed.

According to GB Patent No. 1.492.997 (Nat. Res. Dev. Corp.), it has been found that insulin with a carbamyl substitution at $N^{\epsilon B29}$ has an improved profile of hypoglycaemic effect.

JP laid-open patent application No. 1-254699 (Kodama Co., Ltd.) discloses insulin wherein a fatty acid is bound to the amino group of $Phe^{B1}$ or to the $\epsilon$-amino group of $Lys^{B29}$ or to both of these. The stated purpose of the derivatisation is to obtain a pharmacologically acceptable, stable insulin preparation.

Insulins, which in the B30 position have an amino acid having at least five carbon atoms which cannot necessarily be coded for by a triplet of nucleotides, are described in JP laid-open patent application No. 57-067548 (Shionogi). The insulin analogues are claimed to be useful in the treatment of diabetes mellitus, particularly in patients who are insulin resistant due to generation of bovine or swine insulin antibodies.

By "insulin derivative" as used herein is meant a compound having a molecular structure similar to that of human insulin including the disulfide bridges between $Cys^{A7}$ and $Cys^{B7}$ and between $Cys^{A20}$ and $Cys^{B19}$ and an internal disulfide bridge between $Cys^{A6}$ and $Cys^{A11}$, and which have insulin activity.

However, there still is a need for protracted injectable insulin compositions which are solutions and contain insulins which stay in solution after injection and possess minimal inflammatory and immunogenic properties.

One object of the present invention is to provide human insulin derivatives, with a protracted profile of action, which are soluble at physiological pH values.

Another object of the present invention is to provide a pharmaceutical composition comprising the human insulin derivatives according to the invention.

It is a further object of the invention to provide a method of making the human insulin derivatives of the invention.

SUMMARY OF THE INVENTION

Surprisingly, it has turned out that certain human insulin derivatives, wherein the $\epsilon$-amino group of $Lys^{B29}$ has a lipophilic substituent, have a protracted profile of action and are soluble at physiological pH values.

Accordingly, in its broadest aspect, the present invention relates to an insulin derivative having the following sequence:

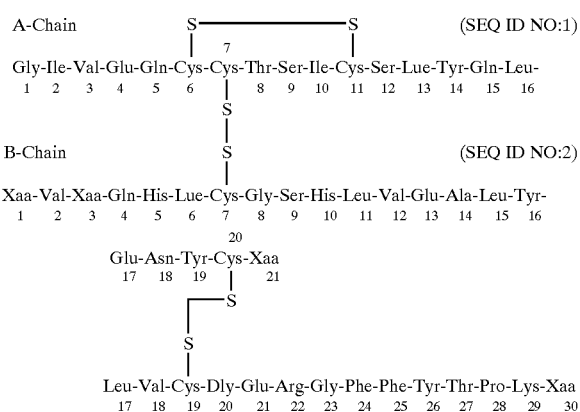

wherein
Xaa at positions A21 and B3 are, independently, any amino acid residue which can be coded for by the genetic code except Lys, Arg and Cys;
Xaa at position B1 is Phe or is deleted;
Xaa at position B30 is (a) a noncodable, lipophilic amino acid having from 10 to 24 carbon atoms, in which case an acyl group of a carboxylic acid with up to 5 carbon atoms is bound to the ϵ-amino group of $Lys^{B29}$, (b) any amino acid residue which can be coded for by the genetic code except Lys, Arg and Cys, in which case the ϵ-amino group of $Lys^{B29}$ has a lipophilic substituent or (c) deleted, in which case the ϵ-amino group of $Lys^{B29}$ has a lipophilic substituent; and any $Zn^{2+}$ complexes thereof, provided that when Xaa at position B30 is Thr or Ala, Xaa at positions A21 and B3 are both Asn, and Xaa at position B1 is Phe, then the insulin derivative is a $Zn^{2+}$ complex.

In one preferred embodiment, the invention relates to a human insulin derivative in which the B30 amino acid residue is deleted or is any amino acid residue which can be coded for by the genetic code except Lys, Arg and Cys; the A21 and the B3 amino acid residues are, independently, any amino acid residues which can be coded for by the genetic code except Lys, Arg and Cys; $Phe^{B1}$ may be deleted; the ϵ-amino group of $Lys^{B29}$ has a lipophilic substituent which comprises at least 6 carbon atoms; and 2–4 $Zn^{2+}$ ions may be bound to each insulin hexamer with the proviso that when B30 is Thr or Ala and A21 and B3 are both Asn, and $Phe^{B1}$ is not deleted, then 2–4 $Zn^{2+}$ ions are bound to each hexamer of the insulin derivative.

In another preferred embodiment, the invention relates to a human insulin derivative in which the B30 amino acid residue is deleted or is any amino acid residue which can be coded for by the genetic code except Lys, Arg and Cys; the A21 and the B3 amino acid residues are, independently, any amino acid residues which can be coded for by the genetic code except Lys, Arg and Cys, with the proviso that if the B30 amino acid residue is Ala or Thr, then at least one of the residues A21 and B3 is different from Asn; $Phe^{B1}$ may be deleted; and the ϵ-amino group of $Lys^{B29}$ has a lipophilic substituent which comprises at least 6 carbon atoms.

In another preferred embodiment, the invention relates to a human insulin derivative in which the B30 amino acid residue is deleted or is any amino acid residue which can be coded for by the genetic code except Lys, Arg and Cys; the A21 and the B3 amino acid residues are, independently, any amino acid residues which can be coded for by the genetic code except Lys, Arg and Cys; $Phe^{B1}$ may be deleted; the ϵ-amino group of $Lys^{B29}$ has a lipophilic substituent which comprises at least 6 carbon atoms; and 2–4 $Zn^{2+}$ ions are bound to each insulin hexamer.

In another preferred embodiment, the invention relates to a human insulin derivative in which the B30 amino acid residue is deleted.

In another preferred embodiment, the invention relates to a human insulin derivative in which the B30 amino acid residue is Asp.

In another preferred embodiment, the invention relates to a human insulin derivative in which the B30 amino acid residue is Glu.

In another preferred embodiment, the invention relates to a human insulin derivative in which the B30 amino acid residue is Thr.

In another preferred embodiment, the invention relates to a human insulin derivative in which the B30 amino acid is a lipophilic amino acid having at least 10 carbon atoms.

In another preferred embodiment, the invention relates to a human insulin derivative in which the B30 amino acid is a lipophilic α-amino acid having from 10 to 24 carbon atoms.

In another preferred embodiment, the invention relates to a human insulin derivative in which the B30 amino acid is a straight chain, saturated, aliphatic α-amino acid having from 10 to 24 carbon atoms.

In another preferred embodiment, the invention relates to a human insulin derivative in which the B30 amino acid is D- or L-$N^ϵ$-decanoyllysine.

In another preferred embodiment, the invention relates to a human insulin derivative in which the B30 amino acid is α-amino decanoic acid.

In another preferred embodiment, the invention relates to a human insulin derivative in which the B30 amino acid is α-amino undecanoic acid.

In another preferred embodiment, the invention relates to a human insulin derivative in which the B30 amino acid is α-amino dodecanoic acid.

In another preferred embodiment, the invention relates to a human insulin derivative in which the B30 amino acid is α-amino tridecanoic acid.

In another preferred embodiment, the invention relates to a human insulin derivative in which the B30 amino acid is α-amino tetradecanoic acid.

In another preferred embodiment, the invention relates to a human insulin derivative in which the B30 amino acid is α-amino pentadecanoic acid.

In another preferred embodiment, the invention relates to a human insulin derivative in which the B30 amino acid is α-amino hexadecanoic acid.

In another preferred embodiment, the invention relates to a human insulin derivative in which the B30 amino acid is an α-amino acid.

In another preferred embodiment, the invention relates to a human insulin derivative in which the A21 amino acid residue is Ala.

In another preferred embodiment, the invention relates to a human insulin derivative in which the A21 amino acid residue is Gln.

In another preferred embodiment, the invention relates to a human insulin derivative in which the A21 amino acid residue is Gly.

In another preferred embodiment, the invention relates to a human insulin derivative in which the A21 amino acid residue is Ser.

In another preferred embodiment, the invention relates to a human insulin derivative in which the B3 amino acid residue is Asp.

In another preferred embodiment, the invention relates to a human insulin derivative in which the B3 amino acid residue is Gln.

In another preferred embodiment, the invention relates to a human insulin derivative in which the B3 amino acid residue is Thr.

In another preferred embodiment, the invention relates to a human insulin derivative in which the ε-amino group of Lys$^{B29}$ has a lipophilic substituent which is an acyl group corresponding to a carboxylic acid having at least 6 carbon atoms.

In another preferred embodiment, the invention relates to a human insulin derivative in which the ε-amino group of Lys$^{B29}$ has a lipophilic substituent which is an acyl group, branched or unbranched, which corresponds to a carboxylic acid having a chain of carbon atoms 8 to 24 atoms long.

In another preferred embodiment, the invention relates to a human insulin derivative in which the ε-amino group of Lys$^{B29}$ has a lipophilic substituent which is an acyl group corresponding to a fatty acid having at least 6 carbon atoms.

In another preferred embodiment, the invention relates to a human insulin derivative in which the ε-amino group of Lys$^{B29}$ has a lipophilic substituent which is an acyl group corresponding to a linear, saturated carboxylic acid having from 6 to 24 carbon atoms.

In another preferred embodiment, the invention relates to a human insulin derivative in which the ε-amino group of Lys$^{B29}$ has a lipophilic substituent which is an acyl group corresponding to a linear, saturated carboxylic acid having from 8 to 12 carbon atoms.

In another preferred embodiment, the invention relates to a human insulin derivative in which the ε-amino group of Lys$^{B29}$ has a lipophilic substituent which is an acyl group corresponding to a linear, saturated carboxylic acid having from 10 to 16 carbon atoms.

In another preferred embodiment, the invention relates to a human insulin derivative in which the ε-amino group of Lys$^{B29}$ has a lipophilic substituent which is an oligo oxyethylene group comprising up to 10, preferably up to 5, oxyethylene units.

In another preferred embodiment, the invention relates to a human insulin derivative in which the ε-amino group of Lys$^{B29}$ has a lipophilic substituent which is an oligo oxypropylene group comprising up to 10, preferably up to 5, oxypropylene units.

In another preferred embodiment, the invention relates to a human insulin derivative in which each insulin hexamer binds 2 Zn$^{2+}$ ions.

In another preferred embodiment, the invention relates to a human insulin derivative in which each insulin hexamer binds 3 Zn$^{2+}$ ions.

In another preferred embodiment, the invention relates to a human insulin derivative in which each insulin hexamer binds 4 Zn$^{2+}$ ions.

In another preferred embodiment, the invention relates to the use of a human insulin derivative according to the invention for the preparation of a medicament for treating diabetes.

In another preferred embodiment, the invention relates to a pharmaceutical composition for the treatment of diabetes in a patient in need of such a treatment comprising a therapeutically effective amount of a human insulin derivative according to the invention together with a pharmaceutically acceptable carrier.

In another preferred embodiment, the invention relates to a pharmaceutical composition for the treatment of diabetes in a patient in need of such a treatment comprising a therapeutically effective amount of a human insulin derivative according to the invention, in mixture with an insulin or an insulin analogue which has a rapid onset of action, together with a pharmaceutically acceptable carrier.

In another preferred embodiment, the invention relates to a pharmaceutical composition comprising a human insulin derivative according to the invention which is soluble at physiological pH values.

In another preferred embodiment, the invention relates to a pharmaceutical composition comprising a human insulin derivative according to the invention which is a soluble at pH values in the interval from about 6.5 to about 8.5.

In another preferred embodiment, the invention relates to a protracted pharmaceutical composition comprising a human insulin derivative according to the invention.

In another preferred embodiment, the invention relates to a pharmaceutical composition which is a solution containing from about 120 nmol/ml to about 1200 nmol/ml, a preferably about 600 nmol/ml of a human insulin derivative according to the invention.

In another preferred embodiment, the invention relates to a method of treating diabetes in a patient in need of such a treatment comprising administering to the patient a therapeutically effective amount of an insulin derivative according to this invention together with a pharmaceutically acceptable carrier.

In another preferred embodiment, the invention relates to a method of treating diabetes in a patient in need of such a treatment comprising administering to the patient a therapeutically effective amount of an insulin derivative according to this invention, in mixture with an insulin or an insulin analogue which has a rapid onset of action, together with a pharmaceutically acceptable carrier.

Examples of preferred human insulin derivatives according to the present invention in which no Zn$^{2+}$ ions are bound are the following:

$N^{\epsilon B29}$-tridecanoyl des(B30) human insulin,
$N^{\epsilon B29}$-tetradecanoyl des(B30) human insulin,
$N^{\epsilon B29}$-decanoyl des(B30) human insulin,
$N^{\epsilon B29}$-dodecanoyl des(B30) human insulin,
$N^{\epsilon B29}$-tridecanoyl Gly$^{A21}$ des(B30) human insulin,
$N^{\epsilon B29}$-tetradecanoyl Gly$^{A21}$ des(B30) human insulin,
$N^{\epsilon B29}$-decanoyl Gly$^{A21}$ des(B30) human insulin,
$N^{\epsilon B29}$-dodecanoyl Gly$^{A21}$ des(B30) human insulin,
$N^{\epsilon B29}$-tridecanoyl Gly$^{A21}$ Gln$^{B3}$ des(B30) human insulin,
$N^{\epsilon B29}$-tetradecanoyl Gly$^{A21}$ Gln$^{B3}$ des(B30) human insulin,
$N^{\epsilon B29}$-decanoyl Gly$^{A21}$ Gln$^{B3}$ des(B30) human insulin,
$N^{\epsilon B29}$-dodecanoyl Gly$^{A21}$ Gln$^{B3}$ des(B30) human insulin,
$N^{\epsilon B29}$-tridecanoyl Ala$^{A21}$ des(B30) human insulin,
$N^{\epsilon B29}$-tetradecanoyl Ala$^{A21}$ des(B30) human insulin,
$N^{\epsilon B29}$-decanoyl Ala$^{A21}$ des(B30) human insulin,
$N^{\epsilon B29}$-dodecanoyl Ala$^{A21}$ des(B30) human insulin,
$N^{\epsilon B29}$-tridecanoyl Ala$^{A21}$ Gln$^{B3}$ des(B30) human insulin,
$N^{\epsilon B29}$-tetradecanoyl Ala$^{A21}$ Gln$^{B3}$ des(B30) human insulin,
$N^{\epsilon B29}$-decanoyl Ala$^{A21}$ Gln$^{B3}$ des(B30) human insulin,
$N^{\epsilon B29}$-dodecanoyl Ala$^{A21}$ Gln$^{B3}$ des(B30) human insulin,
$N^{\epsilon B29}$-tridecanoyl Gln$^{B3}$ des(B30) human insulin,
$N^{\epsilon B29}$-tetradecanoyl Gln$^{B3}$ des(B30) human insulin,
$N^{\epsilon B29}$-decanoyl Gln$^{B3}$ des(B30) human insulin,
$N^{\epsilon B29}$-dodecanoyl Gln$^{B3}$ des(B30) human insulin,
$N^{\epsilon B29}$-tridecanoyl Gly$^{A21}$ human insulin, $N^{\epsilon B29}$-tetradecanoyl $Gly^{A21}$ human insulin,
$N^{\epsilon B29}$-decanoyl $Gly^{A21}$ human insulin,
$N^{\epsilon B29}$-dodecanoyl $Gly^{A21}$ human insulin,
$N^{\epsilon B29}$-tridecanoyl $Gly^{A21}$ $Gln^{B3}$ human insulin,
$N^{\epsilon B29}$-tetradecanoyl $Gly^{A21}$ $Gln^{B3}$ human insulin,
$N^{\epsilon B29}$-decanoyl $Gly^{A21}$ $Gln^{B3}$ human insulin,
$N^{\epsilon B29}$-dodecanoyl $Gly^{A21}$ $Gln^{B3}$ human insulin,
$N^{\epsilon B29}$-tridecanoyl $Ala^{A21}$ human insulin,
$N^{\epsilon B29}$-tetradecanoyl $Ala^{A21}$ human insulin,
$N^{\epsilon B29}$-decanoyl $Ala^{A21}$ human insulin,
$N^{\epsilon B29}$-dodecanoyl $Ala^{A21}$ human insulin,
$N^{\epsilon B29}$-tridecanoyl $Ala^{A21}$ $Gln^{B3}$ human insulin,
$N^{\epsilon B29}$-tetradecanoyl $Ala^{A21}$ $Gln^{B3}$ human insulin,
$N^{\epsilon B29}$-decanoyl $Ala^{A21}$ $Gln^{B3}$ human insulin,
$N^{\epsilon B29}$-dodecanoyl $Ala^{A21}$ $Gln^{B3}$ human insulin,
$N^{\epsilon B29}$-tridecanoyl $Gln^{B3}$ human insulin,
$N^{\epsilon B29}$-tetradecanoyl $Gln^{B3}$ human insulin,
$N^{\epsilon B29}$-decanoyl $Gln^{B3}$ human insulin,
$N^{\epsilon B29}$-dodecanoyl $Gln^{B3}$ human insulin,
$N^{\epsilon B29}$-tridecanoyl $Glu^{B30}$ human insulin,
$N^{\epsilon B29}$-tetradecanoyl $Glu^{B30}$ human insulin,
$N^{\epsilon B29}$-decanoyl $Glu^{B30}$ human insulin,
$N^{\epsilon B29}$-dodecanoyl $Glu^{B30}$ human insulin,
$N^{\epsilon B29}$-tridecanoyl $Gly^{A21}$ $Glu^{B30}$ human insulin,
$N^{\epsilon B29}$-tetradecanoyl $Gly^{A21}$ $Glu^{B30}$ human insulin,
$N^{\epsilon B29}$-decanoyl $Gly^{A21}$ $Glu^{B30}$ human insulin,
$N^{\epsilon B29}$-dodecanoyl $Gly^{A21}$ $Glu^{B30}$ human insulin,
$N^{\epsilon B29}$-tridecanoyl $Gly^{A21}$ $Gln^{B3}$ $Glu^{B30}$ human insulin,
$N^{\epsilon B29}$-tetradecanoyl $Gly^{A21}$ $Gln^{B3}$ $Glu^{B30}$ human insulin,
$N^{\epsilon B29}$-decanoyl $Gly^{A21}$ 1 $Gln^{B3}$ $Glu^{B30}$ human insulin,
$N^{\epsilon B29}$-dodecanoyl $Gly^{A21}$ $Gln^{B3}$ $Glu^{B30}$ human insulin,
$N^{\epsilon B29}$-tridecanoyl $Ala^{A21}$ $Glu^{B30}$ human insulin,
$N^{\epsilon B29}$-tetradecanoyl $Ala^{A21}$ $Glu^{B30}$ human insulin,
$N^{\epsilon B29}$-decanoyl $Ala^{A21}$ $Glu^{B30}$ human insulin,
$N^{\epsilon B29}$-dodecanoyl $Ala^{A21}$ $Glu^{B30}$ human insulin,
$N^{\epsilon B29}$-tridecanoyl $Ala^{A21}$ $Gln^{B3}$ $Glu^{B30}$ human insulin,
$N^{\epsilon B29}$-tetradecanoyl $Ala^{A21}$ $Gln^{B3}$ $Glu^{B30}$ human insulin,
$N^{\epsilon B29}$-decanoyl $Ala^{A21}$ $Gln^{B3}$ $Glu^{B30}$ human insulin,
$N^{\epsilon B29}$-dodecanoyl $Ala^{A21}$ $Gln^{B3}$ $Glu^{B30}$ human insulin,
$N^{\epsilon B29}$-tridecanoyl $Gln^{B3}$ $Glu^{B30}$ human insulin,
$N^{\epsilon B29}$-tetradecanoyl $Gln^{B3}$ $Glu^{B30}$ human insulin,
$N^{\epsilon B29}$-decanoyl $Gln^{B3}$ $Glu^{B30}$ human insulin and
$N^{\epsilon B29}$-dodecanoyl $Gln^{B3}$ $Glu^{B30}$ human insulin.

Examples of preferred human insulin derivatives according to the present invention in which two $Zn^{2+}$ ions are bound per insulin hexamer are the following:

$(N^{\epsilon B29}$-tridecanoyl des(B30) human insulin$)_6$, $2Zn^{2+}$,
$(N^{\epsilon B29}$-tetradecanoyl des(B30) human insulin$)_6$, $2Zn^{2+}$,
$(N^{\epsilon B29}$-decanoyl des(B30) human insulin$)_6$, $2Zn^{2+}$,
$(N^{\epsilon B29}$-dodecanoyl des(B30) human insulin$)_6$, $2Zn^{2+}$,
$(N^{\epsilon B29}$-tridecanoyl $Gly^{A21}$ des(B30) human insulin$)_6$, $2Zn^{2+}$,
$(N^{\epsilon B29}$-tetradecanoyl $Gly^{A21}$ des(B30) human insulin$)_6$, $2Zn^{2+}$,
$(N^{\epsilon B29}$-decanoyl $Gly^{A21}$ des(B30) human insulin$)_6$, $2Zn^{2+}$,
$(N^{\epsilon B29}$-dodecanoyl $Gly^{A21}$ des(B30) human insulin$)_6$, $2Zn^{2+}$,
$(N^{\epsilon B29}$-tridecanoyl $Gly^{A21}$ $Gln^{B3}$ des(B30) human insulin$)_6$, $2Zn^{2+}$,
$(N^{\epsilon B29}$-tetradecanoyl $Gly^{A21}$ $Gln^{B3}$ des(B30) human insulin$)_6$, $2Zn^{2+}$,
$(N^{\epsilon B29}$-decanoyl $Gly^{A21}$ $Gln^{B3}$ des(B30) human insulin$)_6$, $2Zn^{2+}$,
$(N^{\epsilon B29}$-dodecanoyl $Gly^{A21}$ 1 $Gln^{B3}$ des(B30) human insulin$)_6$, $2Zn^{2+}$,
$(N^{\epsilon B29}$-tridecanoyl $Ala^{A21}$ des(B30) human insulin$)_6$, $2Zn^{2+}$,
$(N^{\epsilon B29}$-tetradecanoyl $Ala^{A21}$ des(B30) human insulin$)_6$, $2Zn^{2+}$,
$(N^{\epsilon B29}$-decanoyl $Ala^{A21}$ des(B30) human insulin$)_6$, $2Zn^{2+}$,
$(N^{\epsilon B29}$-dodecanoyl $Ala^{A21}$ des(B30) human insulin$)_6$, $2Zn^{2+}$,
$(N^{\epsilon B29}$-tridecanoyl $Ala^{A21}$ $Gln^{B3}$ des(B30) human insulin$)_6$, $2Zn^{2+}$,
$(N^{\epsilon B29}$-tetradecanoyl $Ala^{A21}$ $Gln^{B3}$ des(B30) human insulin$)_6$, $2Zn^{2+}$,
$(N^{\epsilon B29}$-decanoyl $Ala^{A21}$ $Gln^{B3}$ des(B30) human insulin$)_6$, $2Zn^{2+}$,
$(N^{\epsilon B29}$-dodecanoyl $Ala^{A21}$ $Gln^{B3}$ des(B30) human insulin$)_6$, $2Zn^{2+}$,
$(N^{\epsilon B29}$-tridecanoyl $Gln^{B3}$ des(B30) human insulin$)_6$, $2Zn^{2+}$,
$(N^{\epsilon B29}$-tetradecanoyl $Gln^{B3}$ des(B30) human insulin$)_6$, $2Zn^{2+}$,
$(N^{\epsilon B29}$-decanoyl $Gln^{B3}$ des(B30) human insulin$)_6$, $2Zn^{2+}$,
$(N^{\epsilon B29}$-dodecanoyl $Gln^{B3}$ des(B30) human insulin$)_6$, $2Zn^{2+}$,
$(N^{\epsilon B29}$-tridecanoyl human insulin$)_6$, $2Zn^{2+}$,
$(N^{\epsilon B29}$-tetradecanoyl human insulin$)_6$, $2Zn^{2+}$,
$(N^{\epsilon B29}$-decanoyl human insulin$)_6$, $2Zn^{2+}$,
$(N^{\epsilon B29}$-dodecanoyl human insulin$)_6$, $2Zn^{2+}$,
$(N^{\epsilon B29}$-tridecanoyl $Gly^{A21}$ human insulin$)_6$, $2Zn^{2+}$,
$(N^{\epsilon B29}$-tetradecanoyl $Gly^{A21}$ human insulin$)_6$, $2Zn^{2+}$,
$(N^{\epsilon B29}$-decanoyl $Gly^{A21}$ human insulin$)_6$, $2Zn^{2+}$,
$(N^{\epsilon B29}$-dodecanoyl $Gly^{A21}$ human insulin$)_6$, $2Zn^{2+}$,
$(N^{\epsilon B29}$-tridecanoyl $Gly^{A21}$ $Gln^{B3}$ human insulin$)_6$, $2Zn^{2+}$,
$(N^{\epsilon B29}$-tetradecanoyl $Gly^{A21}$ $Gln^{B3}$ human insulin$)_6$, $2Zn^{2+}$,
$(N^{\epsilon B29}$-decanoyl $Gly^{A21}$ $Gln^{B3}$ human insulin$)_6$, $2Zn^{2+}$,
$(N^{\epsilon B29}$-dodecanoyl $Gly^{A21}$ $Gln^{B3}$ human insulin$)_6$, $2Zn^{2+}$,
$(N^{\epsilon B29}$-tridecanoyl $Ala^{A21}$ human insulin$)_6$, $2Zn^{2+}$,
$(N^{\epsilon B29}$-tetradecanoyl $Ala^{A21}$ human insulin$)_6$, $2Zn^{2+}$,
$(N^{\epsilon B29}$-decanoyl $Ala^{A21}$ human insulin$)_6$, $2Zn^{2+}$,
$(N^{\epsilon B29}$-dodecanoyl $Ala^{A21}$ human insulin$)_6$, $2Zn^{2+}$,
$(N^{\epsilon B29}$-tridecanoyl $Ala^{A21}$ $Gln^{B3}$ human insulin$)_6$, $2Zn^{2+}$,
$(N^{\epsilon B29}$-tetradecanoyl $Ala^{A21}$ $Gln^{B3}$ human insulin$)_6$, $2Zn^{2+}$,
$(N^{\epsilon B29}$-decanoyl $Ala^{A21}$ $Gln^{B3}$ human insulin$)_6$, $2Zn^{2+}$,
$(N^{\epsilon B29}$-dodecanoyl $Ala^{A21}$ $Gln^{B3}$ human insulin$)_6$, $2Zn^{2+}$,
$(N^{\epsilon B29}$-tridecanoyl $Gln^{B3}$ human insulin$)_6$, $2Zn^{2+}$,
$(N^{\epsilon B29}$-tetradecanoyl $Gln^{B3}$ human insulin$)_6$, $2Zn^{2+}$,
$(N^{\epsilon B29}$-decanoyl $Gln^{B3}$ human insulin$)_6$, $2Zn^{2+}$,
$(N^{\epsilon B29}$-dodecanoyl $Gln^{B3}$ human insulin$)_6$, $2Zn^{2+}$,
$(N^{\epsilon B29}$-tridecanoyl $Gln^{B3}$ human insulin$)_6$, $2Zn^{2+}$,
$(N^{\epsilon B29}$-tetradecanoyl $Glu^{B30}$ human insulin$)_6$, $2Zn^{2+}$,
$(N^{\epsilon B29}$-decanoyl $Glu^{B30}$ human insulin$)_6$, $2Zn^{2+}$, ($N^{\epsilon B29}$-dodecanoyl Glu$^{B30}$ human insulin)$_6$, 2Zn$^{2+}$,
($N^{\epsilon B29}$-tridecanoyl Gly$^{A21}$ Glu$^{B30}$ human insulin)$_6$, 2Zn$^{2+}$,
($N^{\epsilon B29}$-tetradecanoyl Gly$^{A21}$ Glu$^{B30}$ human insulin)$_6$, 2Zn$^{2+}$,
($N^{\epsilon B29}$-decanoyl Gly$^{A21}$ Glu$^{B30}$ human insulin)$_6$, 2Zn$^{2+}$,
($N^{\epsilon B29}$-dodecanoyl Gly$^{A21}$ Glu$^{B30}$ human insulin)$_6$, 2Zn$^{2+}$,
($N^{\epsilon B29}$-tridecanoyl Gly$^{A21}$ Gln$^{B3}$ Glu$^{B30}$ human insulin)$_6$, 2Zn$^{2+}$,
($N^{\epsilon B29}$-tetradecanoyl Gly$^{A21}$ Gln$^{B3}$ Glu$^{B30}$ human insulin)$_6$, 2Zn$^{2+}$,
($N^{\epsilon B29}$-decanoyl Gly$^{A21}$ Gln$^{B3}$ Glu$^{B30}$ human insulin)$_6$, 2Zn$^{2+}$,
($N^{\epsilon B29}$-dodecanoyl Gly$^{A21}$ Gln$^{B3}$ Glu$^{B30}$ human insulin)$_6$, 2Zn$^{2+}$,
($N^{\epsilon B29}$-tridecanoyl Ala$^{A21}$ Glu$^{B30}$ human insulin)$_6$, 2Zn$^{2+}$,
($N^{\epsilon B29}$-tetradecanoyl Gly$^{A21}$ Glu$^{B30}$ human insulin)$_6$, 2Zn$^{2+}$,
($N^{\epsilon B29}$-decanoyl Ala$^{A21}$ Glu$^{B30}$ human insulin)$_6$, 2Zn$^{2+}$,
($N^{\epsilon B29}$-dodecanoyl Ala$^{A21}$ Glu$^{B30}$ human insulin)$_6$, 2Zn$^{2+}$,
($N^{\epsilon B29}$-tridecanoyl Ala$^{A21}$ Gln$^{B3}$ Glu$^{B30}$ human insulin)$_6$, 2Zn$^{2+}$,
($N^{\epsilon B29}$-tetradecanoyl Ala$^{A21}$ Gln$^{B3}$ Glu$^{B30}$ human insulin)$_6$, 2Zn$^{2+}$,
($N^{\epsilon B29}$-decanoyl Ala$^{A21}$ Gln$^{B3}$ Glu$^{B30}$ human insulin)$_6$, 2Zn$^{2+}$,
($N^{\epsilon B29}$-dodecanoyl Ala$^{A21}$ Gln$^{B3}$ Glu$^{B30}$ human insulin)$_6$, 2Zn$^{2+}$,
($N^{\epsilon B29}$-tridecanoyl Ala$^{A21}$ Gln$^{B3}$ Glu$^{B30}$ human insulin)$_6$, 2Zn$^{2+}$,
($N^{\epsilon B29}$-tetradecanoyl Gln$^{B3}$ Glu$^{B30}$ human insulin)$_6$, 2Zn$^{2+}$,
($N^{\epsilon B29}$-decanoyl Gln$^{B3}$ Glu$^{B30}$ human insulin)$_6$, 2Zn$^{2+}$ and
($N^{\epsilon B29}$-dodecanoyl Gln$^{B3}$ Glu$^{B30}$ human insulin)$_6$, 2Zn$^{2+}$.

Examples of preferred human insulin derivatives according to the present invention in which three Zn$^{2+}$ ions are bound per insulin hexamer are the following:

($N^{\epsilon B29}$-tridecanoyl des(B30) human insulin)$_6$, 3Zn$^{2+}$,
($N^{\epsilon B29}$-tetradecanoyl des(B30) human insulin)$_6$, 3Zn$^{2+}$,
($N^{\epsilon B29}$-decanoyl des(B30) human insulin)$_6$, 3Zn$^{2+}$,
($N^{\epsilon B29}$-dodecanoyl des(B30) human insulin)$_6$, 3Zn$^{2+}$,
($N^{\epsilon B29}$-tridecanoyl Gly$^{A21}$ des(B30) human insulin)$_6$, 3Zn$^{2+}$,
($N^{\epsilon B29}$-tetradecanoyl Gly$^{A21}$ des(B30) human insulin)$_6$, 3Zn$^{2+}$,
($N^{\epsilon B29}$-decanoyl Gly$^{A21}$ des(B30) human insulin)$_6$, 3Zn$^{2+}$,
($N^{\epsilon B29}$-dodecanoyl Gly$^{A21}$ des(B30) human insulin)$_6$, 3Zn$^{2+}$,
($N^{\epsilon B29}$-tridecanoyl Gly$^{A21}$ Gln$^{B3}$ des(B30) human insulin)$_6$, 3Zn$^{2+}$,
($N^{\epsilon B29}$-tetradecanoyl Gly$^{A21}$ Gln$^{B3}$ des(B30) human insulin)$_6$, 3Zn$^{2+}$,
($N^{\epsilon B29}$-decanoyl Gly$^{A21}$ Gln$^{B3}$ des(B30) human insulin)$_6$, 3Zn$^{2+}$,
($N^{\epsilon B29}$-dodecanoyl Gly$^{A21}$ Gln$^{B3}$ des(B30) human insulin)$_6$, 3Zn$^{2+}$,
($N^{\epsilon B29}$-tridecanoyl Ala$^{A21}$ des(B30) human insulin)$_6$, 3Zn$^{2+}$,
($N^{\epsilon B29}$-tetradecanoyl Ala$^{A21}$ des(B30) human insulin)$_6$, 3Zn$^{2+}$,
($N^{\epsilon B29}$-decanoyl Ala$^{A21}$ des(B30) human insulin)$_6$, 3Zn$^{2+}$,
($N^{\epsilon B29}$-dodecanoyl Ala$^{A21}$ des(B30) human insulin)$_6$, 3Zn$^{2+}$,
($N^{\epsilon B29}$-tridecanoyl Ala$^{A21}$ Gln$^{B3}$ des(B30) human insulin)$_6$, 3Zn$^{2+}$,
($N^{\epsilon B29}$-tetradecanoyl Ala$^{A21}$ Gln$^{B3}$ des(B30) human insulin)$_6$, 3Zn$^{2+}$,
($N^{\epsilon B29}$-decanoyl Ala$^{A21}$ Gln$^{B3}$ des(B30) human insulin)$_6$, 3Zn$^{2+}$,
($N^{\epsilon B29}$-dodecanoyl Ala$^{A21}$ Gln$^{B3}$ des(B30) human insulin)$_6$, 3Zn$^{2+}$,
($N^{\epsilon B29}$-tridecanoyl Gln$^{B3}$ des(B30) human insulin)$_6$, 3Zn$^{2+}$,
($N^{\epsilon B29}$-tetradecanoyl Gln$^{B3}$ des(B30) human insulin)$_6$, 3Zn$^{2+}$,
($N^{\epsilon B29}$-decanoyl Gln$^{B3}$ des(B30) human insulin)$_6$, 3Zn$^{2+}$,
($N^{\epsilon B29}$-dodecanoyl Gln$^{B3}$ des(B30) human insulin)$_6$, 3Zn$^{2+}$,
($N^{\epsilon B29}$-tridecanoyl human insulin)$_6$, 3Zn$^{2+}$,
($N^{\epsilon B29}$-tetradecanoyl human insulin)$_6$, 3Zn$^{2+}$,
($N^{\epsilon B29}$-decanoyl human insulin)$_6$, 3Zn$^{2+}$,
($N^{\epsilon B29}$-dodecanoyl human insulin)$_6$, 3Zn$^{2+}$,
($N^{\epsilon B29}$-tridecanoyl Gly$^{A21}$ human insulin)$_6$, 3Zn$^{2+}$,
($N^{\epsilon B29}$-tetradecanoyl Gly$^{A21}$ human insulin)$_6$, 3Zn$^{2+}$,
($N^{\epsilon B29}$-decanoyl Gly$^{A21}$ human insulin)$_6$, 3Zn$^{2+}$,
($N^{\epsilon B29}$-dodecanoyl Gly$^{A21}$ human insulin)$_6$, 3Zn$^{2+}$,
($N^{\epsilon B29}$-tridecanoyl Gly$^{A21}$ Gln$^{B3}$ human insulin)$_6$, 3Zn$^{2+}$,
($N^{\epsilon B29}$-tetradecanoyl Gly$^{A21}$ Gln$^{B3}$ human insulin)$_6$, 3Zn$^{2+}$,
($N^{\epsilon B29}$-decanoyl Gly$^{A21}$ Gln$^{B3}$ human insulin)$_6$, 3Zn$^{2+}$,
($N^{\epsilon B29}$-dodecanoyl Gly$^{A21}$ Gln$^{B3}$ human insulin)$_6$, 3Zn$^{2+}$,
($N^{\epsilon B29}$-tridecanoyl Ala$^{A21}$ human insulin)$_6$, 3Zn$^{2+}$,
($N^{\epsilon B29}$-tetradecanoyl Ala$^{A21}$ human insulin)$_6$, 3Zn$^{2+}$,
($N^{\epsilon B29}$-decanoyl Ala$^{A21}$ human insulin)$_6$, 3Zn$^{2+}$,
($N^{\epsilon B29}$-dodecanoyl Ala$^{A21}$ human insulin)$_6$, 3Zn$^{2+}$,
($N^{\epsilon B29}$-tridecanoyl Ala$^{A21}$ Gln$^{B3}$ human insulin)$_6$, 3Zn$^{1+}$,
($N^{\epsilon B29}$-tetradecanoyl Ala$^{A21}$ Gln$^{B3}$ human insulin)$_6$, 3Zn$^{2+}$,
($N^{\epsilon B29}$-decanoyl Ala$^{A21}$ Gln$^{B3}$ human insulin)$_6$, 3Zn$^{2+}$,
($N^{\epsilon B29}$-dodecanoyl Ala$^{A21}$ Gln$^{B3}$ human insulin)$_6$, 3Zn$^{2+}$,
($N^{\epsilon B29}$-tridecanoyl Gln$^{B3}$ human insulin)$_6$, 3Zn$^{2+}$,
($N^{\epsilon B29}$-tetradecanoyl Gln$^{B3}$ human insulin)$_6$, 3Zn$^{2+}$,
($N^{\epsilon B29}$-decanoyl Gln$^{B3}$ human insulin)$_6$, 3Zn$^{2+}$,
($N^{\epsilon B29}$-dodecanoyl Gln$^{B3}$ human insulin)$_6$, 3Zn$^{2+}$,
($N^{\epsilon B29}$-tridecanoyl Glu$^{B30}$ human insulin)$_6$, 3Zn$^{2+}$,
($N^{\epsilon B29}$-tetradecanoyl Glu$^{B30}$ human insulin)$_6$, 3Zn$^{2+}$,
($N^{\epsilon B29}$-decanoyl Glu$^{B30}$ human insulin)$_6$, 3Zn$^{2+}$,
($N^{\epsilon B29}$-dodecanoyl Glu$^{B30}$ human insulin)$_6$, 3Zn$^{2+}$,
($N^{\epsilon B29}$-tridecanoyl Gly$^{A21}$ Glu$^{B30}$ human insulin)$_6$, 3Zn$^{2+}$,
($N^{\epsilon B29}$-tetradecanoyl Gly$^{A21}$ Glu$^{B30}$ human insulin)$_6$, 3Zn$^{2+}$,
($N^{\epsilon B29}$-decanoyl Gly$^{A21}$ Glu$^{B30}$ human insulin)$_6$, 3Zn$^{2+}$,
($N^{\epsilon B29}$-dodecanoyl Gly$^{A21}$ Glu$^{B30}$ human insulin)$_6$, 3Zn$^{2+}$,
($N^{\epsilon B29}$-tridecanoyl Gly$^{A21}$ Glu$^{B30}$ human insulin)$_6$, 3Zn$^{2+}$, ($N^{\epsilon B29}$-tetradecanoyl Gly$^{A21}$ Gln$^{B3}$ Glu$^{B30}$ human insulin)$_6$, 3Zn$^{2+}$,
($N^{\epsilon B29}$-decanoyl Gly$^{A21}$ Gln$^{B3}$ Glu$^{B30}$ human insulin)$_6$, 3Zn$^{2+}$,
($N^{\epsilon B29}$-dodecanoyl Gly$^{A21}$ Gln$^{B3}$ Glu$^{B30}$ human insulin)$_6$, 3Zn$^{2+}$,
($N^{\epsilon B29}$-tridecanoyl Ala$^{A21}$ Glu$^{B30}$ human insulin)$_6$, 3Zn$^{2+}$,
($N^{\epsilon B29}$-tetradecanoyl Ala$^{A21}$ Glu$^{B30}$ human insulin)$_6$, 3Zn$^{2+}$,
($N^{\epsilon B29}$-decanoyl Ala$^{A21}$ Glu$^{B30}$ human insulin)$_6$, 3Zn$^{2+}$,
($N^{\epsilon B29}$-dodecanoyl Ala$^{A21}$ Glu$^{B30}$ human insulin)$_6$, 3Zn$^{2+}$,
($N^{\epsilon B29}$-tridecanoyl Ala$^{A21}$ Gln$^{B3}$ Glu$^{B30}$ human insulin)$_6$, 3Zn$^{2+}$,
($N^{\epsilon B29}$-tetradecanoyl Ala$^{A21}$ Gln$^{B3}$ Glu$^{B30}$ human insulin)$_6$, 3Zn$^{2+}$,
($N^{\epsilon B29}$-decanoyl Ala$^{A21}$ Gln$^{B3}$ Glu$^{B30}$ human insulin)$_6$, 3Zn$^{2+}$,
($N^{\epsilon B29}$-dodecanoyl Ala$^{A21}$ Gln$^{B3}$ Glu$^{B30}$ human insulin)$_6$, 3Zn$^{2+}$,
($N^{\epsilon B29}$-tridecanoyl Gln$^{B3}$ Glu$^{B30}$ human insulin)$_6$, 3Z$^{2+}$,
($N^{\epsilon B29}$-tetradecanoyl Gln$^{B3}$ Glu$^{B30}$ human insulin)$_6$, 3Zn$^{2+}$,
($N^{\epsilon B29}$-decanoyl Gln$^{B3}$ Glu$^{B30}$ human insulin)$_6$, 3Zn$^{2+}$ and
($N^{\epsilon B29}$-dodecanoyl Gln$^{B3}$ Glu$^{B30}$ human insulin)$_6$, 3Zn$^{2+}$.

Examples of preferred human insulin derivatives according to the present invention in which four Zn$^{2+}$ ions are bound per insulin hexamer are the following:

($N^{\epsilon B29}$-tridecanoyl des(B30) human insulin)$_6$, 4Zn$^{2+}$,
($N^{\epsilon B29}$-tetradecanoyl des(B30) human insulin)$_6$, 4Zn$^{2+}$,
($N^{\epsilon B29}$-decanoyl des(B30) human insulin)$_6$, 4Zn$^{2+}$,
($N^{\epsilon B29}$-dodecanoyl des(B30) human insulin)$_6$, 4Zn$^{2+}$,
($N^{\epsilon B29}$-tridecanoyl Gly$^{A21}$ des(B30) human insulin)$_6$, 4Zn$^{2+}$,
($N^{\epsilon B29}$-tetradecanoyl Gly$^{A21}$ des(B30) human insulin)$_6$, 4Zn$^{2+}$,
($N^{\epsilon B29}$-decanoyl Gly$^{A21}$ des(B30) human insulin)$_6$, 4Zn$^{2+}$,
($N^{\epsilon B29}$-dodecanoyl Gly$^{A21}$ des(B30) human insulin)$_6$, 4Zn$^{2+}$,
($N^{\epsilon B29}$-tridecanoyl Ala$^{A21}$ Gln$^{B3}$ des(B30) human insulin)$_6$, 4Zn$^{2+}$,
($N^{\epsilon B29}$-tetradecanoyl Gly$^{A21}$ Gln$^{B3}$ des(B30) human insulin)$_6$, 4Zn$^{2+}$,
($N^{\epsilon B29}$-decanoyl Gly$^{A21}$ Gln$^{B3}$ des(B30) human insulin)$_6$, 4Zn$^{2+}$,
($N^{\epsilon B29}$-dodecanoyl Gly$^{A21}$ Gln$^{B3}$ des(B30) human insulin)$_6$, 4Zn$^{2+}$,
($N^{\epsilon B29}$-tridecanoyl Ala$^{A21}$ des(B30) human insulin)$_6$, 4Zn$^{2+}$,
($N^{\epsilon B29}$-tetradecanoyl Ala$^{A21}$ des(B30) human insulin)$_6$, 4Zn$^{2+}$,
($N^{\epsilon B29}$-decanoyl Ala$^{A21}$ des(B30) human insulin)$_6$, 4Zn$^{2+}$,
($N^{\epsilon B29}$-dodecanoyl Ala$^{A21}$ des(B30) human insulin)$_6$, 4Zn$^{2+}$,
($N^{\epsilon B29}$-tridecanoyl Ala$^{A21}$ Gln$^{B3}$ des(B30) human insulin)$_6$, 4Zn$^{2+}$,
($N^{\epsilon B29}$-tetradecanoyl Ala$^{A21}$ Gln$^{B3}$ des(B30) human insulin)$_6$, 4Zn$^{2+}$,
($N^{\epsilon B29}$-decanoyl Ala$^{A21}$ Gln$^{B3}$ des(B30) human insulin)$_6$, 4Zn$^{2+}$,
($N^{\epsilon B29}$-dodecanoyl Ala$^{A21}$ Gln$^{B3}$ des(B30) human insulin)$_6$, 4Zn$^{2+}$,
($N^{\epsilon B29}$-tridecanoyl Gln$^{B3}$ des(B30) human insulin)$_6$, 4Zn$^{2+}$,
($N^{\epsilon B29}$-tetradecanoyl Gln$^{B3}$ des(B30) human insulin)$_6$, 4Zn$^{2+}$,
($N^{\epsilon B29}$-decanoyl Gln$^{B3}$ des(B30) human insulin)$_6$, 4Zn$^{2+}$,
($N^{\epsilon B29}$-dodecanoyl Gln$^{B3}$ des(B30) human insulin)$_6$, 4Zn$^{2+}$,
($N^{\epsilon B29}$-tridecanoyl human insulin)$_6$, 4Zn$^{2+}$,
($N^{\epsilon B29}$-tetradecanoyl human insulin)$_6$, 4Zn$^{2+}$,
($N^{\epsilon B29}$-decanoyl human insulin)$_6$, 4Zn$^{2+}$,
($N^{\epsilon B29}$-dodecanoyl human insulin)$_6$, 4Zn$^{2+}$,
($N^{\epsilon B29}$-tridecanoyl Gly$^{A21}$ human insulin)$_6$, 4Zn$^{2+}$,
($N^{\epsilon B29}$-tetradecanoyl Gly$^{A21}$ human insulin)$_6$, 4Zn$^{2+}$,
($N^{\epsilon B29}$-decanoyl Gly$^{A21}$ human insulin)$_6$, 4Zn$^{2+}$,
($N^{\epsilon B29}$-dodecanoyl Gly$^{A21}$ human insulin)$_6$, 4Zn$^{2+}$,
($N^{\epsilon B29}$-tridecanoyl Gly$^{A21}$ Gln$^{B3}$ human insulin)$_6$, 4Zn$^{2+}$,
($N^{\epsilon B29}$-tetradecanoyl Gly$^{A21}$ Gln$^{B3}$ human insulin)$_6$, 4Zn$^{2+}$,
($N^{\epsilon B29}$-decanoyl Gly$^{A21}$ Gln$^{B3}$ human insulin)$_6$, 4Zn$^{2+}$,
($N^{\epsilon B29}$-dodecanoyl Gly$^{A21}$ Gln$^{B3}$ human insulin)$_6$, 4Zn$^{2+}$,
($N^{\epsilon B29}$-tridecanoyl Ala$^{A21}$ human insulin)$_6$, 4Zn$^{2+}$,
($N^{\epsilon B29}$-tetradecanoyl Ala$^{A21}$ human insulin)$_6$, 4Zn$^{2+}$,
($N^{\epsilon B29}$-decanoyl Ala$^{A21}$ human insulin)$_6$, 4Zn$^{2+}$,
($N^{\epsilon B29}$-dodecanoyl Ala$^{A21}$ human insulin)$_6$, 4Zn$^{2+}$,
($N^{\epsilon B29}$-tridecanoyl Ala$^{A21}$ Gln$^{B3}$ human insulin)$_6$, 4Zn$^{2+}$,
($N^{\epsilon B29}$-tetradecanoyl Ala$^{A21}$ Gln$^{B3}$ human insulin)$_6$, 4Zn$^{2+}$,
($N^{\epsilon B29}$-decanoyl Ala$^{A21}$ Gln$^{B3}$ human insulin)$_6$, 4Zn$^{2+}$,
($N^{\epsilon B29}$-dodecanoyl Ala$^{A21}$ Gln$^{B3}$ human insulin)$_6$, 4Zn$^{2+}$,
($N^{\epsilon B29}$-tridecanoyl Gln$^{B3}$ human insulin)$_6$, 4Zn$^{2+}$,
($N^{\epsilon B29}$-tetradecanoyl Gln$^{B3}$ human insulin)$_6$, 4Zn$^{2+}$,
($N^{\epsilon B29}$-decanoyl Gln$^{B3}$ human insulin)$_6$, 4Zn$^{2+}$,
($N^{\epsilon B29}$-dodecanoyl Gln$^{B3}$ human insulin)$_6$, 4Zn$^{2+}$,
($N^{\epsilon B29}$-tridecanoyl Glu$^{B30}$ human insulin)$_6$, 4Zn$^{2+}$,
($N^{\epsilon B29}$-tetradecanoyl Glu$^{B30}$ human insulin)$_6$, 4Zn$^{2+}$,
($N^{\epsilon B29}$-decanoyl Glu$^{B30}$ human insulin)$_6$, 4Zn$^{2+}$,
($N^{\epsilon B29}$-dodecanoyl Glu$^{B30}$ human insulin)$_6$, 4Zn$^{2+}$,
($N^{\epsilon B29}$-tridecanoyl Gly$^{A21}$ Glu$^{B30}$ human insulin)$_6$, 4Zn$^{2+}$,
($N^{\epsilon B29}$-tetradecanoyl Gly$^{A21}$ Glu$^{B30}$ human insulin)$_6$, 4Zn$^{2+}$,
($N^{\epsilon B29}$-decanoyl Gly$^{A21}$ Glu$^{B30}$ human insulin)$_6$, 4Zn$^{2+}$,
($N^{\epsilon B29}$-dodecanoyl Gly$^{A21}$ Glu$^{B30}$ human insulin)$_6$, 4Zn$^{2+}$,
($N^{\epsilon B29}$-tridecanoyl Gly$^{A21}$ Gln$^{B3}$ Glu$^{B30}$ human insulin)$_6$, 4Zn$^{2+}$,
($N^{\epsilon B29}$-tetradecanoyl Gly$^{A21}$ Gln$^{B3}$ Glu$^{B30}$ human insulin)$_6$, 4Zn$^{2+}$,
($N^{\epsilon B29}$-decanoyl Gly$^{A21}$ Gln$^{B3}$ Glu$^{B30}$ human insulin)$_6$, 4Zn$^{2+}$,
($N^{\epsilon B29}$-dodecanoyl Gly$^{A21}$ Gln$^{B3}$ Glu$^{B30}$ human insulin)$_6$, 4Zn$^{2+}$,
($N^{\epsilon B29}$-tridecanoyl Ala$^{A21}$ Glu$^{B30}$ human insulin)$_6$, 4Zn$^{2+}$,
($N^{\epsilon B29}$-tetradecanoyl Ala$^{A21}$ Glu$^{B30}$ human insulin)$_6$, 4Zn$^{2+}$,
($N^{\epsilon B29}$-decanoyl Ala$^{A21}$ Glu$^{B30}$ human insulin)$_6$, 4Zn$^{2+}$,
($N^{\epsilon B29}$-dodecanoyl Ala$^{A21}$ Glu$^{B30}$ human insulin)$_6$, 4Zn$^{2+}$, ($N^{\epsilon B29}$-tridecanoyl Ala$^{A21}$ Gln$^{B3}$ Glu$^{B30}$ human insulin)$_6$, 4Zn$^{2+}$, ($N^{\epsilon B29}$-tetradecanoyl Ala$^{A21}$ Gln$^{B3}$ Glu$^{B30}$ human insulin)$_6$, 4Zn$^{2+}$, ($N^{\epsilon B29}$-decanoyl Ala$^{A21}$ Gln$^{B3}$ Glu$^{B30}$ human insulin)$_6$, 4Zn$^{2+}$, ($N^{\epsilon B29}$-dodecanoyl Ala$^{A21}$ Gln$^{B3}$ Glu$^{B30}$ human insulin)$_6$, 4Zn$^{2+}$, ($N^{\epsilon B29}$-tridecanoyl Gln$^{B3}$ Glu$^{B30}$ human insulin)$_6$, 4Zn$^{2+}$, ($N^{\epsilon B29}$-tetradecanoyl Gln$^{B3}$ Glu$^{B30}$ human insulin)$_6$, 4Zn$^{2+}$, ($N^{\epsilon B29}$-decanoyl Gln$^{B3}$ Glu$^{B30}$ human insulin)$_6$, 4Zn$^{2+}$ and ($N^{\epsilon B29}$-dodecanoyl Gln$^{B3}$ Glu$^{B30}$ human insulin)$_6$, 4Zn$^{2+}$.

BRIEF DESCRIPTION OF THE DRAWINGS

The present invention is further illustrated with reference to the appended drawings wherein.

DETAILED DESCRIPTION OF THE INVENTION

Terminology

Figure 1:
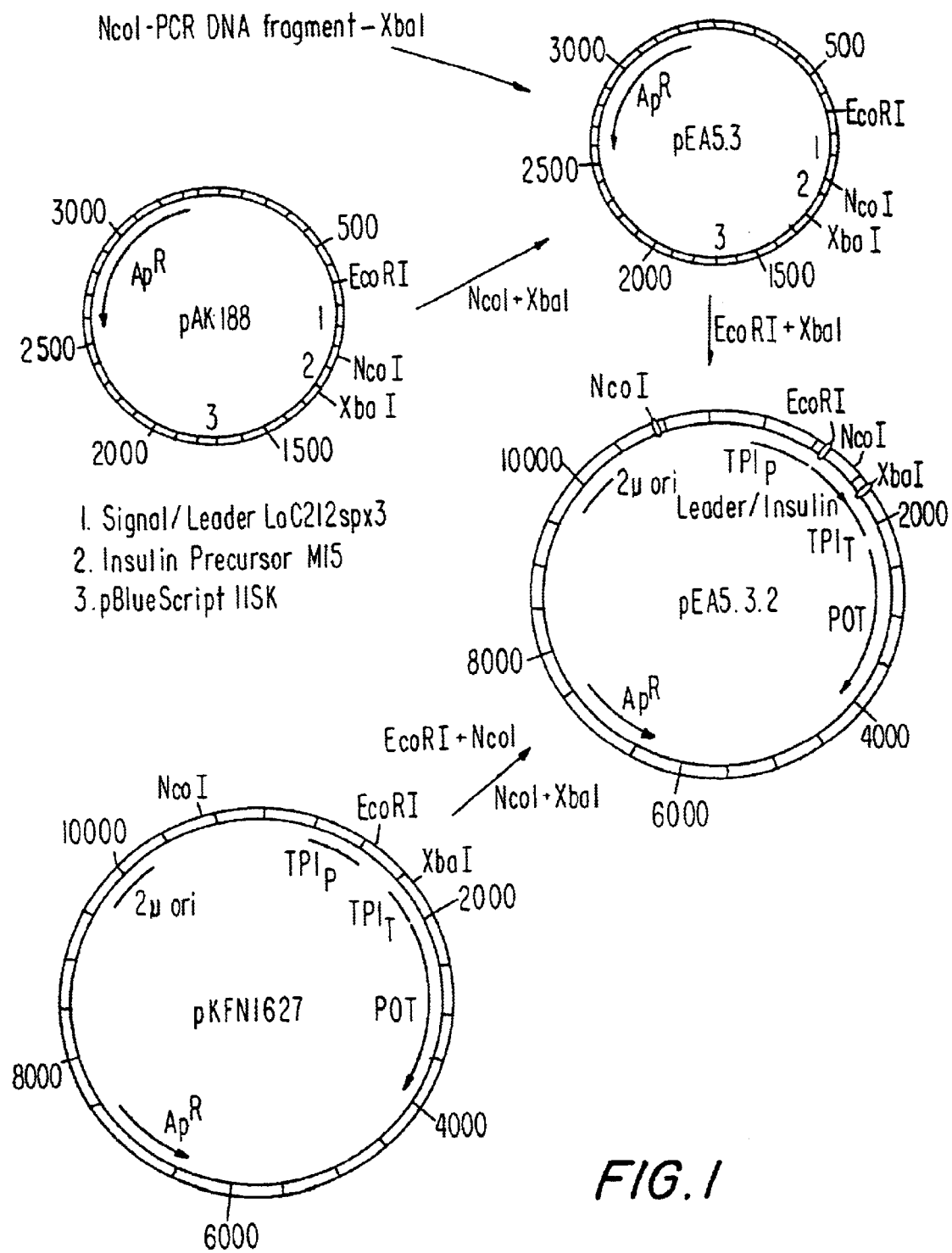
FIG. 1 shows the construction of the plasmid pEA5.3.2.

The three letter codes and one letter codes for the amino acid residues used herein are those stated in J. Biol. Chem. 243, p. 3558 (1968).

In the DNA sequences, A is adenine, C is cytosine, G is guanine, and T is thynine.

The following acronyms are used: DMSO for dimethyl sulphoxide, DMF for dimethylformamide, Boc for tert-butoxycarbonyl, RP-HPLC for reversed phase high performance liquid chromatography, X-OSu is an N-hydroxysuccinimid ester, X is an acyl group, and TFA for trifluoroacetic acid.

Preparation of Lipophilic Insulin Derivatives

The insulin derivatives according to the present invention can be prepared i.a. as described in the following:

1. Insulin Derivatives Featuring in Position B30 an Amino Acid Residue which can be Coded for by the Genetic Code. e.g. Threonine (Human Insulin) or Alanine (Porcine Insulin)

1.1 Starting from Human Insulin.

Human insulin is treated with a Boc-reagent (e.g. di-tert-butyl dicarbonate) to form (A1,B1)-diBoc human insulin, i.e., human insulin in which the N-terminal end of both chains are protected by a Boc-group. After an optional purification, e.g. by HPLC, an acyl group is introduced in the $\epsilon$-amino group of Lys$^{B29}$ by allowing the product to react with a N-hydroxysuccinimide ester of the formula X-OSu wherein X is the acyl group to be introduced. In the final step, TFA is used to remove the Boc-groups and the product, $N^{\epsilon B29}$-X human insulin, is isolated.

1.2 Starting from a Single Chain Insulin Precursor.

A single chain insulin precursor, extended in position B1 with an extension (Ext) which is connected to B1 via an arginine residue and in which the bridge from B30 to A1 is an arginine residue, i.e. a compound of the general formula Ext-Arg-B(1–30)-Arg-A(1–21), can be used as starting material. Acylation of this starting material with a N-hydroxysuccinimide ester of the general formula X-OSu wherein X is an acyl group, introduces the acyl group X in the $\epsilon$-amino group of Lys$^{B29}$ and in the N-terminal amino group of the precursor. On treating this acylated precursor of the formula ($N^{\epsilon B29}$-X), X-Ext-Arg-B(1–30)-Arg-A(1–21) with trypsin in a mixture of water and a suitable water-miscible organic solvent, e.g. DMF, DMSO or a lower alcohol, an intermediate of the formula ($N^{\epsilon B29}$-X), Arg$^{B31}$ insulin is obtained. Treating this intermediate with carboxypeptidase B yields the desired product, ($N^{\epsilon B29}$-X) insulin.

2. Insulin Derivatives with no Amino Acid Residue in Position B30, i.e. des(B30) Insulins 2.1 Starting from Human Insulin or Porcine Insulin.

On treatment with carboxypeptidase A in ammonium buffer, human insulin and porcine insulin both yield des (B30) insulin. After an optional purification, the des(B30) insulin is treated with a Boc-reagent (e.g. di-tert-butyl dicarbonate) to form (A1,B1)diBoc des(B30) insulin, i.e., des(B30) insulin in which the N-terminal end of both chains are protected by a Boc-group. After an optional purification, e.g. by HPLC, an acyl group is introduced in the $\epsilon$-amino group of Lys$^{B29}$ by allowing the product to react with a N-hydroxysuccinimide ester of the formula X-OSu wherein X is the acyl group to be introduced. In the final step, TFA is used to remove the Boc-groups and the product, ($N^{\epsilon B29}$-X) des(B30) insulin, is isolated.

2.2 Starting from a Single Chain Human Insulin Precursor.

A single chain human insulin precursor, which is extended in position B1 with an extension (Ext) which is connected to B1 via an arginine residue and which has a bridge from B30 to A1 can be a useful starting material. Preferably, the bridge is a peptide of the formula Y$_n$-Arg, where Y is a codable amino acid except lysine and arginine, and n is zero or an integer between 1 and 35. When n≧1, the Y's may designate different amino acids. Preferred examples of the bridge from B30 to A1 are: AlaAlaArg, SerArg, SerAspAspAlaArg and Arg (European Patent No. 163529). Treatment of such a precursor of the general formula Ext-Arg-B(1–30)-Y$_n$-Arg-A(1–21) with a lysyl endopeptidase, e.g. Achromobacter lyticus protease, yields Ext-Arg-B (1–29) Thr-Y$_n$-Arg-A(1–21) des(B30) insulin. Acylation of this intermediate with a N-hydroxysuccinimide ester of the general formula X-OSu wherein X is an acyl group, introduces the acyl group X in the $\epsilon$-amino group of Lys$^{B29}$, and in the N-terminal amino group of the A-chain and the B-chain to give ($N^{\epsilon B29}$-X) X-Ext-Arg-B(1–29) X-Thr-Y$_n$-Arg-A(1–21) des(B30) insulin. This intermediate on treatment with trypsin in mixture of water and a suitable organic solvent, e.g. DMF, DMSO or a lower alcohol, gives the desired derivative, ($N^{\epsilon B29}$-X) des(B30) human insulin.

Data on $N^{\epsilon B29}$ Modified Insulins.

Certain experimental data on $N^{\epsilon B29}$ modified insulins are given in Table 1.

The lipophilicity of an insulin derivative relative to human insulin, k'$_{rel}$, was measured on a LiChrosorb RP18 (5 μm, 250×4 mm) HPLC column by isocratic elution at 40° C. using mixtures of A) 0.1 M sodium phosphate buffer, pH 7.3, containing 10% acetonitrile, and B) 50% acetonitrile in water as eluents. The elution was monitored by following the UV absorption of the eluate at 214 nm. Void time, t$_0$, was found by injecting 0.1 mM sodium nitrate. Retention time for human insulin, t$_{human}$, was adjusted to at least 2t$_0$ by varying the ratio between the A and B solutions. k'$_{rel}$= (t$_{derivative}$-t$_0$)/(t$_{human}$-t$_0$).

The degree of prolongation of the blood glucose lowering effect was studied in rabbits. Each insulin derivative was tested by subcutaneous injection of 12 nmol thereof in, each of six rabbits in the single day retardation test. Blood sampling for glucose analysis was performed before injection and at 1, 2, 4 and 6 hours after injection. The glucose values found are expressed as percent of initial values. The Index of Protraction, which was calculated from the blood glucose values, is the scaled Index of Protraction (prolongation), see p. 211 in Markussen et al., Protein Engineering 1 (1987) 205–213. The formula has been scaled to render a value of 100 with bovine ultralente insulin and a value of 0 with Actrapid® insulin (Novo Nordisk A/S, 2880 Bagsvaerd, Denmark).

The insulin derivatives listed in Table 1 were administered in solutions containing 3 $Zn^{2+}$ per insulin hexamer, except those specifically indicated to be Zn-free.

For the very protracted analogues the rabbit model is inadequate because the decrease in blood glucose from initial is too small to estimate the index of protraction. The prolongation of such analogues is better characterized by the disappearance rate in pigs. $T_{50\%}$ is the time when 50% of the A14 $Tyr(^{125}I)$ analogue has disappeared from the site of injection as measured with an external γ-counter (Ribel, U et al., The Pig as a Model for Subcutaneous Absorption in Man. In: M. serrano-Rios and P. J. Lefebre (Eds): Diabetes 1985; Proceedings of the 12th Congress of the International Diabetes Federation, Madrid, Spain, 1985 (Excerpta Medica, Amsterdam, (1986) 891–96).

In Table 2 are given the $T_{50\%}$ values of a series of very protracted insulin analogues. The analogues were administered in solutions containing 3 $Zn^{2+}$ per insulin hexamer.

Solubility

The solubility of all the $N^{\epsilon B29}$ modified insulins mentioned in Table 1, which contain 3 $Zn^{2+}$ ions per insulin hexamer, exceeds 600 nmol/ml in a neutral (H 7.5), aqueous, pharmaceutical formulation which further comprises 0.3% phenol as preservative, and 1.6% glycerol to achieve isotonicity. 600 nmol/ml is the concentration of human insulin found in the 100 IU/ml compositions usually employed in the clinic.

The ε-B29 amino group can be a component of an amide bond, a sulphonamide bond, a carbamide a thiocarbamide, or a carbamate. The lipophilic substituent carried by the ε-B29 amino group can also be an alkyl group.

Pharmaceutical compositions containing a human insulin derivative according to the present invention may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of the human insulin derivative in the form of a nasal spray.

The injectable human insulin compositions of the invention can be prepared using the conventional techniques of the pharmaceutical industry which involves dissolving and mixing the ingredients as appropriate to give the desired end product.

Thus, according to one procedure, the human insulin derivative is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a is base, e.g. aqueous sodium hydroxide as needed. Finally, the volume of the solution is adjusted with water to give the desired concentration of the ingredients.

Examples of isotonic agents are sodium chloride, mannitol and glycerol.

Examples of preservatives are phenol, m-cresol, methyl p-hydroxybenzoate and benzyl alcohol.

Examples of suitable buffers are sodium acetate and sodium phosphate.

TABLE 1

| Insulin Derivative *) | Relative Lipophilicity | Blood glucose, % of initial | | | | Index of protraction |
|---|---|---|---|---|---|---|
| | | 1 h | 2 h | 4 h | 6 h | |
| $N^{\epsilon B29}$-benzoyl insulin | 1.14 | | | | | |
| $N^{\epsilon B29}$-phenylacetyl insulin (Zn-free) | 1.28 | 55.4 | 58.9 | 88.8 | 90.1 | 10 |
| $N^{\epsilon B29}$-cyclohexylacetyl insulin | 1.90 | 53.1 | 49.6 | 66.9 | 81.1 | 28 |
| $N^{\epsilon B29}$-cyclohexylpropionyl insulin | 3.29 | 55.5 | 47.6 | 61.5 | 73.0 | 39 |
| $N^{\epsilon B29}$-cyclohexylvaleroyl insulin | 9.87 | 65.0 | 58.3 | 65.7 | 71.0 | 49 |
| $N^{\epsilon B29}$-octanoyl insulin | 3.97 | 57.1 | 54.8 | 69.0 | 78.9 | 33 |
| $N^{\epsilon B29}$-decanoyl, des-(B30) insulin | 11.0 | 74.3 | 65.0 | 60.9 | 64.1 | 65 |
| $N^{\epsilon B29}$-decanoyl insulin | 12.3 | 73.3 | 59.4 | 64.9 | 68.0 | 60 |
| $N^{\epsilon B29}$-undecanoyl, des-(B30) insulin | 19.7 | 88.1 | 80.0 | 72.1 | 72.1 | 80 |
| $N^{\epsilon B29}$-lauroyl, des-(B30) insulin | 37.0 | 91.4 | 90.0 | 84.2 | 83.9 | 78 |
| $N^{\epsilon B29}$-myristoyl insulin | 113 | 98.5 | 92.0 | 83.9 | 84.5 | 97 |
| $N^{\epsilon B29}$-choloyl insulin | 7.64 | 58.2 | 53.2 | 69.0 | 88.5 | 20 |
| $N^{\epsilon B29}$-7-deoxycholoyl insulin (Zn-free) | 24.4 | 76.5 | 65.2 | 77.4 | 87.4 | 35 |
| $N^{\epsilon B29}$-lithocholoyl insulin (Zn-free) | 51.6 | 98.3 | 92.3 | 100.5 | 93.4 | 115 |
| $N^{\epsilon B29}$-4-benzoyl-phenylalanyl insulin | 2.51 | 53.9 | 58.7 | 74.4 | 89.0 | 14 |
| $N^{\epsilon B29}$-3,5-diiodotyrosyl insulin | 1.07 | 53.9 | 48.3 | 60.8 | 82.1 | 27 |
| $N^{\epsilon B29}$-L-thyroxyl insulin | 8.00 | | | | | |

*) 3 $Zn^{2+}$/insulin hexamer except where otherwise indicated.

A composition for nasal administration of an insulin derivative according to the present invention may, for example, be prepared as described in European Patent No. 272097 (to Novo Nordisk A/S).

The insulin compositions of this invention can be used in the treatment of diabetes. The optimal dose level for any patient will depend on a variety of factors including the efficacy of the specific human insulin derivative employed, the age, body weight, physical activity, and diet of the patient, on a possible combination with other drugs, and on the severity of the case of diabetes. It is recommended that the daily dosage of the human insulin derivative of this invention be determined for each individual patient by those skilled in the art in a similar way as for known insulin compositions.

Where expedient, the human insulin derivatives of this invention may be used in mixture with other types of insulin, e.g. human insulin or porcine insulin or insulin analogues with a more rapid onset of action. Examples of such insulin analogues are described e.g. in the European patent applications having the publication Nos. EP 214826 (Novo Nordisk A/S), EP 375437 (Novo Nordisk A/S) and EP 383472 (Eli Lilly &. Co.).

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

EXAMPLES

Plasmids and DNA Material

All expression plasmids are of the cPOT type. Such plasmids are described in EP patent application No. 171 142 and are characterized in containing the *Schizosaccharomyces pombe* triose phosphate isomerase gene (POT) for the purpose of plasmid selection and stabilization. A plasmid containing the POT-gene is available from a deposited *E. coli* strain (ATCC 39685). The plasmids furthermore contain the *S. cerevisiae* triose phosphate isomerase promoter and terminator ($P_{TPI}$ and $T_{TPI}$). They are identical to pMT742 (Egel-Mitani, M. et al. *Gene* 73 (1988) 113≧120) (see FIG. 1) except for the region defined by the ECoRI-XbaI restriction sites encompassing the coding region for signal/leader/product.

Synthetic DNA fragments were synthesized on an automatic DNA synthesizer (Applied Biosystems model 380A) using phosphoramidite chemistry and commercially available reagents (Beaucage, S. L. and Caruthers, M. H., *Tetrahedron Letters* 22 (1981) 1859–1869).

All other methods and materials used are common state of the art knowledge (see, e.g. Sambrook, J., Fritsch, E. F. and Maniatis, T., *Molecular Cloning: A Laboratory Manual*, Cold Spring Harbor Laboratory Press, New York, 1989).

Analytical

Molecular masses of the insulins prepared were obtained by MS (mass spectroscopy), either by PDMS (plasma desorption mass spectrometry) using a Bio-Ion 20 instrument (Bio-Ion Nordic AB, Uppsala, Sweden) or by ESMS (electrospray mass spectrometry) using an API III Biomolecular Mass Analyzer (Perkin-Elmer Sciex Instruments, Thornhill, Canada).

Example 1

Synthesis of Ala$^{A21}$ Asp$^{B3}$ Human Insulin Precursor from Yeast Strain yEA002 using the LaC212spx3 Signal/leader The following oligonucleotides were synthesized:

9 8
5'-TGGCTAAGAGATTCGTTGACCAACACTTGT-GCGGTTCTCACTTGGTTGAA GCTTTGTACTTG-GTTTGTGGTGAAAGAGGTTTCTTCTA-CACTCCAAAGTCTGA CGACGCT-3' (Asp$^{B3}$) (SEQ ID NO:3)

1 2 8
5'-CTGCGGGCTGCGTCTAAGCACAGTAGTTTTC-CAATTGGTACAAAGAACAG ATAGAAGTAC-AACATTGTTCAACGATACCCTTAGCGTCGTCA-GACTTTGG-3' (Ala$^{A21}$) (SEQ ID NO:4)

126 5'-GTCGCCATGGCTAAGAGATTCGTTG-3' (Asp$^{B3}$) (SEQ ID NO:5)

16 5'-CTGCTCTAGAGCCTGCGGGCTGCGTCT-3' (SEQ ID NO:6)

The following Polymerase Chain Reaction (PCR) was performed using the Gene Amp PCR reagent kit (Perkin Elmer, 761 Main Avewalk, Conn. 06859, USA) according to the manufacturer's instructions. In all cases, the PCR mixture was overlayed with 100 μl of mineral oil (Sigma Chemical Co., St. Louis, Mo., USA).

2.5 μl of oligonucleotide #98 (2.5 pmol)
2.5 μl of oligonucleotide #128 (2.5 pmol)
10 μl of 10×PCR buffer
16 μl of dNTP mix
0.54 μl of Taq enzyme
58.5 μl of water One cycle was performed: 94° C. for 45 sec., 49° C. for 1 min, 72° C. for 2 min.

Subsequently, 5 μl of oligonucleotides #16 and #126 was added and 15 cycles were performed: 94° C. for 45 sec., 45° C. for 1 min, 72° C. for 1.5 min. The PCR mixture was loaded onto a 2.5% agarose gel and subjected to electrophoresis using standard techniques (Sambrook et al., Molecular cloning, Cold Spring Harbour Laboratory Press, 1989). The resulting DNA fragment was cut out of the agarose get and isolated using the Gene Clean Kit (Bio 101 Inc., PO BOX. 2284, La Jolla, Calif. 92038, USA) according to the manufacturer's instructions. The purified PCR DNA fragment was dissolved in 10 μl of water and restriction endonuclease buffer and cut with the restriction endonucleases NcoI and XbaI according to standard techniques, run on a 2.5% agarose gel and purified using the Gene Clean Kit as described.

The plasmid pAK188 consists of a DNA sequence of 412 bp composed of a EcoRI/NcoI fragment encoding the synthetic yeast signal/leader gene LaC212spx3 (described in Example 3 of WO 89/02463) followed by a synthetic NcoI/XbaI fragment encoding the insulin precursor MI5, which has a SerAspAspAlaLys bridge connecting the B29 and the A1 amino acid residues (see SEQ ID NOS. 14, 15 and 16), inserted into the EcoRI/XbaI fragment of the vector (phagemid) pBLUESCRIPT IIsk(+/−)(Stratagene, USA). The plasmid pAK188 is shown in FIG. 1.

The plasmid pAk188 was also cut with the restriction endonucleases NcoI and XbaI and the vector fragment of 3139 bp isolated. The two DNA fragments were ligated together using T4 DNA ligase and standard conditions (Sambrook et al., Molecular Cloning, Cold Spring Harbour Laboratory Press, 1989). The ligation mixture was transformed into a competent *E. coli* strain (R−, M+) followed by selection for ampicillin resistance. Plasmids were isolated from the resulting *E. coli* colonies using standard DNA miniprep technique (Sambrook et al., Molecular Cloning, Cold Spring Harbour Laboratory Press, 1989), checked with appropriate restrictions endonucleases i.e. EcoRI, XbaI, NcoI and HpaI. The selected plasmid was shown by DNA sequencing analyses (Sequenase, U.S. Biochemical Corp.) to contain the correct sequence for the Ala$^{A21}$, Asp$^{B3}$ human insulin precursor and named pEA5.3.

The plasmid pKFN1627 is an *E. coli-S. cerevisiae* shuttle vector, identical to plasmid pKFN1003 described in EP patent No. 375718, except for a short DNA sequence upstream from the unique XbaI site. In pKFN1003, this sequence is a 178 bp fragment encoding a synthetic aprotinin gene fused in-frame to the yeast mating factor alpha 1 signal-leader sequence. In pKFN1627, the corresponding 184 bp sequence encodes the insulin precursor MI5 (Glu$^{B1}$, Glu$^{B28}$) (i.e. B(1–29, Glu$^{B1}$, Glu$^{B28}$)-SerAspAspAlaLys-A (1–21) fused in-frame to the mating factor alpha 1 sequence (see SEQ ID NOS. 17, 18 and 19). The vector pKFN1627 is shown in FIG. 1.

pEA5.3 was cut with the restriction endonucleases EcoRI and XbaI and the resulting DNA fragment of 412 bp was isolated. The yeast expression vector pKFN1627 was cut with the restriction endonucleases NcoI and XbaI and with NcoI and EcoRI and the DNA fragment of 9273 bp was isolated from the first digestion and the DNA fragment of 1644 bp was isolated from the second. The 412 bp EcoRI/ XbaI fragment was then ligated to the two other fragments, that is the 9273 bp NcoII/XbaI fragment and the 1644 bp NcoI/EcoRI fragment using standard techniques.

The ligation mixture was transformed into E. coli as described above. Plasmid from the resulting E. coli was isolated using standard techniques, and checked with appropriate restriction endonucleases i.e. EcoRI, XbaI, NcoI, HpaI. The selected plasmid was shown by DNA sequence analysis (using the Sequenase kit as described by the manufacturer, U.S. Biochemical) to contain the correct sequence for the $Ala^{A21}$ $Asp^{B3}$ human insulin precursor DNA and to be inserted after the DNA encoding the LaC212spx3 signal/leader DNA. The plasmid was named pEA5.3.2 and is shown in FIG. 1. The DNA sequence encoding the LaC212spx3 signal/leader/$Ala^{A21}$ $Asp^{B3}$ human insulin precursor complex and the amino acid sequence thereof are SEQ ID NOS. 20, 21 and 22. The plasmid pEA5.3.2 was transformed into S. cervisiae strain MT663 as described in European patent application having the publication No. 214826 and the resulting strain was named yEA002.

Example 2

Synthesis of $Ala^{A21}$ $Thr^{B3}$ Human Insulin Precursor from Yeast Strain yEA005 using the LaC212spx3 Signal/leader The following oligonucleotides were synthesized:

101
5'-TGGCTAAGAGATTCGTTACTCAACACTTGTG- CGGTTCTCACTT GGTTGAAGCTTTGTACTTG- GTTGTGGTGAAAGAGGTTTCTTCTACA CTCCAAAGTCTGACGACGCT-3' ($Thr^{B3}$) (SEQ ID NO:7)

128
5'-CTGCGGGCTGCGTCTAAGCACAGTAGTTMT- CCAATTGGTACAAA GAACAGATAGAAGTA- CAACATTGTTCAACGATACCCTTAGCGTCG TCAGACTTTGG-3' ($Ala^{A21}$) (SEQ ID NO:4)

15 5'-GTCGCCATGGCTAAGAGATTCGTTA-3' ($Thr^{B3}$) (SEQ ID NO:8)

16 5'-CTGCTCTAGAGCCTGCGGGCTGCGTCT-3' (SEQ ID NO:6)

The DNA encoding $Ala^{A21}$ $Thr^{B3}$ human insulin precursor was constructed in the same manner as described for the DNA encoding $Ala^{A21}$ $Asp^{B3}$ human insulin precursor in Example 1. The DNA sequence encoding the LaC212spx3 signal/leader/$Ala^{A21}$ $Thr^{B3}$ human insulin precursor complex and the amino acid sequence thereof are SEQ ID NOS. 23, 24 and 25. The plasmid pEA8.1.1 was shown to contain the desired sequence, transformed into S. cerevisiae strain MT663 as described in Example 1 and the resulting strain was named yEA005.

Example 3

Synthesis of $Gly^{A21}$ $Asp^{B3}$ Human Insulin Precursor from Yeast Strain yEA007 using the LaC212spx3 Signal/leader The following oligonucleotides were synthesized:

98
5'-TGGCTAAGAGATTCGTTGACCAACACTTGT- GCGGTTCTCACTTG GTTGAAGCTTTGTACTTG- GTTTGTGGTGAAAGAGGTTTCTTCT ACACT- CCAAAG- TCTGACGACGCT-3' ($Asp^{B3}$) (SEQ ID NO:3)

127
5'-CTGCGGGCTGCGTCTAACCACAGTAGTTCCA- ATTGGTACAA AGAACAGATAGAAGTACAACAT- TGTTCAACGATACCCT TAGCGTCGTCAGA-3' ($Gly^{A21}$) (SEQ ID NO:9)

126 5'-GTCGCCATGGCTAAGAGATTCGTTG-3' ($Asp^{B3}$) (SEQ ID NO:5)

16 5'-CTGCTCTAGAGCCTGCGGGCTGCGTCT-3' (SEQ ID NO:6)

The DNA encoding $Gly^{A21}$ $Asp^{B3}$ human insulin precursor was constructed in the same manner as described for the DNA encoding $Ala^{A21}$ $Asp^{B3}$ human insulin precursor in Example 1. The DNA sequence encoding the LaC212spx3 signal/leader/$Gly^{A21}$ $Asp^{B3}$ human insulin precursor complex and the amino acid sequence thereof are SEQ ID NOS. 26, 27 and 28. The plasmid pEA1.5.6 was shown to contain the desired sequence, transformed into S. cerevisiae strain MT663 as described in Example 1 and the resulting strain was named yEA007.

Example 4

Synthesis of $Gly^{A21}$ $Thr^{B3}$ Human Insulin Precursor from Yeast Strain yEA006 using the LaC212spx3 Signal/leader The following oligonucleotides were synthesized:

101
5'-TGGCTAAGAGATTCGTTACTCAACACTTGTG- CGGTTCTCACTTGGTTGAAG CTTTGTACTTG- GTTTGTGGTGAAAGAGGTTTCTTCTA- CACTCCAAAGTCTGACG ACGCT-3' ($Thr^{B3}$) (SEQ ID NO:7)

127
5'-CTGCGGGCTGCGTCTAACCACAGTAGTTTTC- CAATTGGTACAAAGAACAG ATAGAAGT- ACAACATTGTTCAACGATACCCTTAGCGTCG- TCAGACTTTGG-3' ($Gly^{A21}$) (SEQ ID NO:9)

15 5'-GTCGCCATGGCTAAGAGATTCGTTA-3' ($Thr^{B3}$) (SEQ ID NO:8)

16 5'-CTGCTCTAGAGCCTGCGGGCTGCGTCT-3' (SEQ ID NO:6)

The DNA encoding $Gly^{A21}$ $Thr^{B3}$ human insulin precursor was constructed in the same manner as described for the DNA encoding $Ala^{A21}$ $Asp^{B3}$ human insulin precursor in Example 1. The DNA sequence encoding the LaC212spx3 signal/leader/$Gly^{A21}$ $Thr^{B3}$ human insulin precursor complex and the amino acid sequence thereof are SEQ ID NOS. 29, 30 and 31. The plasmid pEA4.4.11 was shown to contain the desired DNA sequence, transformed into S. cervisiae strain MT663 as described in Example 1 and the resulting strain was named yEA006.

Example 5

Synthesis of Arg$^{B-1}$ Arg$^{B31}$ Single Chain Human Insulin Precursor having an N-terminal Extension (GluGluAlaGluAlaGluAlaArg) from Yeast Strain yEA113 using the Alpha Factor Leader A) The Following Oligonucleotides were Synthesized:

220 5'-ACGTACGTTCTAGAGCCTGCGGGCTGC-3' (SEQ ID NO:10)

263
5'-CACTTGGTTGAAGCTTTGTACTTGGTTTGTG-GTGAAAGAGGTTTC
TTCTACACTCCAAAGACTAGAGGTATCGTTGA-A-3' (SEQ ID NO:11)

307
5'-GCTAACGTCGCCATGGCTAAGAGAGAAGAA-GCTGAAGCTGAAGCT
AGATTCGTTAACCAACAC-3' (SEQ ID NO:12)

The following Polymerase Chain Reaction (PCR) was performed using the Gene Amp PCR reagent kit (Perkin Elmer, 761 Main Avewalk, Conn. 06859, USA) according to the manufacturer's instructions. In all cases, the PCR mixture was overlayed with 100 μl of mineral oil (Sigma Chemical Co, St. Louis, Mo., USA). The plasmid pAK220 (which is identical to pAK188) consists of a DNA sequence of 412 bp encoding the synthetic yeast signal/leader LaC212spx3 (described in Example 3 of WO 89/02463) followed by the insulin precursor MI5 (see SEQ ID NOS. 14, 15 and 16) inserted into the vector (phagemid) pBLUESCRIPT IIsk(+/−) (Stratagene, USA).

5 μl of oligonucleotide #220 (100 pmol)
5 μl of oligonucleotide #263 (100 pmol)
10 μl of 10×PCR buffer
16 μl of dNTP mix
0.5μl of Taq enzyme
0.5μl of pAK220 plasmid (identical to pAK188) as template (0.2 μg of DNA)
63 μl of water A total of 16 cycles were performed, each cycle comprising 1 minute at 95° C.; 1 minute at 40° C.; and 2 minutes at 72° C. The PCR mixture was then loaded onto a 2% agarose gel and subjected to electrophoresis using standard techniques. The resulting DNA fragment was cut out of the agarose gel and isolated using the Gene Clean kit (Bio 101 Inc., PO BOX 2284, La Jolla, Calif. 92038, USA) according to the manufacture's instructions. The purified PCR DNA fragment was dissolved in 10 μl of water and restriction endonuclease buffer and cut with the restriction endonucleases HindIII and XbaI according to standard techniques. The HindIII/XbaI DNA fragment was purified using The Gene Clean Kit as described.

Figure 2:
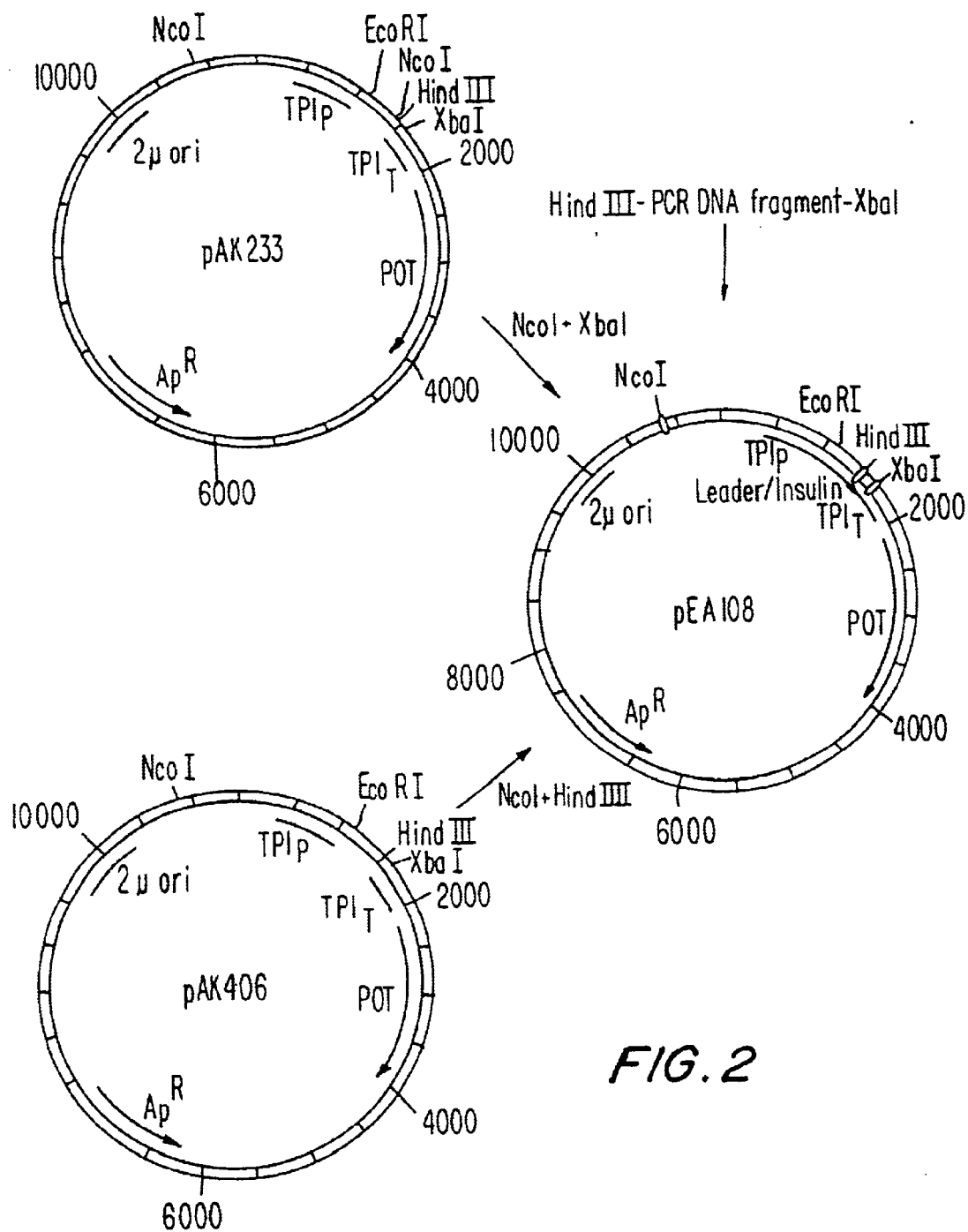
FIG. 2 shows the construction of the plasmid pEA108.

The plasmid pAK406 consists of a DNA sequence of 520 bp comprising an EcoRI/HindIII fragment derived from pMT636 (described in WO 90/10075) encoding the yeast alpha factor leader and part of the insulin precursor ligated to the HindIII/XbaI fragment from pAK188 encoding the rest of the insulin precursor MI5 (see SEQ ID NOS. 32, 33 and 34) inserted into the vector cPOT. The vector pAK406 is shown in FIG. 2.

The plasmid pAK233 consists of a DNA sequence of 412 bp encoding the synthetic yeast signal/leader LaC212spx3 (described in Example 3 of WO 89/02463) followed by the gene for the insulin precursor B(1–19)-GluLysArg-A(1–21) (A21-Gly) (see SEQ ID NOS. 35, 36 and 37) inserted into the vector cPOT. The plasmid pAK233 is shown in FIG. 2.

The plasmid pAK233 was cut with the restriction endonucleases NcoI and XbaI and the vector fragment of 9273 bp isolated. The plasmid pAK406 was cut with the restriction endonucleases NcoI and HindIII and the vector fragment of 2012 bp isolated. These two DNA fragments were ligated together with the HindIII/XbaI PCR fragment using T4 DNA ligase and standard conditions. The ligation mixture was then transformed into a competent E. coli strain (R−, M+) followed by selection for ampicillin resistance. Plasmids were isolated from the resulting E. coli colonies using a standard DNA miniprep technique and checked with appropriate restriction endonucleases i.e. EcoRI, XbaI, NcoI, HindIII. The selected plasmid was shown by DNA sequencing analyses to contain the correct sequence for the Arg$^{B31}$ single chain human insulin precursor DNA and to be inserted after the DNA encoding the S. cervisiae alpha factor DNA. The plasmid was named pEA108 and is shown in FIG. 2. The DNA sequence encoding the alpha factor leader/Arg$^{B31}$ single chain human insulin precursor complex and the amino acid sequence thereof are SEQ ID NOS. 38, 39 and 40. The plasmid pEA 108 was transformed into S. cervisiae strain MT663 as described in Example 1 and the resulting strain was named yEA108.

B) The following Polymerase Chain Reaction (PCR) was performed using the Gene Amp PCR reagent kit (Perkin Elmer, 761 Main Avewalk, Conn. 06859, USA) according to the manufacturer's instructions. In all cases, the PCR mixture was overlayed with 100 μl of mineral oil (Sigma Chemical Co., St. Louis, Mo., USA)

5 μl of oligonucleotide #220 (100 pmol)
5 μl of oligonucleotide #307 (100 pmol)
10 μl of 10×PCR buffer
16 μl of dNTP mix
0.5 μl of Taq enzyme
0.2 μl of pEA108 plasmid as template (0.1 ug DNA)
63 μl of water A total of 16 cycles were performed, each cycle comprising 1 minute at 95° C.; 1 minute at 40° C.; and 2 minutes at 72° C. The PCR mixture was then loaded onto an 2% agarose gel and subjected to electrophoresis using standard techniques. The resulting DNA fragment was cut out of the agarose gel and isolated using the Gene Clean kit (Bio 101 Inc., PO BOX 2284, La Jolla, Calif. 92038, USA) according to the manufacture's instructions. The purified PCR DNA fragment was dissolved in 10 μl of water and restriction endonuclease buffer and cut with the restriction endonucleases NcoI and XbaI according to standard techniques. The NcoI/XbaI DNA fragment was purified using The Gene Clean Kit as described.

Figure 3:
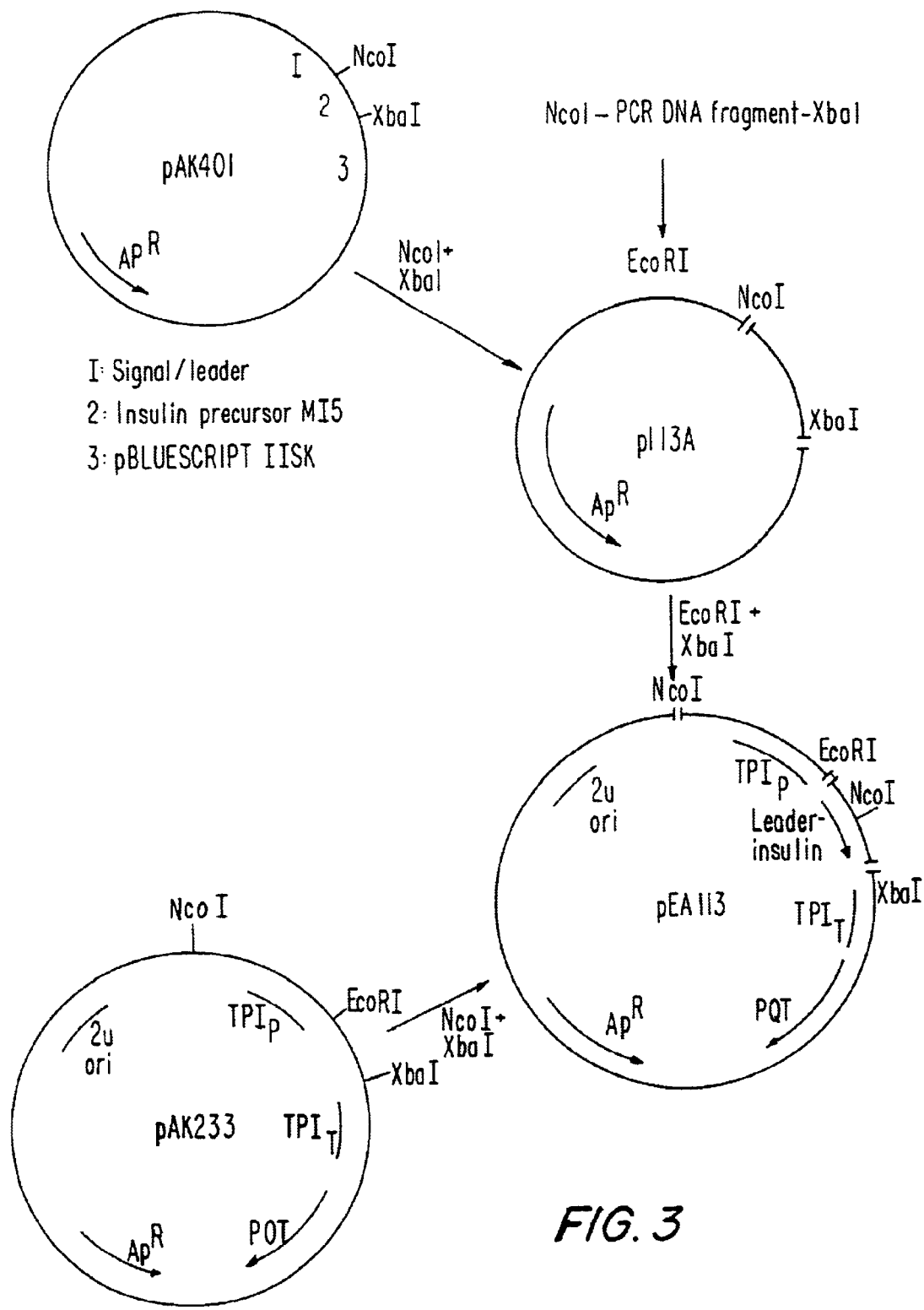
FIG. 3 shows the construction of the plasmid pEA113.

The plasmid pAK401 consists of a DNA sequence of 523 bp composed of an EcoRI/NcoI fragment derived from pMT636 (described in WO 90/10075) (constructed by by introducing a NcoI site in the 3'-end of the alpha leader by site directed mutagenesis) encoding the alpha factor leader followed by a NcoI/XbaI fragment from pAK188 encoding the insulin precursor MI5 (see SEQ ID NOS. 41, 42 and 43) inserted into the vector (phagemid) pBLUESCRIPT IIsk (+/−) (Stratagene, USA). The plasmid pAK401 is shown in FIG. 3.

The plasmid pAK401 was cut with the restriction endonucleases NcoI and XbaI and the vector fragment of 3254 bp isolated and ligated together with the NcoI/XbaI PCR fragment. The ligation mixture was then transformed into a competent E. coli strain and plasmids were isolated from the resulting E. coli colonies using a standard DNA miniprep technique and checked with appropriate restriction endonucleases i.e. EcoRI, XbaI, NcoI. The selected plasmid, named p113A (shown in FIG. 3), was cut with EcoRI and XbaI and the fragment of 535 bp isolated.

The plasmid pAK233 was cut with the restriction endonucleases NcoI and XbaI, and with EcoRI/NcoI and the fragments of 9273 and 1644 bp isolated. These two DNA fragments were ligated together with the EcoRI/XbaI fragment from p113A using T4 DNA ligase and standard conditions. The ligation mixture was then transformed into a competent E. coli strain (R−, M+) followed by selection for ampicillin resistance. Plasmids were isolated from the resulting E. coli colonies using a standard DNA miniprep technique and checked with appropriate restriction endonucleases i.e. EcoRI, XbaI, NcoI, HindIII. The selected plasmid was shown by DNA sequencing analyses to contain the correct sequence for the Arg$^{B31}$ single chain human insulin precursor DNA with the N-terminal extension GluGluAla-GluAlaGluAlaArg and to be inserted after the DNA encoding the S. cerevisiae alpha factor DNA. The plasmid was named pEA113 and is shown in FIG. 3. The DNA sequence encoding the alpha factor leader/Arg$^{B-1}$ Arg$^{B31}$ single chain human insulin precursor having an N-terminal extension (GluGluAlaGluAlaGluAlaArg) and the amino acid sequence thereof are SEQ ID NOS. 44, 45 and 46. The plasmid pEA113 was transformed into S. cervisiae strain MT663 as described in Example 1 and the resulting strain was named yEA113.

Example 6

Synthesis of Arg$^{B-1}$ Arg$^{B31}$ Single Chain Human Insulin Precursor having an N-terminal Extension (GluGluAlaGluAlaGluAlaGluArg) from Yeast Strain yEA136 using the Alpha Factor Leader The following oligonucleotide was synthesized:
389
5'-GCTAACGTCGCCATGGCTAAGAGAGAAGAA-GCTGAAGCGAAGCTGAAAGATT CGTTAAC-CAACAC-3' (SEQ ID NO:13)

The following PCR was performed using the Gene Amp PCR reagent kit 5 µl of oligonucleotide #220 (100 pmol) 5 µl of oligonucleotide #389 (100 pmol) 10 µl of 10×PCR buffer 16 µl of dNTP mix 0.5 µl of Taq enzyme 2 µl of pEA113 plasmid as template (0.5 ug DNA) 63 µl of water A total of 12 cycles were performed, each cycle comprising 1 minute at 95° C.; 1 minute at 37° C.; and 2 minutes at 72° C.

The DNA encoding alpha factor leader/Arg$^{B-1}$ Arg$^{B31}$ single chain human insulin precursor having an N-terminal extension (GluGluAlaGluAlaGluAlaGluArg) was constructed in the same manner as described for the DNA encoding alpha factor leader/Arg$^{B-1}$ Arg$^{B31}$ single chain human insulin precursor having an N-terminal extension (GluGluAlaGluAlaGluAlaArg) in Example 5. The plasmid was named pEA136. The DNA sequence encoding the alpha factor leader/Arg$^{B-1}$ Arg$^{B31}$ single chain human insulin precursor having an N-terminal extension (GluGluAlaGluAlaGluAlaGluArg) and the amino acid sequence thereof are SEQ ID NOS. 47, 48 and 49. The plasmid pEA136 was transformed into S. cerevisiae strain MT663 as described in Example 1 and the resulting strain was named yEA136.

Example 7

Synthesis of (A1,B1)-diBoc Human Insulin 5 g of zinc-free human insulin was dissolved in 41.3 ml of DMSO. To the solution was added 3.090 ml of acetic acid. The reaction was conducted at room temperature and initiated by addition of 565 mg of di-tert-butyl pyrocarbonate dissolved in 5.650 ml of DMSO. The reaction was allowed to proceed for 5½ hour and then stopped by addition of 250 µl of ethanolamine. The product was precipitated by addition of 1500 ml of acetone. The precipitate was isolated by centrifugation and dried in vacuum. A yield of 6.85 g material was obtained.

(A1,B1)-diBoc insulin was purified by reversed phase HPLC as follows: The crude product was dissolved in 100 ml of 25% ethanol in water, adjusted to pH 3.0 with HCl and applied to a column (5 cm diameter, 30 cm high) packed with octadecyldimethylsilyl-substituted silica particles (mean particle size 15 µm, pore size 100 Å) and equilibrated with elution buffer. The elution was performed using mixtures of ethanol and 1 mM aqueous HCl, 0.3 M KCl at a flow of 2 l/h. The insulin was eluted by increasing the ethanol content from 30% to 45%. The appropriate fraction was diluted to 20% ethanol and precipitated at pH 4.8. The precipitated material was isolated by centrifugation and dried in vacuum. Thus 1.701 g of (A1,B1)-diBoc human insulin was obtained at a purity of 94.5%.

Example 8

Synthesis of (N$^{\epsilon B29}$-benzoyl Human Insulin)$_6$, 3Zn$^{2+}$ 400 mg of (A1,B1)-diBoc human insulin was dissolved in 2 ml of DMSO. To the solution was added 748 µl of a mixture of N-methylmorpholine and DMSO (1:9, v/v). The reaction was conducted at 15° C. and initiated by addition of 14.6 mg of benzoic acid N-hydroxysuccinimide ester dissolved in 132 µl DMF. The reaction was stopped after 2 hours by addition of 100 ml of acetone. The precipitated material was isolated by centrifugation and dried in vacuum. 343 mg of material was collected.

The Boc protecting groups were eliminated by addition of 4 ml of TFA. The dissolved material was incubated for 30 minutes and then precipitated by addition of 50 ml of acetone. The precipitate was isolated by centrifugation and dried in vacuum.

N$^{\epsilon B29}$-benzoyl human insulin was purified by reversed phase HPLC as described in Example 7. A yield of 230 mg was obtained. Recrystallization from 15% aqueous ethanol containing 6 mM Zn$^{2+}$ and 50 mM citrate at pH 5.5 gave crystals of the title compound which were isolated by centrifugation and dried in vacuum. The yield was 190 mg.

Molecular mass, found by MS: 5911, theory: 5911.

Example 9

Synthesis of (N$^{\epsilon B29}$-lithocholoyl Human Insulin)$_6$, 3Zn$^{2+}$ 400 mg of (A1,B1)-diBoc human insulin was dissolved in 2 ml of DMSO. To the solution was added 748 µl of a mixture of N-methylmorpholine and DMSO (1:9, v/v). The reaction was conducted at 15° C. and initiated by addition of 31.94 mg of lithocholic acid N-hydroxysuccinimide ester dissolved in 300 µl of DMF. The reaction was stopped after 2 hours by addition of 100 ml of acetone. The precipitated material was isolated by centrifugation and dried in vacuum. 331 mg of material was obtained.

The Boc protecting groups were eliminated by addition of 4 ml of TFA. The dissolved material was incubated for 30 minutes and then precipitated by addition of 50 ml of acetone. The precipitate was isolated by centrifugation and dried in vacuum. The yield was 376 mg.

B29-lithocholoyl insulin was purified by reversed phase HPLC as described in Example 7. A final yield of 67 mg was obtained at a purity of 94%. Recrystallization from 15% aqueous ethanol containing 6 mM $Zn^{2+}$ and 50 mM citrate at pH 5.5 gave crystals of the title compound which were isolated by centrifugation and dried in vacuum. The yield was 49 mg.

Molecular mass, found by MS: 6160, theory: 6166.

Example 10

Synthesis of $(N^{\epsilon B29}\text{-decanoyl Human Insulin})_6$, $3Zn^{2+}$ 400 mg of (A1,B1)-diBoc human insulin was dissolved in 2 ml of DMSO. To the solution was added 748 μl of a mixture of N-methylmorpholine and DMSO (1:9, v/v). The reaction was conducted at 15° C. and initiated by addition of 18.0 mg of decanoic acid N-hydroxysuccinimide ester dissolved in 132 μl of DMF. The reaction was stopped after 60 minutes and the product precipitated by addition of 100 ml of acetone. The precipitated material was isolated by centrifugation and dried in vacuum. 420 mg of intermediate product was collected.

The Boc protecting groups were eliminated by addition of 4 ml of TFA. The dissolved material was incubated for 30 minutes and the product was then precipitated by addition of 50 ml of acetone. The precipitate was isolated by centrifugation and dried in vacuum. The yield of crude product was 420 mg.

The crude product was purified by reversed phase HPLC as described in Example 7. A final yield of 254 mg of the title product was obtained. The purity was 96.1%. Recrystallization from 15% aqueous ethanol containing 6 mM $Zn^{2+}$ and 50 mM citrate at pH 5.5 gave crystals of the title compound which were isolated by centrifugation and dried in vacuum. The yield was 217 mg.

Molecular mass, found by MS: 5962, theory: 5962.

Example 11

Synthesis of des(B30) Human Insulin

Synthesis of des(B30) human insulin was carried out as described by Markussen (Methods in diabetes research, Vol. I, Laboratory methods, part B, 404–410. Ed: J. Lamer and S. Phol, John Wiley & Sons, 1984). 5 g of human insulin was dissolved in 500 ml of water while the pH value of the solution was kept at 2.6 by addition of 0.5 M sulphuric acid. Subsequently, the insulin was salted out by addition of 100 g of ammonium sulphate and the precipitate was isolated by centrifugation. The pellet was dissolved in 800 ml of 0.1 M ammonium hydrogen carbonate and the pH value of the solution was adjusted to 8.4 with 1 M ammonia.

50 mg of bovine carboxypeptidase A was suspended in 25 ml of water and isolated by centrifugation. The crystals were suspended in 25 ml of water and 1 M ammonia was added until a clear solution was obtained at a final pH of 10. The carboxypeptidase solution was added to the insulin solution and the reaction was allowed to proceed for 24 hours. A few drops of toluene were added to act as preservative during the reaction.

After 24 hours the des(B30) human insulin was crystallized by successive addition of 80 g of sodium chloride while the solution was stirred. The pH value was then adjusted to 8.3 and the crystallization was allowed to proceed for 20 hours with gentle stirring. The crystals were isolated on a 1.2 μm filter, washed with 250 ml of ice cold 2-propanol and finally dried in vacuum.

Example 12

Synthesis of (A1,B1)-diBoc des(B30) Human Insulin

The title compound was synthesized by a method similar to that described in Example 7, using des(B30) porcine insulin as the starting material. The crude product was precipitated by acetone and dried in vacuum. The (A1,B1)-diBoc des(B30) human insulin was purified by reversed phase HPLC as described in Example 7.

Example 13

Synthesis of $N^{\epsilon B29}$-decanoyl des(B30) Human Insulin 400 mg of (A1,B1)-diBoc des(B30) human insulin was used as starting material for the synthesis of $N^{\epsilon B29}$-decanoyl des(330) human insulin, following the procedure described in Example 10. The crude product was precipitated by acetone, dried in vacuum and deprotected using TFA. The resulting product was precipitated by acetone and dried in vacuum. $N^{\epsilon B29}$-decanoyl des(B30) human insulin was then purified by reversed phase HPLC as described in Example 10.

Molecular mass, found by MS: 5856, theory: 5861.

Example 14

Synthesis of $N^{\epsilon B29}$-dodecanyl des(B30) Human Insulin a. Immobilization of *A. lyticus* Protease 13 mg of *A. lyticus* protease, dissolved in 5 ml of aqueous 0.2 M $NaHCO_3$ buffer, pH 9.4, was mixed with 4 ml of settled MiniLeak® Medium gel, which had been washed with the same buffer (MiniLeak is a divinylsulfone activated Sepharose CL 6B, obtained from KemEnTec, Copenhagen). The gel was kept in suspension by gentle stirring for 24 hours at room temperature. Then, the gel was isolated by filtration, washed with water, and suspended in 20 ml of 1 M ethanolamine buffer, pH 9.4, and kept in suspension for 24 hours at room temperature. Finally, the gel was washed with water followed by 0.1 M acetic acid and stored at 4° C. The enzyme activity in the filtrate was 13% of that in the initial solution, indicating a yield in the immobilization reaction of about 87%.

b. Immobilization of Porcine Trypsin

Porcine trypsin was immobilized to MiniLeak® Low to a degree of substitution of 1 mg per ml of gel, using the conditions described above for immobilization of *A. lyticus*.

c. Synthesis of $Glu(GluAla)_3Arg\text{-}B(1\text{--}29)$, $ThrArg\text{-}A(1\text{--}21)$ Insulin using Immobilized *A. lyticus* Protease To 200 mg of $Glu(GluAla)_3Arg\text{-}B(1\text{--}29)\text{-}ThrArg\text{-}A(1\text{--}21)$ single-chain human insulin precursor, dissolved in 20 ml of 0.1 M $NaHCO_3$ buffer, pH 9.0, was added 4 ml of the gel carrying the immobilized *A. lyticus* protease. After the gel had been kept in suspension in the reaction mixture for 6 hours at room temperature the hydrolysis was complete, rendering $Glu(GluAla)_3\text{-}Arg\text{-}B(1\text{--}29)$, $ThrArg\text{-}A(1\text{--}21)$ human insulin (the reaction was followed by reversed phase HPLC). After the hydrolysis, the gel was removed by filtration. To the filtrate was added 5 ml of ethanol and 15 μL of 1 M $ZnCl_2$ and the pH was adjusted to 5.0 using HCl. The precipitation of the product was completed on standing overnight at 4° C. with gentle stirring. The product was isolated by centrifugation. After one washing with 1 ml of ice cold 20% ethanol and drying in vacuo the yield was 190 mg.

d. Synthesis of $N^{\alpha A1},N^{\alpha B1},N^{\epsilon B29}$-tridodecanoyl $Glu(GluAla)_3Arg\text{-}B(1\text{--}29)$, $Thr\text{-}Arg\text{-}A(1\text{--}21)$ Human Insulin using Dodecanoic Acid N-hydroxysuccinimide Ester 190 mg (30 μmol) of $Glu(GluAla)_3Arg\text{-}B(1\text{--}29)$, $ThrArg\text{-}A(1\text{--}21)$ insulin was dissolved in 1 ml of DMSO and 1.05 ml of a 0.572 M solution of N,N-diisopropylethylamine in DMF. The solution was cooled to 15° C. and 36 mg (120 μmol) of dodecanoic acid N-hydroxysuccinimide ester dissolved in 0.6 ml of DMSO was added. The reaction was completed within 24 hours. The lipophilic title compound was not isolated.

e. Synthesis of $N^{\epsilon B29}$-dodecanoyl des(B30) Insulin

The product from the previous step, d., contained in approximately 2,65 ml of DMSO/DMF/N,N-diisopropylethylamine was diluted with 10.6 ml of a 50 mM glycine buffer comprising 20% ethanol and the pH adjusted to 10 with NaOH. After standing for 1 hour at room temperature 1 ml of MiniLeak gel, carrying 1 mg of immobilized trypsin per 30 ml of gel, was added. The reaction mixture was stirred gently for 48 hours at room temperature. In order to isolate the desired product, the reaction mixture was applied to a reversed phase HPLC column (5 cm in diameter, 30 cm high), packed with octadecyldimethylsilyl-substituted silica particles (mean particle size 15 μm, pore size 100 Å). For the elution was used 20 mM Tris/HCl buffers, adjusted to pH 7.7 and comprising an increasing concentration of ethanol, from 40% to 44% (v/v), at a rate of 2000 ml/h. The major peak eluting at about 43–44% of ethanol contained the title compound. The fractions containing the major peak were pooled, water was added to reduce the ethanol concentration to 20% (v/v), and the pH was adjusted to 5.5. The solution was left overnight at −20° C., whereby the product precipitated. The precipitate was isolated by centrifugation at −8° C. and dried in vacuo, The yield of the title compound was 90 mg.

Molecular mass, found by MS: 5892, theory: 5890.

Example 15

Synthesis of $N^{\epsilon B29}$-(N-myristoyl-α-glutamyl) Human Insulin 500 mg of (A1,B1)-diBoc human insulin was dissolved in 2.5 ml of DMSO and 428 μl of ethyl deisopropylamine, diluted with 2.5 ml of DMSO/DMF 1/1 (v/v), was added. The temperature was adjusted to 15° C. and 85 mg of N-myristoyl-Glu(OBut) N-hydroxysuccinimide ester, dissolved in 2.5 ml of DMSO/DMF 1/1 (v/v), was added. After 30 min the reaction mixture was poured into 60 ml of water, the pH adjusted to 5 and the precipitate isolated by centrifugation. The precipitate was dried in vacuo. The dried reaction mixture was dissolved in 25 ml of TFA, and the solution was left for 30 min at room temperature. The TFA was removed by evaporation in vacuo. The gelatinous residue was dissolved in 60 ml of water and the pH was adjusted to 11.2 using concentrated ammonia. The title compound was crystallized from this solution by adjustment of the pH to 8.5 using 6 N HCl. The product was isolated by centrifugation, washed once by 10 ml of water, and dried in vacuo. Yield 356 mg. Purity by HPLC 94%.

The product of this example is thus human insulin wherein the ε-amino group of $Lys^{B29}$ has a substituent of the following structure: $CH_3(CH_2)_{12}CONHCH(CH_2CH_2COOH)CO$—.

Molecular mass, found by MS: 6146, theory: 6148.

Example 16

Synthesis of $N^{\epsilon B29}$-undecanoyl des(B30) Human Insulin

The title compound was synthesized analogously to $N^{\epsilon B29}$-dodecanoyl des(B30) human insulin as described in Example 14, by using undecanoic acid N-hydroxysuccinimide ester instead of dodecanoic acid N-hydroxysuccinimide ester.

Molecular mass of the product found by MS: 5876, theory: 5876.

Example 17

Synthesis of $N^{\epsilon B29}$-tridecanoyl des(B30) Human Insulin

The title compound was synthesized analogously to $N^{\epsilon B29}$-dodecanoyl des(B30) human insulin as described in Example 14, by using tridecanoic acid N-hydroxysuccinimide ester instead of dodecanoic acid N-hydroxysuccinimide ester.

Molecular mass of the product found by MS: 5899, theory: 5904.

Example 18

Synthesis of $N^{\epsilon B29}$-myristoyl des(B30) Human Insulin

The title compound was synthesized analogously to $N^{\epsilon B29}$-dodecanoyl des(B30) human insulin as described in Example 14, by using myristic acid N-hydroxysuccinimide ester instead of dodecanoic acid N-hydroxysuccinimide ester.

Molecular mass of the product found by MS: 5923, theory: 5918.

Example 19

Synthesis of $N^{\epsilon B29}$-palmitoyl des(B30) Human Insulin

The title compound was synthesized analogously to $N^{\epsilon B29}$-dodecanoyl des(B30) human insulin as described in Example 14, by using palmitic acid N-hydroxysuccinimide ester instead of dodecanoic acid N-hydroxysuccinimide ester.

Molecular mass of the product found by MS: 5944, theory: 5946.

Example 20

Synthesis of $N^{\epsilon B29}$-suberoyl-D-thyroxine Human Insulin a. Preparation of N-(succinimidylsuberoyl)-D-thyroxine.

Disuccinimidyl suberate (1.0 g, Pierce) was dissolved in DMF (50 ml), and D-thyroxine (2.0 g, Aldrich) was added with stirring at 20° C. The thyroxine slowly dissolved, and after 20 hours the solvent was removed by evaporation in vacuo. The oily residue was crystallized from 2-propanol to yield 0.6 g of N-(succinimidylsuberoyl)-D-thyroxine, m.p. 128–133° C.

b. Reaction of (A1,B1)-diBoc Human Insulin with N-(succinimidylsuberoyl)-D-thyroxine.

(A1,B1)-diBoc human insulin (200 mg) was dissolved in dry DMF (10 ml) by addition of triethylamine (20 μl) at room temperature. Then, N-(succinimidylsuberoyl)-D-thyroxine (80 mg) was added. The reaction was monitored by reversed phase HPLC and when the reaction was about 90% complete, the solvent was removed in vacuo. To the evaporation residue, anhydrous trifluoroacetic acid (5 ml) was added, and the solution was kept for 1 hour at room temperature. After removal of the trifluoroacetic acid in vacuo, the residue was dissolved in a mixture of 1M acetic acid (5 ml) and acetonitrile (1.5 ml), purified by preparative reversed phase HPLC and desalted on a PD-10 column. The yield of $N^{\epsilon B29}$-suberoyl-D-thyroxine human insulin was 50 mg.

The product of this example is thus human insulin wherein the ε-amino group of Lys$^{B29}$ has a substituent of the following structure: Thyrox-CO(CH$_2$)$_6$CO—, wherein Thyrox is thyroxine which is bound to the octanedioic acid moiety via an amide bond to its α-amino group.

Molecular mass of the product found by MS: 6724, theory: 6723.

Example 21

Synthesis of N$^{εB29}$-(2-succinylamido)myristic Acid Human Insulin a. Preparation of α-aminomyristic Acid Methyl Ester,HCl.

To methanol (5 ml, Merck) at −10° C., thionyl chloride (0.2 ml, Aldrich) was added dropwise while stirring vigorously. Then, α-aminomyristic acid (0.7 g, prepared from the α-bromo acid by reaction with ammonia) was added. The reaction mixture was stirred at room temperature overnight, and then evaporated to dryness. The crude product (0.7 g) was used directly in step b.

b. Preparation of N-succinoyl-α-aminomyristic Acid Methyl Ester.

α-Aminomyristic acid methyl ester,HCl (0.7 g) was dissolved in chloroform (25 ml, Merck). Triethylamine (0.35 ml, Fluka) was added, followed by succinic anhydride (0.3 g, Fluka). The reaction mixture was stirred at room temperature for 2 hours, concentrated to dryness, and the residue recrystallized from ethyl acetate/petroleum ether (1/1). Yield: 0.8 g.

c. Preparation of N-(succinimidylsuccinoyl)-α-aminomyristic Acid Methyl Ester.

N-succinoyl-α-aminomyristic acid methyl ester (0.8 g) was dissolved in dry DMF (10 ml, Merck, dried over 4 Å molecular sieve). Dry pyridine (80 μl, Merck), and di(N-succinimidyl)carbonate (1.8 g, Fluka) were added, and the reaction mixture was stirred overnight at room temperature. The evaporation residue was purified by flash chromatography on silica gel 60 (Merck), and recrystallized from 2-propanol/petroleum ether (1/1). Yield of N-(succinimidylsuccinoyl)-α-aminomyristic acid methyl ester: 0.13 g, m.p. 64–66° C.

d. Reaction of (A1,B1)-diBoc Human Insulin with N-(succinimidylsuccinoyl)-α-aminomyristic Acid Methyl Ester.

The reaction was carried out as in Example 20 b., but using N-(succinimidylsuccinoyl)-α-aminomyristic acid methyl ester (16 mg) instead of N-(succinimidylsuberoyl)-D-thyroxine. After removal of the trifluoroacetic acid in vacuo, the evaporation residue was treated with 0.1M sodium hydroxide at 0° C. to saponify the methyl ester. When the saponification was judged to be complete by reversed phase HPLC, the pH value in the solution was adjusted to 3, and the solution was lyophilized. After purification by preparative reversed phase HPLC and desalting on a PD-10 column, the yield of N$^{εB29}$-(2-succinylamido) myristic acid human insulin was 39 mg.

The product of this example is thus human insulin wherein the ε-amino group of Lys$^{B29}$ has a substituent of the following structure: $CH_3(CH_2)_{11}CH(COOH)NHCOCH_2CH_2CO$—.

Molecular mass of the product found by MS: 6130, theory: 6133.

Example 22

Synthesis of N$^{εB29}$-octyloxycarbonyl Human Insulin

The synthesis was carried out as in Example 20 b., but using n-octyloxycarbonyl N-hydroxysuccinimide (9 mg, prepared from n-octyl chloroformate (Aldrich) and N-hydroxysucciniimide), instead of N-(succinimidylsuberoyl)-D-thyroxine. The yield of N$^{εB29}$-octyloxycarbonyl human insulin was 86 mg.

The product of this example is thus human insulin wherein the ε-amino group of Lys$^{B29}$ has a substituent of the following structure: CH$_3$(CH$_2$)$_7$OCO—.

Molecular mass of the product found by MS: 5960, theory: 5964.

Example 23

Synthesis of N$^{εB29}$-(2-succinylamido)palmitic Acid Human Insulin a. Preparation of N-(succinimidylsuccinoyl)-α-amino Palmitic Acid Methyl Ester.

This compound was prepared as described in Example 21 a.–c., using α-amino palmitic acid instead of α-amino myristic acid.

b. Reaction of (A1,B1)-diBoc Human Insulin with N-(succinimidylsuccinoyl)-α-aminopalmitictic Acid Methyl Ester.

The reaction was carried out as in Example 21 d., but using N-(succinimidylsuccinoyl)-α-aminopalmitic acid methyl ester instead of N-(succinimidylsuccinoyl)-α-aminopalmitic acid methyl ester to give N$^{εB29}$-(2 succinylamido)palmitic acid human insulin.

The product of this example is thus human insulin wherein the ε-amino group of Lys$^{B29}$ has a substituent of the following structure: $CH_3(CH_2)_{13}CH(COOH)NHCOCH_2CH_2CO$—.

Example 24

Synthesis of N$^{εB29}$-(2-succinylamidoethyloxy) palmitic Acid Human Insulin a. Preparation of N-(succinimidylsuccinoyl)-2-aminoethyloxy Palmitic Acid Methyl Ester.

This compound was prepared as described in Example 21 a.–c. but using 2-aminoethyloxy palmitic acid (synthesized by the general procedure described by R. TenBrink, *J. Org. Chem.* 52 (1987) 418–422 instead of α-amino myristic acid.

b. Reaction of (A1,B1)-diBoc human insulin with N-(succinimidylsuccinoyl)-2-aminoethyloxypalmitictic Acid Methyl Ester.

The reaction was carried out as in Example 21 d., but using N-(succinimidylsuccinoyl)-2-aminoethyloxypalmitic acid methyl ester instead of N-(succinimidylsuccinoyl)-ε-aminomyristic acid methyl ester to give N$^{εB29}$-(2-succinylamidoethyloxy)palmitic Acid Human Insulin.

The product of this example is thus human insulin wherein the ε-amino group of Lys$^{B29}$ has a substituent of the following structure: $CH_3(CH_2)_{13}CH(COOH)NHCH_2CH_2OCOCH_2CH_2CO$—.

Example 25

Synthesis of N$^{εB29}$-lithocholoyl-α-glutamyl des(B30) Human Insulin

The synthesis was carried out as in Example 13 using N-lithocholoyl-L-glutamic acid α-N-hydroxysuccinimide ester, γ-tert-butyl ester instead of decanoic acid N-hydroxysuccinimide ester.

The product of this example is thus des(B30) human insulin wherein the ε-amino group of Lys$^{B29}$ has a substituent of the following structure: lithocholoyl-NHCH(CH$_2$CH$_2$COOH)CO—.

Molecular mass of the product found by MS: 6194, theory: 6193.

Example 26

Synthesis of $N^{\epsilon B29}$-3,3',5,5'-tetraiodothyroacetyl Human Insulin

The synthesis was carried out as in Example 10 using 3,3',5,5'-tetraiodothyroacetic acid N-hydroxysuccinimide ester, instead of decanoic acid N-hydroxysuccinimide ester.

Molecular mass of the product found by MS: 6536, theory: 6538.

Example 27

Synthesis of $N^{\epsilon B29}$-L-thyroxyl Human Insulin

The synthesis was carried out as in Example 10 using Boc-L-thyroxine N-hydroxysuccinimide ester, instead of decanoic acid N-hydroxysuccinimide ester.

Molecular mass of the product found by MS: 6572, theory: 6567.

Example 28

A Pharmaceutical Composition Comprising 600 nmol/ml of $N^{\epsilon B29}$-decanoyl des(B30) Human Insulin, $\frac{1}{3}Zn^{2+}$ in Solution $N^{\epsilon B29}$-decanoyl des(B30) human insulin (1.2 μmol) was dissolved in water (0.8 ml) and the pH value was adjusted to 7.5 by addition of 0.2 M sodium hydroxide. 0.01 M zinc acetate (60 μl) and a solution containing 0.75% of phenol and 4% of glycerol (0.8 ml) was added. The pH value of the solution was adjusted to 7.5 using 0.2 M sodium hydroxide and the volume of the solution was adjusted to 2 ml with water.

The resulting solution was sterilized by filtration and transferred aseptically to a cartridge or a vial.

Example 29

A Pharmaceutical Composition Comprising 600 nmol/ml of $N^{\epsilon B29}$-decanoyl Human Insulin, $\frac{1}{2}Zn^{2+}$ in Solution 1.2 μmol of the title compound was dissolved in water (0.8 ml) and the pH value was adjusted to 7.5 by addition of 0.2 M sodium hydroxide. A solution containing 0.75% of phenol and 1.75% of sodium chloride (0.8 ml) was added. The pH value of the solution was adjusted to 7.5 using 0.2 M sodium hydroxide and the volume of the solution was adjusted to 2 ml with water.

The resulting solution was sterilized by filtration and transferred aseptically to a cartridge or a vial.

Example 30

A Pharmaceutical Composition Comprising 600 nmol/ml of $N^{\epsilon B29}$-lithocholoyl Human Insulin in Solution 1.2 μmol of the title compound was suspended in water (0.8 ml) and dissolved by adjusting the pH value of the solution to 8.5 using 0.2 M sodium hydroxide. To the solution was then added 0.8 ml of a stock solution containing 0.75% cresol and 4% glycerol in water. Finally, the pH value was again adjusted to 8.5 and the volume of the solution was adjusted to 2 ml with water.

The resulting solution was sterilized by filtration and transferred aseptically to a cartridge or a vial.

Example 31

A Pharmaceutical Composition Comprising a Solution of 600 nmol/ml of $N^{\epsilon B29}$-hexadecanoyl Human Insulin, $\frac{1}{3}$ Zinc Ion per Insulin Monomer, 16 mM m-cresol, 16 mM Phenol, 1.6% Glycerol, 10 mM Sodium Chloride and 7 mM Sodium Phosphate 1.2 μmol of $N^{\epsilon B29}$-hexadecanoyl human insulin was dissolved in water (0.5 ml) by addition of 0.2 M sodium hydroxide to pH 8.0 and 40 μl of 0.01 M zinc acetate was added. To the solution was further added 100 μl of 0.32 M phenol, 200 μl of 0.16 M m-cresol, 800 μl of 4% glycerol, 33.3 μl of 0.6 M sodium chloride, and 140 μl of 0.1 M sodium phosphate (pH 7.5). The pH value of the solution was adjusted to 7.5 with 0.1 M hydrochloric acid and the volume adjusted to 2 ml with water.

Example 32

Solubility of Various Compositions Comprising $N^{\epsilon B29}$-tetradecanoyl des(B30) Human Insulin and $N^{\epsilon B29}$-hexadecanoyl Human Insulin The solubility of $N^{\epsilon B29}$-tetradecanoyl des(B30) human insulin and $N^{\epsilon B29}$-hexadecanoyl human insulin in different compositions was tested. The compositions were prepared as described in Example 31 with the necessary adjustment of the amount of the components. Zinc acetate was either left out or an amount corresponding to $\frac{1}{3}$ $Zn^{2+}$ per insulin monomer was used. Sodium chloride was used in amounts which resulted in a final concentration of 5, 25, 50, 75, 100 or 150 mM of sodium chloride. Zinc-free insulin was added to give a final amount in the composition of 1000 nmol/ml. In some cases a precipitate formed. The resulting solutions and suspensions were kept at 4° C. for a week and the concentration of insulin in solution in each composition was then measured by high performance size exclusion chromatography relative to a standard of human insulin (column: Waters ProteinPak 250×8 mm; eluent: 2.5 M acetic acid, 4 mM arginine, 20% acetonitrile; flow rate: 1 ml/min; injection volume: 40 μl; detection: UV absorbance at 276 nm). The results, in nmol/ml, are given in the table below:

| Solubility of insulins (nmol/ml) in 16 mM phenol, 16 mM m-cresol, 1.6% glycerol, 7 mM sodium phosphate, and pH 7.5, varying zinc acetate and sodium chloride (mM) concentrations at 4° C. | Sodium chloride | | | | | |
|---|---|---|---|---|---|---|
| | 5 mM | 25 mM | 50 mM | 75 mM | 100 mM | 150 mM |
| $N^{\epsilon B29}$-tetradecanoyl des(B30) human insulin, zinc-free. | 82 | 115 | 54 | 77 | 74 | 84 |
| $N^{\epsilon B29}$-tetradecanoyl des(B30) human insulin, $\frac{1}{3}$ $Zn^{2+}$ per insulin monomer. | >950 | >950 | >950 | >950 | >950 | 485 |
| $N^{\epsilon B29}$-hexadecanoyl human insulin, zinc-free. | >890 | >950 | 283 | 106 | 45 | 29 |
| $N^{\epsilon B29}$-hexadecanoyl human insulin, $\frac{1}{3}$ $Zn^{2+}$ per insulin monomer. | >950 | >950 | >950 | >950 | 920 | 620 |

In conclusion it appears that the solubility of the acylated insulins is increased by the addition of zinc. This is contrary to published data on human, porcine and bovine insulin (J Brange: Galenics of Insulin, page 19, Springer Verlag (1987); J Markussen et al. *Protein Engineering* 1 (1987) 205–213).

Example 33

Preparative Crystallization of Zinc-free $N^{\epsilon B29}$-tetradecanoyl des(B30) Human Insulin 10 g of $N^{\epsilon B29}$-tetradecanoyl des(B30) human insulin was dissolved in 120 ml of 0.02 M $NH_4Cl$ buffer adjusted to pH 9.0 with $NH_3$ in ethanol/water (1:4, v/v). Gentle stirring was maintained throughout the crystallization. Crystallization was initiated at 23° C. by addition of 20 ml of 2.5 M NaCl dissolved in ethanol/water (1:4, v/v). A slight turbidity appeared in the solution. Further, 20 ml of 2.5 M sodium chloride dissolved in ethanol/water (1:4, v/v) was added at a constant rate of 5 ml/h, which caused the crystallization to proceed slowly. In order to decrease the solubility of the insulin, the pH value was then adjusted to 7.5 using 1 N hydrochloric acid. Finally, the temperature was lowered to 4° C. and the stirring continued overnight. The crystals were collected by filtration, washed twice with 25 ml of 0.2 M NaCl in ethanol/water (1:4, v/v), sucked dry and lyophilized.

The weight of the wet filter cake was 19.33 g.

The weight of lyophilized filter cake was 9.71 g.

Example 34

Synthesis of Lys$^{B29}$(N$^\epsilon$-[N$^\alpha$-tetradecanoyl-Glu-Gly-]) des(B30) Human Insulin 500 mg of (A1,B1)-diBoc human insulin was dissolved in a mixture of 186 $\mu$l of 4-methylmorpholine and 3814 $\mu$l of DMSO. The reaction was initiated by addition of 144 mg of tetradecanoyl-Glu($\gamma$-OtBu)-Gly-OSu dissolved in 1000 $\mu$l of DMF. The reaction conducted at 15° C. and it was stopped after 4.5 hours by addition of 100 ml of acetone. The reaction product precipitated by addition of a few drops of concentrated HCl was subsequently isolated by centrifugation. The precipitate was then suspended in 100 ml of acetone, isolated by centrifugation and dried in vacuum. 637 mg of material was obtained.

The Boc protecting groups were eliminated by addition of 5 ml of TFA. The dissolved material was incubated for 30 minutes and then precipitated by addition of 100 ml of acetone and a few drops of concentrated HCl. The precipitate was then suspended in 100 ml acetone and isolated by centrifugation. The precipitated material was dissolved in 200 ml of 25% ethanol at pH 8 by addition of NH$_4$OH and purified by reversed phase HPLC. The dissolved material was applied to a column (5 cm diameter, 30 cm high) packed with octadecyldimethylsilyl-substituted silica particles (mean particle size 15 $\mu$m, pore size 100 Å) and equilibrated with 0.02 M Bis-Tris, 30% ethanol adjusted to pH 7.3 with hydrochloric acid at a temperature of 40° C. The elution was performed using mixtures of 70% ethanol in water and Bis-Tris buffer. The flow was 2 l/h. The insulin was eluted by increasing the ethanol content from 30% to 50% and the effluent was monitored by its UV absorbance at 280 nm. The appropriate fraction was diluted to 20% ethanol adjusted to pH 4.5 and frozen at −20° C. The precipitated material was isolated after equilibration of the sample at 1° C. and subsequent centrifugation at the same temperature. The precipitate was dried in vacuum. Thus 292 mg of the title compound was obtained at a purity of 95.5%.

Molecular mass, found by MS: 6102.6, theory: 6103.

The lipophilicity of the title compound, relative to human insulin, k'$_{rel}$=20. The determination was carried out as described on page 23 of the description.

The disappearance half-life, T$_{50\%}$, of the title compound after subcutaneous injection in pigs was found to be 11.9 hours. The determination was carried out as described on page 24 of the description using a composition similar to those described in Table 2 on page 26 of the description.

Example 35

Synthesis of Lys$^{B29}$(N$^\epsilon$-tetradecanoyl-Glu-) des(B30) Human Insulin 500 mg of (A1,B1)-diBoc human insulin was dissolved in a mixture of 186 $\mu$l of 4-methylmorpholine and 3814 $\mu$l of DMSO. The reaction was initiated by addition of 85 mg of N$^\alpha$-tetradecanoyl-Glu(OtBu)-OSu dissolved in 1000 $\mu$l of DMF. The reaction was conducted at 15° C. and it was stopped after 4.5 hours. The remaining process steps were performed as described in Example 34. The intermediate product was isolated and the protection groups were removed by TFA before purification by RP-HPLC and final isolation by precipitation and vacuum drying.

Thus 356 mg of the title compound was obtained at a purity of 94.1%. Molecular mass, found by MS: 6053±6, theory: 6046.

The lipophilicity of the title compound, relative to human insulin, k'$_{rel}$=24. The determination was carried out as described on page 23 of the description.

The disappearance half-life, T$_{50\%}$, of the title compound after subcutaneous injection in pigs was found to be 8.8 hours. The determination was carried out as described on page 24 of the description using a composition similar to those described in Table 2 on page 26 of the description.

Example 36

Synthesis of Lys$^{B29}$(N$^\epsilon$-[N$^\alpha$-tetradecanoyl-Glu(−)-OH]) Human Insulin 400 mg of (A1,B1)-diBoc human insulin was dissolved in a mixture of 232 $\mu$l of ethyldiisopropylamine, 1880 $\mu$l of DMSO and 2088 $\mu$l of 1-methyl-2-pyrrolidone. The reaction was initiated by addition of 138 mg of N$^\alpha$-tetradecanoyl-Glu(OSu)-OtBu dissolved in 800 $\mu$l of 1-methyl-2-pyrrolidone. The reaction was conducted at 15° C. and it was stopped after 4.5 hours. The remaining process steps were performed as described in Example 34. The protection groups were removed from the intermediate product by TFA before purification by RP-HPLC and final isolation by precipitation and vacuum drying.

Thus 222 mg of the title compound was obtained at a purity of 95.5%. Molecular mass, found by MS: 6150±6, theory: 6147.

The lipophilicity of the title compound, relative to human insulin, k'$_{rel}$=21. The determination was carried out as described on page 23 of the description.

The disappearance half-life, T$_{50\%}$, of the title compound after subcutaneous injection is in pigs was found to be 8.0 hours. The determination was carried out as described on page 24 of the description using a composition similar to the one described in the present Example 31.

Example 37

Synthesis of Lys$^{B29}$(N$^\epsilon$-[N$^\alpha$-hexadecanoyl-Glu(−)-OH]) Human Insulin 400 mg of (A1,B1)-diBoc human insulin was dissolved in a mixture of 232 $\mu$l of ethyldiisopropylamine, 880 $\mu$l of DMSO and 2088 $\mu$l of 1-methyl-2-pyrrolidone. The reaction was initiated by addition of 73 mg of N-hexadecanoyl-Glu(OSu)-OtBu dissolved in 800 $\mu$l of DMF. The reaction was conducted at 15° C. and it was stopped after 4.5 hours. The remaining process steps were performed as described in Example 34. 476 mg of intermediate product was obtained. The protection groups were removed from the intermediate product by TFA before purification by RP-HPLC and final isolation by precipitation and vacuum drying.

Thus 222 mg of the title compound was obtained at a purity of 81.2%. Molecular mass, found by MS: 6179±6, theory: 6175.

The lipophilicity of the title compound, relative to human insulin, $k'_{rel}$=67. The determination was carried out as described on page 23 of the description.

The disappearance half-life, $T_{50\%}$, of the title compound after subcutaneous injection in pigs was found to be 13.0 hours. The determination was carried out as described on page 24 of the description using a composition similar to the one described in the present Example 31.

Example 38

Synthesis of $Lys^{B29}(N^\epsilon\text{-}[N^\alpha\text{-octadecanoyl-Glu(-)-OH]})$ des(B30) Human Insulin 400 mg of (A1,B1)-diBoc des(B30) human insulin was dissolved in a mixture of 232 μl of ethyldiisopropylamine, 3000 μl of DMSO and 268 μl of dimetylformamide. The reaction was initiated by addition of 114 mg $N^\alpha$-octadecanoyl-Glu(OSu)-OtBu dissolved in 500 μl of DNF. The reaction was conducted at 15° C. and it was stopped after 4.5 hours. The remaining process steps were performed as described in Example 34. 420 mg of intermediate product was obtained. The protection groups were removed from the intermediate product by TFA before purification by RP-HPLC and final isolation by precipitation and vacuum drying.

Thus 169 mg of the title compound was obtained at a purity of 98.3%. Molecular mass, found by MS: 6103±5, theory: 6102.

The lipophilicity of the title compound, relative to human insulin, $k'_{rel}$=185. The determination was carried out as described on page 23 of the description.

The disappearance half-life, $T_{50\%}$, of the title compound after subcutaneous injection in pigs was found to be 9.7 hours. The determination was carried out as described on page 24 of the description using a composition similar to the one described in the present Example 31.

Example 39

Synthesis of $Lys^{B29}(N^{\epsilon\text{-}[N\alpha}\text{-tetradecanoyl-Glu(-)-OH]})$ des(B30) Human Insulin 400 mg of (A1,B1)-diBoc des(B30) human insulin was dissolved in a mixture of 232 μl of ethyldiisopropylamine and 3000 μl of DMSO. The reaction was initiated by addition of 138 mg of $N^\alpha$-tetradecanoyl-Glu(OSu)-OtBu dissolved in 768 μl of DMF. The reaction was conducted at 15° C. and it was stopped after 4.5 hours. The remaining process steps were performed as described in Example 34. 505 mg of intermediate product was obtained. The protection groups of the intermediate product were removed by TFA before purification by RP-HPLC and final isolation by precipitation and vacuum drying.

Thus 237 mg of the title compound was obtained at a purity of 96.7%. Molecular mass, found by MS: 6053±6, theory: 6046.

The lipophilicity of the title compound, relative to human insulin, $k'_{rel}$=21. The determination was carried out as described on page 23 of the description.

The disappearance half-life, $T_{50\%}$, of the title compound after subcutaneous injection in pigs was found to be 12.8 hours. The determination was carried out as described on page 24 of the description using a composition similar to the one described in the present Example 31.

Example 40

Synthesis of $Lys^{B29}(N^\epsilon\text{-}[N^\alpha\text{-hexadecanoyl-Glu(-)-OH]})$ des(B30) Human Insulin 400 mg of (A1,B1)-diBoc des(B30) human insulin was dissolved in a mixture of 232 μl of ethyldiisopropylamine, 3000 μl of DMSO and 400 μl of dimetylformamide. The reaction was initiated by addition of 73 mg of $N^\alpha$-hexadecanoyl-Glu(OSu)-OtBu dissolved in 400 μl of DMF. The reaction was conducted at 15° C. and it was stopped after 4.5 hours. The remaining process steps were performed as described in Example 34. The protection groups of the intermediate product were removed by TFA before purification by RP-HPLC and final if isolation by precipitation and vacuum drying.

Thus 153 mg of the title compound was obtained at a purity of 95.2%. Molecular Mass, found by MS: 6073±6, theory: 6074.

The lipophilicity of the title compound, relative to human insulin, $k'_{rel}$=67. The determination was carried out as described on page 23 of the description.

The disappearance half-life, $T_{50\%}$, of the title compound after subcutaneous injection in pigs was found to be 18.0 hours. The determination was carried out as described on page 24 of the description using a composition similar to the one described in the present Example 31.

Example 41

Synthesis of $Lys^{B29}(N^\epsilon\text{-}[N^\alpha\text{-lithocholyl-Glu(-)-OH]})$ des(B30) Human Insulin 400 mg of (A1,B1)-diBoc des(B30) human insulin was dissolved in a mixture of 148 μl 4-methylmorpholine and 3452 μl of DMSO. The reaction was initiated by addition of 132 mg of $N^\alpha$-lithocholoyl-Glu(OSu)-OtBu dissolved in 400 μl of DMF. The reaction was conducted at 15° C. and it was stopped after 4.5 hours. The remaining process steps were performed as described in Example 34. 493 mg of intermediate product was obtained. The protection groups of the intermediate product were removed by TFA before purification by RP-HPLC and final isolation by precipitation and vacuum drying.

Thus 209 mg of the title compound was obtained at a purity of 97.4%. Molecular Mass, found by MS: 6185±10, theory: 6194.

Example 42

$Lys^{B29}(N^\epsilon\text{-}[N^\alpha\text{-tetradecanoyl Aad(-)-OH]})$ des(B30) Human Insulin Aad is 5-aminohexadioic acid. 347 mg of (A1,B1)-diBoc des(B30) human insulin was dissolved in a mixture of 129 μl of 4-methylmorpholine and 2645 μl of DMSO. The reaction was initiated by addition of 58 mg of $N^\alpha$-tetradecanoyl-Aad(OSu)-OtBu dissolved in 694 μl of DMF. The activated ester was prepared in analogy with chemistry well-known from as aspartic acid derivatisation (L. Benoiton: Can.J.Chem.40,570–72,1962, R.Roeske: J.Org.Chem 28 1251–93 (1963)). The reaction was conducted at 15° C. and it was stopped after 4.5 hours. The remaining process steps were performed as described in Example 34. The protection groups of the intermediate product were removed by TFA before purification by RP-HPLC and final isolation by precipitation and vacuum drying.

Thus 149 mg of the title compound was obtained at a purity of 97.9%. Molecular Mass, found by MS: 6061±2, theory: 6060.

The lipophilicity of the title compound, relative to human insulin, $k'_{rel}=21$. The determination was carried out as described on page 23 of the description.

The disappearance half-life, $T_{50\%}$, of the title compound after subcutaneous injection in pigs was found to be 16.1 hours. The determination was carried out as described on page 24 of the description using a composition similar to the one described in the present Example 31.

Example 43

Synthesis of $Lys^{B29}(N^\epsilon$-[$N^\alpha$-tetradecanoyl-γ-carboxy-Glu-]) des(B30) Human Insulin 400 mg of (A1,B1)-diBoc des(B30) human insulin was dissolved in a mixture of 190 μl of triethylamine and 3000 μl of DMSO. The reaction was initiated by addition of 83 mg of γ-carboxy Glu N-tetradecansyre γ,γ'-di(OtBu) α-(OSu) (i.e. $(tBuOCO)_2CHCH_2$—$CH(COOSu)$—$NH$—$CO(CH_2)_{12}$ $CH_3$) dissolved in 800 μl of DMF. The reaction was conducted at 15° C. and it was stopped after 4.5 hours. The remaining process steps were performed as described in Example 34. The protection groups of the intermediate product were removed by TFA before purification by RP-HPLC and final isolation by precipitation and vacuum drying.

63 mg of the title compound were obtained. Molecular Mass, found by MS: 6090±3, theory: 6091.

The lipophilicity of the title compound, relative to human insulin, $k'_{rel}=10$. The determination was carried out as described on page 23 of the description.

What is claimed is:

1. An insulin derivative having the following sequence:

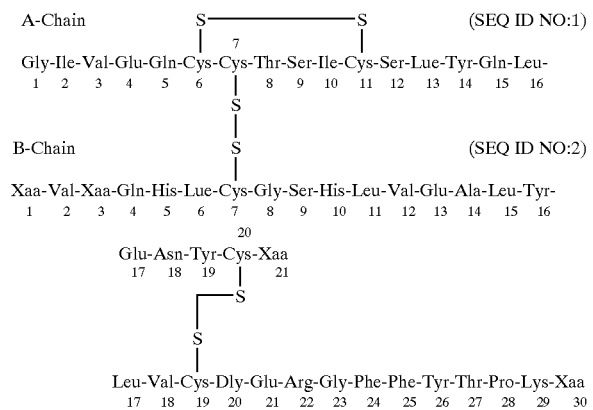

wherein
   a) Xaa at positions A21 and B3 are, independently, any amino acid residue which can be coded for by the genetic code except Lys, Arg and Cys;
   b) Xaa at position B1 is Phe or is deleted;
   c) Xaa at position B30 is deleted; and
   d) the ε-amino group of $Lys^{B29}$ is substituted with a lipophilic substituent having at least 6 carbon atoms.

2. The insulin derivative of claim 1, wherein Xaa at position A21 is Ala, Asn, Gln, Gly or Ser.

3. The insulin derivative of claim 2, wherein the lipophilic substituent has from 12 to 24 carbon atoms.

4. The insulin derivative of claim 1, wherein Xaa at position B1 is deleted.

5. The insulin derivative of claim 4, wherein the lipophilic substituent has from 12 to 24 carbon atoms.

6. The insulin derivative of claim 1, wherein Xaa at position B1 is Phe.

7. The insulin derivative of claim 6, wherein the lipophilic substituent has from 12 to 24 carbon atoms.

8. The insulin derivative of claim 1, wherein Xaa at position B3 is Asn, Asp, Gln or Thr.

9. The insulin derivative of claim 8, wherein the lipophilic substituent has from 12 to 24 carbon atoms.

10. The insulin derivative of claim 1, wherein Xaa at position A21 is Ala, Asn, Gln, Gly or Ser, and Xaa at position B3 is Asn, Asp, Gln or Thr.

11. The insulin derivative of claim 10, wherein the lipophilic substituent has from 12 to 24 carbon atoms.

12. The insulin derivative of claim 1, wherein Xaa at position A21 is Asn, Xaa at position B1 is Phe, and Xaa at position B3 is Asn.

13. The insulin derivative of claim 12, wherein the lipophilic substituent has from 12 to 24 carbon atoms.

14. The insulin derivative of claim 1, wherein the lipophilic substituent has from 12 to 24 carbon atoms.

15. The insulin derivative of claim 1, wherein the lipophilic substituent is cyclohexylvaleroyl.

16. The insulin derivative of claim 1, wherein the lipophilic substituent is acyl-glutamyl wherein the acyl is a linear, saturated acyl having 6 to 24 carbon atoms.

17. The insulin derivative of claim 1, wherein the lipophilic substituent is lauroyl.

18. The insulin derivative of claim 1, wherein the lipophilic substituent is myristoyl.

19. The insulin derivative of claim 1, wherein the lipophilic substituent is palmitoyl.

20. The insulin derivative of claim 1, wherein the lipophilic substituent is 2-succinylamido myristic acid.

21. The insulin derivative of claim 1, wherein the lipophilic substituent is 2-succinylamido palmitic acid.

22. The insulin derivative of claim 1, wherein the lipophilic substituent is 2-succinylamidoethyloxy palmitic acid.

23. The insulin derivative of claim 1, wherein the lipophilic substituent is myristoyl-α-glutamyl.

24. The insulin derivative of claim 1, wherein the lipophilic substituent is myristoyl-α-glutamyl-glycyl.

25. The insulin derivative of claim 1, wherein the lipophilic substituent is choloyl.

26. The insulin derivative of claim 1, wherein the lipophilic substituent is 7-deoxycholoyl.

27. The insulin derivative of claim 1, wherein the lipophilic substituent is lithocholoyl.

28. The insulin derivative of claim 1, wherein the lipophilic substituent is lithocholoyl-glutamyl.

29. The insulin derivative of claim 1, wherein the lipophilic substituent is 4-benzoyl-phenylalanine.

30. The insulin derivative of claim 1, wherein the lipophilic substituent is L-thyroxyl.

31. The insulin derivative of claim 1, wherein the lipophilic substituent is suberoyl-D-thyroxine.

32. The insulin derivative of claim 1, wherein the lipophilic substituent is 3,3',5,5'-tetraiodothyroacetyl.

33. The insulin derivative of claim 1, wherein the lipophilic substituent is an acyl group having at least 10 carbon atoms.

34. The insulin derivative of claim 33, wherein the lipophlic substituent is tetradecanoyl or hexadecanoyl.

35. The insulin derivative of claim 1, which is in the form of a hexamer.

36. The insulin derivative of claim 35, wherein the lipophilic substituent has from 12 to 24 carbon atoms.

37. The insulin derivative of claim 35, wherein Xaa at position A21 is Asn, Xaa at position B3 is Asn, and Xaa at position B1 is Phe.

38. The insulin derivative of claim 35, wherein two zinc ions bind to the hexamer.

39. The insulin derivative of claim 38, wherein the lipophilic substituent has from 12 to 24 carbon atoms.

40. The insulin derivative of claim 35, wherein three zinc ions bind to the hexamer.

41. The insulin derivative of claim 40, wherein the lipophilic substituent has from 12 to 24 carbon atoms.

42. The insulin derivative of claim 35, wherein four zinc ions bind to the hexamer.

43. The insulin derivative of claim 42, wherein the lipophilic substituent has from 12 to 24 carbon atoms.

44. The insulin derivative of claim 12, wherein the lipophilic substituent is tetradecanoyl.

45. A pharmaceutical composition which is an aqueous solution, said composition comprising (a) the insulin derivative of claim 44, (b) an isotonic agent, (c) a preservative and (d) a buffer.

46. The pharmaceutical composition of claim 45, wherein the pH of the aqueous solution is in the range of 6.5–8.5.

47. The pharmaceutical composition of claim 45, wherein the solubility of the insulin derivative exceeds 600 nmol/ml of the aqueous solution.

48. The pharmaceutical composition of claim 45, said composition further comprising an insulin or an insulin analogue which has a rapid onset of action.

49. The pharmaceutical composition of claim 45, wherein the insulin derivative is in the form of a hexamer.

50. A method of treating diabetes in a patient in need of such a treatment, said method comprising administering to the patient a therapeutically effective amount of a pharmaceutical composition of claim 45.

51. A method of treating diabetes in a patient in need of such a treatment, said method comprising administering to the patient a therapeutically effective amount of a pharmaceutical composition of claim 48.

52. A pharmaceutical composition which is an aqueous solution, said composition comprising (a) an insulin derivative of claim 1, (b) an isotonic agent, (c) a preservative and (d) a buffer.

53. The pharmaceutical composition of claim 52, wherein the pH of the aqueous solution is in the range of 6.5–8.5.

54. The pharmaceutical composition of claim 52, wherein the solubility of the insulin derivative exceeds 600 nmol/ml of the aqueous solution.

55. The pharmaceutical composition of claim 52, said composition further comprising an insulin or an insulin analogue which has a rapid onset of action.

56. The pharmaceutical composition of claim 52, wherein Xaa at position A21 is Asn, Xaa at position B3 is Asn, and Xaa at position B1 is Phe.

57. The pharmaceutical composition of claim 52, wherein the lipophilic substituent has from 12 to 24 carbon atoms.

58. The pharmaceutical composition of claim 52, wherein the insulin derivative is in the form of a hexamer.

59. A method of treating diabetes in a patient in need of such a treatment, said method comprising administering to the patient a therapeutically effective amount of a pharmaceutical composition of claim 52.

60. A method of treating diabetes in a patient in need of such a treatment, said method comprising administering to the patient a therapeutically effective amount of a pharmaceutical composition of claim 55.

* * * * *

UNITED STATES PATENT AND TRADEMARK OFFICE
CERTIFICATE OF CORRECTION

PATENT NO. : 6,869,930 B1 Page 1 of 1
APPLICATION NO. : 09/398365
DATED : March 22, 2005
INVENTOR(S) : Havelund et al.

It is certified that error appears in the above-identified patent and that said Letters Patent is hereby corrected as shown below:

Column 79, line 22, Claim 1 – Change "...Lue..." to --...Leu...--

Column 79, line 24, Claim 1 – Change "...Lue..." to --...Leu...--

Column 79, line 34, Claim 1 – Change "...Dly..." to --...Gly...--

Signed and Sealed this

Thirty-first Day of July, 2007

JON W. DUDAS
*Director of the United States Patent and Trademark Office*